US 7,613,501 B2
Nov. 3, 2009

(12) United States Patent
Scherch

(10) Patent No.: US 7,613,501 B2
(45) Date of Patent: Nov. 3, 2009

(54) SYSTEM, TRACKER, AND PROGRAM PRODUCT TO FACILITATE AND VERIFY PROPER TARGET ALIGNMENT FOR RADIATION DELIVERY, AND RELATED METHODS

(75) Inventor: John David Scherch, Pittsburgh, PA (US)

(73) Assignee: Best Medical International, Inc., Springfield, VA (US)

( * ) Notice: Subject to any disclaimer, the term of this patent is extended or adjusted under 35 U.S.C. 154(b) by 208 days.

(21) Appl. No.: 11/455,061

(22) Filed: Jun. 16, 2006

(65) Prior Publication Data
US 2006/0285641 A1    Dec. 21, 2006

Related U.S. Application Data

(60) Provisional application No. 60/691,027, filed on Jun. 16, 2005.

(51) Int. Cl.
*A61B 5/05* (2006.01)
(52) U.S. Cl. .......................... 600/427; 378/65
(58) Field of Classification Search ................ 600/426, 600/427, 429, 436; 378/65, 205, 206, 208, 378/20; 356/620, 622; 250/215, 559.29–559.31
See application file for complete search history.

(56) References Cited

U.S. PATENT DOCUMENTS

| | | | |
|---|---|---|---|
| 3,861,807 A | 1/1975 | Lescrenier et al. | |
| 3,987,281 A | 10/1976 | Hodes et al. | |
| 4,455,609 A | 6/1984 | Inamura et al. | |
| 5,373,844 A | 12/1994 | Smith et al. | |
| 5,511,549 A | 4/1996 | Legg et al. | |
| 5,754,623 A | 5/1998 | Seki et al. | |
| 5,772,594 A | 6/1998 | Barrick | |
| 6,032,066 A | 2/2000 | Lu et al. | |
| 6,360,116 B1 | 3/2002 | Jackson et al. | |
| 6,435,717 B1 | 8/2002 | Kohler et al. | |
| 6,535,574 B1 | 3/2003 | Collins et al. | |
| 6,560,311 B1 | 5/2003 | Shepard et al. | |

(Continued)

FOREIGN PATENT DOCUMENTS

DE    103 35 037 A1    3/2005

(Continued)

*Primary Examiner*—Long V Le
*Assistant Examiner*—Saurel J Selkin
(74) *Attorney, Agent, or Firm*—Jason A. Bernstein; Barnes & Thornburg LLP

(57) ABSTRACT

A system, tracker, program product, and methods to facilitate and verify proper target alignment for radiation delivery are provided. The system includes a radiation delivery apparatus having a radiation emitter, a rotating assembly controlled by a controller, and an application computer which provides treatment delivery instructions to the controller. The system also includes a trackable body having a trackable body reference point to be positioned adjacent a surface point of a patient to determine a position of such surface point. The system also includes an apparatus to track a trackable body which has a trackable body detector to detect a position of indicators carried by the trackable body and a trackable body determiner to determine a position of the trackable body reference point. The system also includes a target alignment analyzing computer having memory and target alignment analyzing program product stored therein to aid a user of the system to make and display various patient body-surface related measurements.

35 Claims, 16 Drawing Sheets

U.S. PATENT DOCUMENTS

| | | |
|---|---|---|
| 2002/0080915 A1 | 6/2002 | Frohlich et al. |
| 2002/0122530 A1 | 9/2002 | Erbel et al. |
| 2002/0188194 A1* | 12/2002 | Cosman ................ 600/426 |
| 2002/0193685 A1 | 12/2002 | Mate et al. |
| 2004/0015077 A1 | 1/2004 | Sati et al. |
| 2004/0122311 A1 | 6/2004 | Cosman |
| 2004/0138556 A1 | 7/2004 | Cosman |
| 2005/0020917 A1 | 1/2005 | Scherch |
| 2005/0215888 A1* | 9/2005 | Grimm et al. ............ 600/426 |

FOREIGN PATENT DOCUMENTS

| | | |
|---|---|---|
| EP | 0 910 990 A1 | 4/1999 |
| EP | 0911065 A | 4/1999 |
| EP | 1041918 | 11/2000 |
| EP | 1 419 801 A | 5/2004 |
| WO | WO 99/27839 A2 | 6/1999 |
| WO | WO 00/47103 A2 | 8/2000 |
| WO | WO 00/56215 A1 | 9/2000 |
| WO | WO 01/06924 A1 | 2/2001 |
| WO | WO 02/09588 A | 2/2002 |
| WO | WO 02/49044 A2 | 6/2002 |
| WO | WO 2005/018734 A | 3/2005 |
| WO | WO 2005/099819 A | 10/2005 |

* cited by examiner

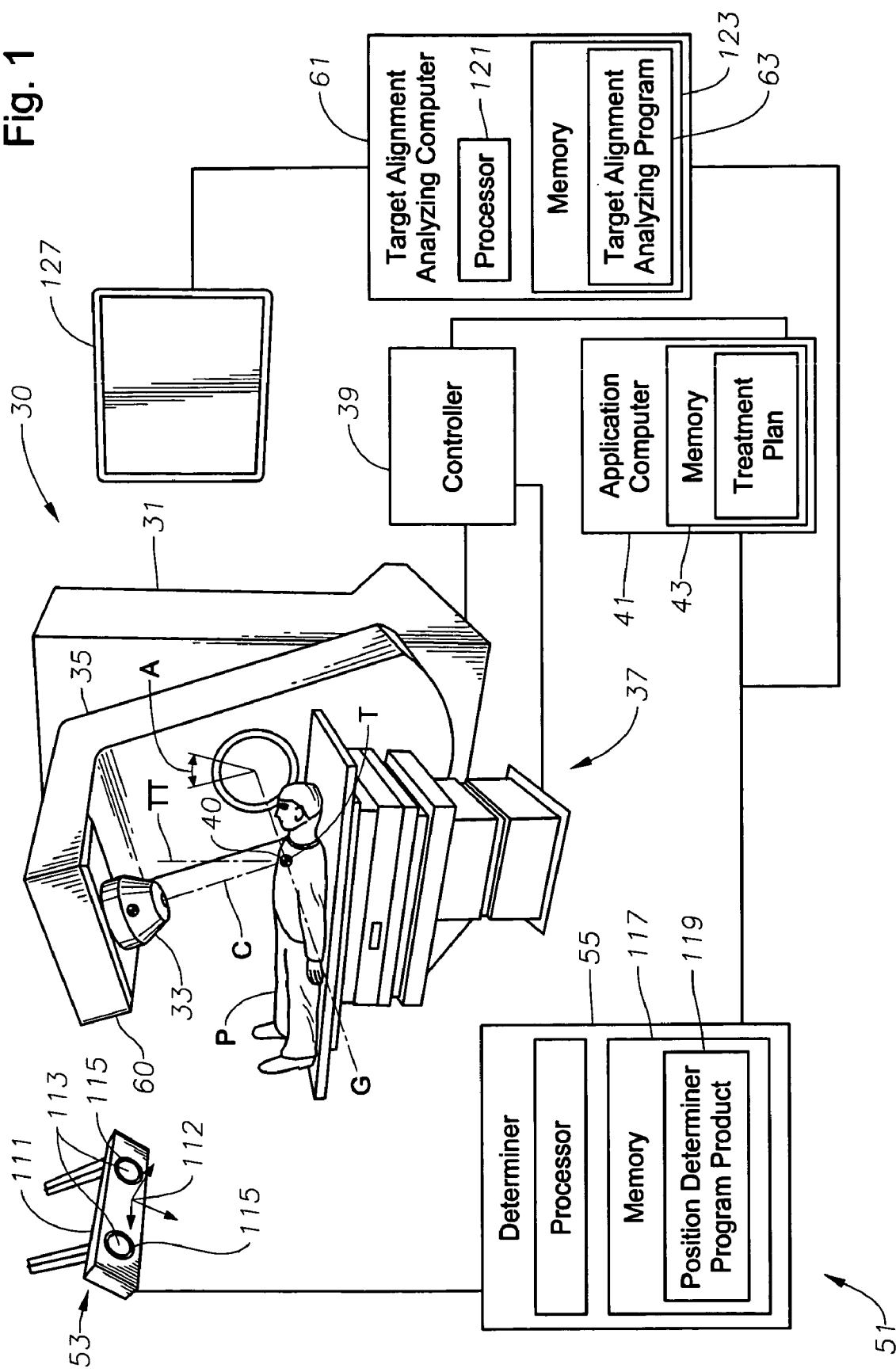

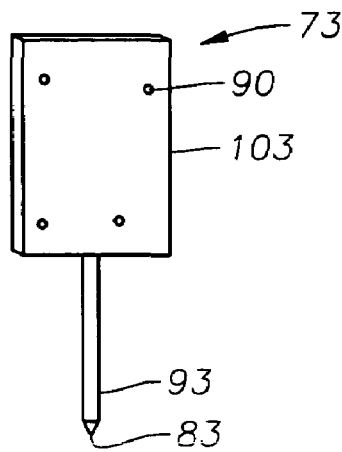
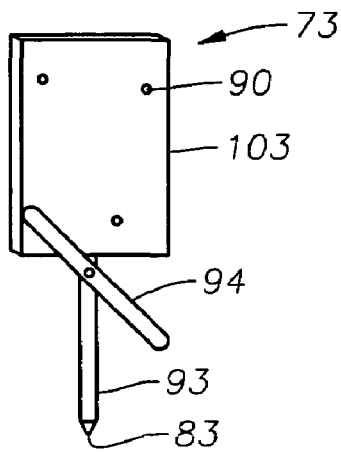
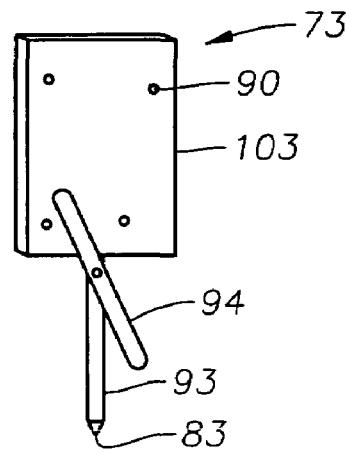
Fig. 4        Fig. 6A        Fig. 6B
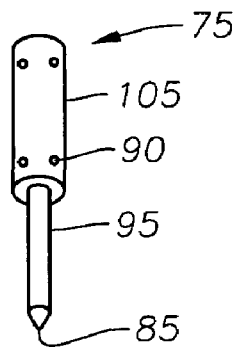
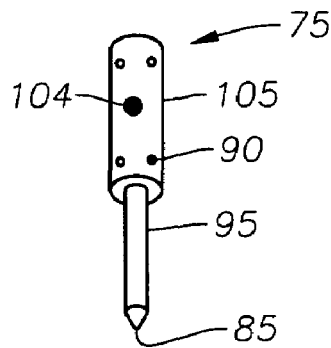
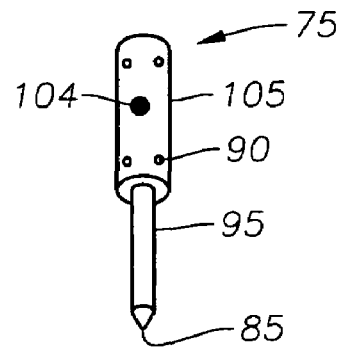
Fig. 5        Fig. 7A        Fig. 7B
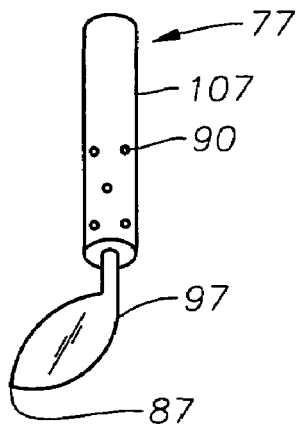
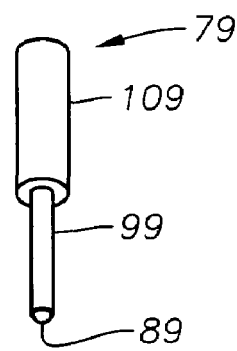
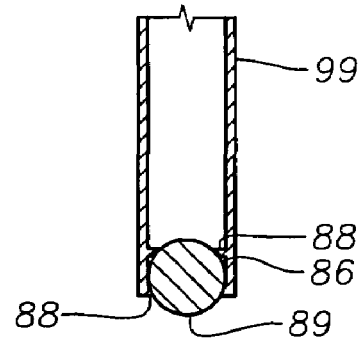
Fig. 8        Fig. 9A        Fig. 9B Fig. 15
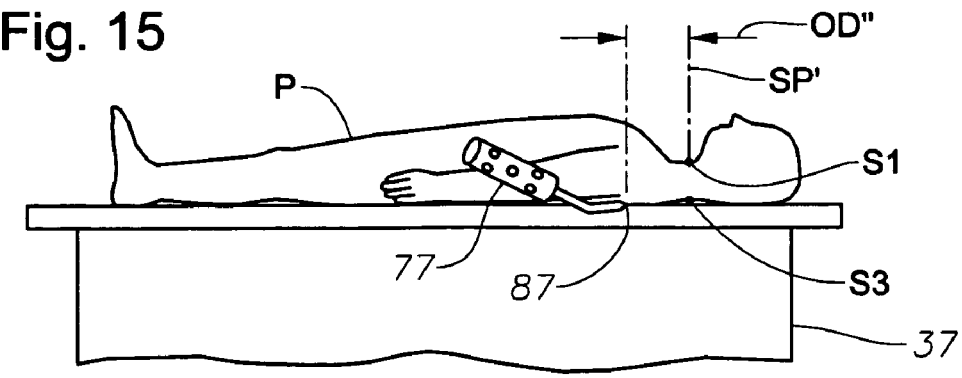
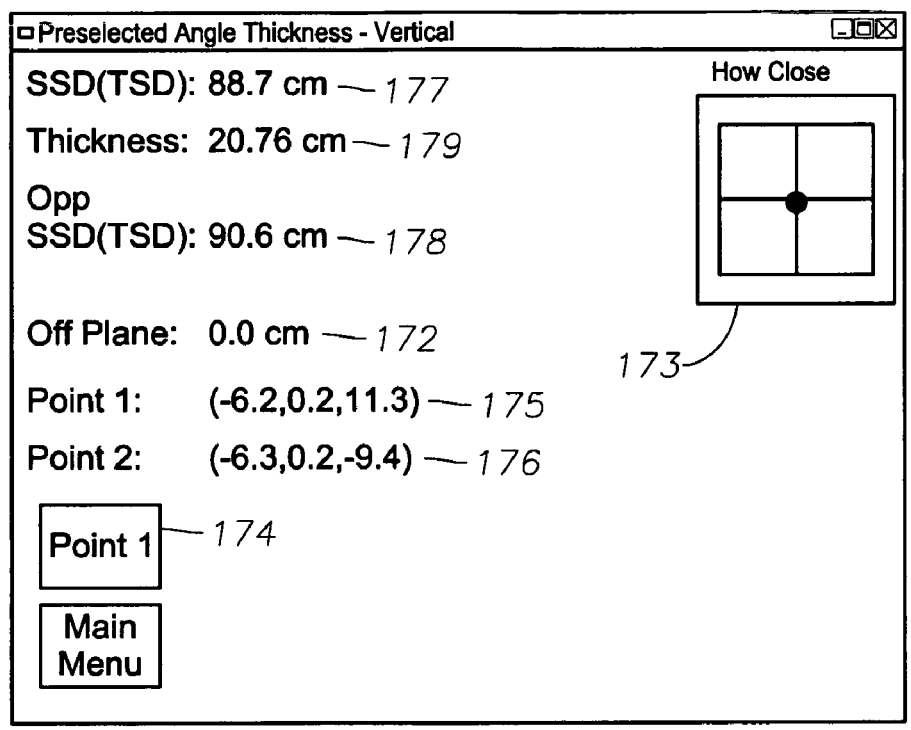
Fig. 16
Fig. 17
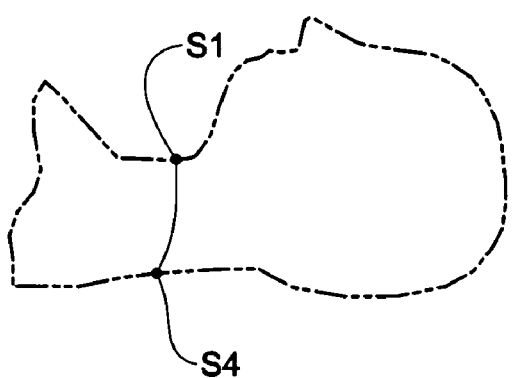

SYSTEM, TRACKER, AND PROGRAM PRODUCT TO FACILITATE AND VERIFY PROPER TARGET ALIGNMENT FOR RADIATION DELIVERY, AND RELATED METHODS

RELATED APPLICATIONS

This application claims priority to and the benefit of U.S. Provisional Application No. 60/691,027, filed on Jun. 16, 2005, incorporated herein by reference in its entirety.

BACKGROUND OF THE INVENTION

1. Field of the Invention

The present invention relates to patient therapy. More specifically, the present invention relates to a system, tracker, program product, and related methods to facilitate and verify proper target alignment for radiation delivery so that a treatment plan can be more accurately applied to a patient.

2. Description of the Related Art

Radiation therapy can be effective in treating certain types of cancerous tumors, lesions, or other "targets." A vast majority of such targets can be eradicated completely if a sufficient radiation dose is delivered to the tumor or lesion volume. Complications, however, may result from use of the necessary effective radiation dose, due to damage to healthy tissue which surrounds the target or to other healthy body organs located close to the target. The goal of various radiation procedures, such as conformal radiation therapy treatment, is to confine the delivered radiation dose to only the target volume defined by the outer surfaces of the target, while minimizing the dose of radiation to surrounding healthy tissue or adjacent healthy organs. If the effective radiation dose is not delivered to the proper location within the patient, serious complications may result.

Radiation therapy treatment typically uses a radiation delivery apparatus or device, such as a linear accelerator or other radiation producing source, to treat the target. For example, the conventional linear accelerator includes a rotating gantry assembly which generally rotates about a horizontal axis and which has a radiation beam source or emitter positionable about the patient which can direct a radiation beam toward the target to be treated. The linear accelerator can also include a rotating treatment table assembly which generally rotates about a vertical axis and which can position the target within a rotational plane of the rotating gantry assembly. Various types of apparatus can further conform the shape of the radiation treatment beam to follow the spatial contour of the target as seen by the radiation treatment beam, from a linear accelerator, as it passes through the patient's body into the target during rotation of the radiation beam source. Multileaf collimators having multiple leaf or finger projections can be programmed to move individually into and out of the path of the radiation beam to shape the radiation beam.

Various types of radiation treatment planning systems can create a radiation treatment plan, which, when implemented, will deliver a specified dose of radiation shaped to conform to the target volume, while limiting the radiation dose delivered to sensitive surrounding healthy tissue or adjacent healthy organs or structures. Typically, the patient has the radiation therapy treatment plan prepared, based upon a diagnostic study through the use of computerized tomographic ("CT") scanning, magnetic resonance ("MR") imaging, or conventional simulation films, which are plain x-rays generated with the patient, and thus the patient's tumor or lesion, in the position which will be used during the radiation therapy treatment.

Placement of the radiation beams in the proper juxtaposition with the patient to be treated is typically accomplished by referencing both the radiation beam and the patient position to a coordinate system referred to as the isocenter coordinate system, which is defined by the geometry of the radiation delivery apparatus. In the linear accelerator example, the gantry, the treatment table, and collimator each have axes of rotation designed to intersect at a specific location in the middle of a treatment room, referred to as the isocenter, an origin of an interesting coordinate system of the treatment room, correspondingly referred to as the isocenter coordinate system. The isocenter coordinate system is nominally defined as horizontal (x-axis), vertical (z-axis), and co-linear with the axis of gantry rotation (y-axis). The isocenter of these three axis of interest is determined and used as a reference "point" to orient the target to the radiation treatment plan during treatment plan development and subsequent radiation delivery.

There are various methodologies of determining the location of this isocenter. For example, one methodology employs lasers directed at an apparatus having active or passive optical indicators to indicate the location of isocenter of the isocenter coordinate system to a camera or opti-electrical motion measurement system, such as, e.g., the camera system known as the Polaris®, by Northern Digital Inc., Ontario Canada. Also for example, described in co-pending application Ser. No. 11/005,643, by Scherch et al., entitled "System for Analyzing the Geometry of a Radiation Treatment Apparatus, Software and Related Methods," incorporated by reference, is a system, apparatus, software and methods that can measure the rotation of various components of the mechanical system of the radiation treatment apparatus or device to precisely define the isocenter of the isocenter coordinate system.

Regardless of which radiation generating apparatus or technique is used at the time of the diagnostic study to develop the radiation therapy treatment plan, in the delivery of either conformal radiation therapy treatments or static radiation therapy treatments, etc., the position of the target with respect to the radiation delivery apparatus is very important. As stated above, successful radiation therapy depends on accurately placing the radiation beam in the proper position upon the target. Thus, it is necessary to relate the position of the target at the time of the diagnostic study to how the target will be positioned at the time of the radiation therapy treatment. If the position of the target is not the same as it was at the time the treatment plan was determined, the dose of radiation may not be delivered to the correct location within the patient's body. Because patients are not always positioned properly on the treatment table of the radiation therapy device, which may be a linear accelerator or a cobalt unit, for example, and because organs of a patient may move within the patient from day to day, the target may not be positioned at the exact location where the radiation therapy plan has assumed it would be located.

Various measurements and tools have been developed to help ensure proper patient positioning including the lasers, described above, and optical distance indicators (ODIs). The distance of interest for ODIs generally used in most clinical practices, is the distance from the theoretical point source of the radiation beam to the surface of the patient's skin. The point source is termed theoretical because radiation beams are typically conical but are not produced by a point source, but rather a source having a finite size. This distance from the theoretical point source to the skin surface, typically either approximately 80 cm or 100 cm in a linear accelerator, for example, is generally referred to as either target-to-surface distance (TSD) or source-to-surface distance (SSD). When the isocenter is defined, the lasers are aligned to intersect in a cross-hair pattern at the isocenter. These lasers, as well as the ODI, are used to align the patient so that the target is located at isocenter.

The ODI projects from the head of the radiation delivery apparatus to the skin surface of the patient a set of cross hairs along with a scale that indicates the distance from the theoretical point source to the skin surface marked by the crosshairs. To make the measurement, the therapist visually finds the intersection of the crosshairs and the scale and records the scale reading at the intersection point. The scale marks are typically in increments of 0.5 cm and must be visually interpolated by the therapist. Recognized by the Applicant, however, is that the slope or gradient of the patients skin, e.g., at the neck or along a breast, often makes the scale hard, if not impossible, to read. Also recognized by the Applicant is that readings can only be taken when there is unobstructed line of sight between the head of the radiation delivery apparatus and the patient's skin, making it impossible to take direct measurements of positions underneath the patient, e.g., behind the patient's neck. Further, recognized by the Applicant is that the scale frequently requires calibration, resulting in an expenditure of valuable resources. Still further, with respect to the linear accelerator example, recognized by the Applicant is that the ODI cannot be used when, for example, a multivane intensity modulated collimator ("MIMiC") is mounted to the rotating gantry assembly.

Referencing the linear accelerator for illustrative purposes, the rotating gantry assembly and rotating treatment table assembly are heavy, slow pieces of machinery to manipulate. In order to take an ODI measurement, the patient must first be moved to directly beneath the rotating gantry head, and the rotating gantry assembly is rotated so that the ODI will shine on the selected measurement point. Additional readings would require additional movement of the treatment table assembly to reposition the patient and rotation of the gantry assembly. Recognized by the Applicant is that this process of moving the patient to directly beneath the rotating gantry head and the rotating gantry assembly so that the ODI will shine on the selected measurement point can be very time consuming. Further recognized is that for some radiation delivery procedures as many as a dozen points must be measured, each taking considerable time.

Because SSD is critical to predicting the dose delivered to the patient, and because typically a radiation treatment will deliver radiation from below the patient, it is necessary to get an accurate SSD at a measurement point where the ODI would be blocked by the rotating treatment table assembly or fixation equipment. ODI readings can only be taken where there is unobstructed line of sight between the head of the radiation delivery apparatus and the patient's skin, making it impossible to take direct measurements of positions underneath the patient, e.g., behind the patient's neck. Using the ODI to determine the SSD of visually obstructed points, the therapist takes a measurement on one side of the patient, measures the thickness of the patient with calipers typically having scales marked in increments of 0.25 cm, and then derives the SSD at the point on the opposite side of the patient. Recognized by the Applicant, however, is that there are no precise aids to ensure that the calipers are measuring points that are directly opposite each other along the central axis of the radiation beam. Recognized also is the inherent inaccuracy of having such potentially imprecise caliper scale increments.

A common procedure in the simulation room often used in conjunction with taking ODI measurements is to determine the appropriate radiation delivery path and radiation beam field size for a contoured body part, such as a patient's breast or chin. The goal of this setup is to find the appropriate location of isocenter and appropriate radiation beam field size and rotating gantry assembly angles that will result in positioning radiation beams having field edges that accurately follow a desired path. In a breast setup example, this entails determining a line tangent to the patient's chest. The tangent line is defined by marks placed by the physician on the patient's chest and side. Typically, the therapist manually constructs the setup by physically bending a solder wire along the patient's breast to capture the breast contour. Using a fluoroscopic procedure, the therapist or clinician detects the wire in live fluoroscopy images to determine the angle of the tangent line. The solder wire is in then physically moved off of the patient and onto graph paper, carefully, in order to preserve the contour, but generally without verification. The clinician then manually reconstructs the axial view of the patient contour and tangent line. From this axial view, the clinician geometrically constructs what gantry angles and radiation beam field size will produce the correct beam position. Recognized by the Applicant is that this type of contoured anatomy setup disadvantageously can take as long as 15 or 20 minutes and requires a fluoroscopy procedure which radiates the patient.

Correspondingly, recognized by the Applicant is the need for a system including tracker, program product, and related methods to facilitate and verify proper target alignment for radiation delivery that can provide an SSD for a surface of the patient having a substantial slope or gradient, that does not require individual calibration, and that can be used whether or not a MIMiC is mounted to the rotating gantry assembly of a linear accelerator when such radiation delivery apparatus is used. Also recognized is the need for a system that can quickly and efficiently deliver an SSD measurement for each of multiple surfaces of the patient without requiring repositioning of the patient in order to take each individual reading. Further, is the need for a system that can deliver actual SSD measurements for surfaces of the patient obstructed by various structures including the rotating table assembly of the linear accelerator when such radiation delivery apparatus is used. Still further, recognized is the need for a system that can provide accurate SSD and patient thickness measurements for measurement points opposite each other along the central axis of the radiation extending through the isocenter of the radiation delivery apparatus. Additionally, recognized is the need for a system that can accurately provide measurement data for a contoured portion of the patient's anatomy and that can help determine required radiation beam angles, beam field size, and location of the edges of the beam field.

SUMMARY OF THE INVENTION

In view of the foregoing, embodiments of the present invention advantageously provide a system including tracker, program product, and related methods to facilitate and verify proper target alignment for radiation delivery from a radiation delivery apparatus having a radiation emitter so that a treatment plan can be more accurately applied to a patient. Embodiments of the present invention provide a system including tracker, program product, and related methods that can provide a source-to-surface distance SSD between a theoretical point source of the radiation delivery emitter and a surface of the patient whether the surface is planer or whether the surface has a substantial slope or gradient. This SSD can be used to calibrate the actual patient's position with the patient's position according to the treatment plan, so that the treatment plan can be more accurately applied. Embodiments of the present invention provide a system including tracker, program product, and related methods that can quickly and efficiently deliver an SSD measurement for each of multiple surfaces of the patient without requiring repositioning of the patient in order to take each individual reading. This advantageously provides a significant time-saving advantage over the use of the optical distance indicators (ODIs).

Embodiments of the present invention further provide a system including tracker, program product, and related methods that can deliver actual SSD measurements for surfaces of the patient obstructed by various structures, including the rotating table assembly of the linear accelerator when such radiation delivery apparatus is used, and can provide accurate SSD and patient thickness measurements for measurement points opposite each other along the central axis of the radiation extending through the isocenter of the radiation delivery apparatus. Embodiments of the present invention also provide a system including tracker, program product, and related methods that can accurately provide measurement data for a contoured portion of the patient's anatomy and that can help determine required radiation beam angles, beam field size, and location of the edges of the beam field. Embodiments of the present invention still further provide a system including tracker, program product, and related methods that can be used whether or not a MIMiC is mounted to the rotating gantry assembly of a linear accelerator when such radiation delivery apparatus is used, and that preferably does not require individual calibration.

Generally, according to various embodiments of the present invention, the system includes an apparatus, preferably in the form of a radiation delivery apparatus which delivers radiation to a target in a patient. An application computer having memory associated therewith and a treatment plan stored in the memory can provide radiation delivery instructions to the radiation delivery apparatus. The radiation delivery apparatus has the radiation emitter positioned to emit a radiation beam having a central beam axis, a controller to control delivery of the radiation beam to the patient, and a rotating assembly having a rotational path in a distinct plane and an axis of rotation functioning to direct the radiation beam through a target of a patient in accordance with signals from the controller. The axis of rotation of the rotating assembly generally intersects with the beam axis at a three-dimensional coordinate, which defines the isocenter or origin of the isocenter coordinate system of the apparatus.

More specifically, embodiments of the present invention provide a system that includes a radiation delivery apparatus, typically in the form of a linear accelerator, positioned in communication with an application computer, to provide radiation treatment to the patient. The radiation delivery apparatus includes a radiation emitter positioned to emit a radiation beam having a theoretical point source and central beam axis, and typically includes a controller, responsive to the treatment delivery instructions, to control delivery of the radiation beam to the patient. According to the preferred embodiments of the present invention, the radiation delivery apparatus includes one or more rotating assemblies, each positioned to direct the radiation beam through a target of the patient, and each having a rotational path in a distinct plane and an axis of rotation. The axis of rotation of rotating assembly carrying the radiation emitter, defining an emitter carrying rotating assembly, intersects the central beam axis of the radiation emitter and/or the axis of rotation of another rotating assembly at a substantially same three-dimensional coordinate to define an isocenter of an isocenter coordinate system of the radiation delivery apparatus. The theoretical point source has a predetermined distance from the isocenter to define a source-to-axis distance.

Embodiments of the system also include one or more optically trackable bodies that can be positioned to be viewed/detected by a trackable body detector. Each trackable body has a trackable body origin positioned within a preselected coordinate system assigned thereto. Each optically trackable body also has assigned a trackable body reference point positioned with respect to the preselected coordinate system, and a plurality of separate and spaced-apart preferably optical indicators each connected at a separate preselected position thereon to indicate to a trackable body detector the separate three-dimensional coordinate positions of each indicator of the plurality of indicators, to thereby indicate a position of the trackable body reference point. The indicators are preferably in the form of passive indicators such as, for example, retro-reflective spheres or tape, which advantageously can provide upwards of a 180 degree reflective field of view and decrease inherent wiring requirements associated with active versions of such indicators.

Embodiments of the system also include a preferably optically trackable body detector or camera subsystem and a trackable body position determiner. The trackable body detector includes a detector body typically positioned spaced apart from the radiation apparatus and optically trackable body or bodies at a three-dimensional trackable body detector reference location. The trackable body detector includes a pair of separate and spaced apart optical receivers connected to the detector body, each having a field of view and being adapted to receive optical energy provided by each of a plurality of optical retro-reflective indicators when positioned in the field of view, to thereby detect a three-dimensional position of each of the plurality of preferably retro-reflective indicators when positioned simultaneously within the field of view of both of the optical receivers. In response to the energy emitted by the indicators, the trackable body detector produces a plurality of position signals representing such three-dimensional indicator positions. The trackable body detector also includes a pair of infrared illuminators, a first illuminator preferably positioned adjacent one of the pair of separate and spaced apart optical receivers and a second illuminator preferably positioned adjacent the other of the pair of separate and spaced apart optical receivers to selectively illuminate each of the plurality of optical retro-reflective indicators when positioned in the field of view of the respective adjacent optical receiver. This emission energizes the optical retro-reflective indicators within the field of view of the respective adjacent optical receiver.

The trackable body position determiner, in communication with the trackable body detector and responsive to the plurality of position signals produced by the trackable body detector, can determine or otherwise be provided the three-dimensional coordinate position of the isocenter and/or orientation of the isocenter coordinate system of the radiation delivery apparatus (in trackable body detector/camera space), and can determine a three-dimensional coordinate position of the trackable body reference point to thereby determine or verify proper target alignment for the radiation delivery apparatus. The trackable body position determiner includes memory associated therewith and position determiner software stored therein. The position determiner software or program product, responsive to the plurality of position signals from the trackable body detector, can determine the three-dimensional coordinate position of the trackable body reference point when positioned adjacent a surface of the patient defining a surface point position when a preselected number of the plurality of retro-reflective indicators are simultaneously positioned within the field of view of both of the optical receivers of the trackable body detector.

Functionally, according to an embodiment of the present invention, using a set of transform matrices, the trackable body position determiner can transform (magnitude, direction, and rotation) the isocenter coordinate system, the trackable body detector coordinate system, each predetermined or preselected optically trackable body reference coordinate system, and/or a separate reference fixture coordinate system. Having a chain of transformation matrices, the trackable body position determiner can thus transform the three-dimensional coordinate system definition of the isocenter and the three-dimensional coordinate system of the optically trackable body or bodies to the trackable body detector space and/or vice versa.

Embodiments of the present invention also include a target alignment analyzing computer and target alignment analyzing program product. According to an embodiment of the present invention, the target alignment analyzing computer is positioned in communication with the trackable body position determiner to determine proper target alignment for the radiation delivery apparatus. The target alignment analyzing computer has a processor, and memory coupled to the processor to store operating instructions, the three-dimensional coordinate position of the isocenter, and the source-to-axis distance of the radiation delivery apparatus, therein. The target alignment analyzing computer includes a display electrically coupled to the processor to display target alignment data.

The target alignment analyzing program product is stored in the memory of the target alignment analyzing computer to facilitate and verify proper target alignment for radiation delivery. The target alignment analyzing program product can include, alone or in combination, a source-to-surface distance determiner, an emitter carrier angle determiner, a central axis thickness determiner, a point-to-point distance determiner, a point collection table former, and a contour determiner.

The source-to-surface distance determiner is positioned to receive the three-dimensional coordinate position of isocenter, the source-to-axis distance, and a first surface point position on a first surface of the patient determined by the position determiner when coincident with the trackable body reference point. The source-to-surface determiner can determine a component of a distance within the plane of rotation of the emitter carrier rotating assembly between the theoretical point source and the first surface of the patient to define a first source-to-surface distance. Advantageously, this function can display to a user of the system the data provided by an optical distance indicator without the need to rotate the emitter carrier rotating assembly or position the target of the patient at the isocenter.

The emitter carrier angle determiner is positioned to receive the three-dimensional coordinate position of isocenter and the first surface point position, to determine an angle of rotation of the emitter carrier rotating assembly that positions or would position a path of the emitter central axis simultaneously through the first surface point position and the isocenter to define a first emitter carrier rotating assembly angle of rotation; and an off-plane distance determiner, positioned to receive a determined first surface point position, to determine an off-plane (offset) distance between the first surface point position and the plane of rotation for the emitter carrier rotating assembly. The off-plane distance provides the user of the system a distance required to move a target normal to the plane of rotation for the emitter carrier rotating assembly to position the target within the plane of rotation of the emitter carrier rotating assembly.

The central axis thickness determiner is positioned to receive the first surface point position and the first emitter carrier rotating assembly angle of rotation. In responsive to a three-dimensional coordinate position of the trackable body reference point of the optically trackable body determined by the trackable body position determiner, the central axis thickness determiner provides visual feedback to the user of the system to aid the user in positioning the trackable body reference point adjacent a second surface of the patient opposite the first surface along the emitter central axis path defining the first emitter carrier rotating assembly angle of rotation. A second surface point position located on the second surface is also determined. Having two point locations, i.e., the first and the second surface point positions, the central axis thickness determiner determines a patient thickness along the emitter central axis between the first and the second surface point positions.

The point-to-point distance determiner is positioned to receive a determined first surface point position, and in response to a three-dimensional coordinate position of the trackable body reference point of the trackable body determined by the trackable body position determiner, can determine a distance between the first surface point position and the three-dimensional coordinate position of the trackable body reference point. Such patient surface relative positioning data aids to the user of the system verify proper patient positioning.

The point collection table former is positioned to receive a list of a plurality of pre-defined surface points. In response to a user sequentially positioning the trackable body reference point of the optically trackable body adjacent each of a plurality of surface point locations corresponding to the plurality of pre-defined surface points, the point collection table former can form a surface locations table including, for each of the plurality of pre-defined surface points, either a surface point position or a source-to-surface distance, to thereby ensure proper patient positioning.

The contour determiner is positioned to determine two three-dimensional coordinate positions of the preselected trackable body reference point when adjacent a corresponding first and second selected separate and spaced apart patient surface point positions defining a first setup surface point position and a second setup surface point position, respectively. In response to determining the first setup and the second setup surface point positions, the contour determiner can determine a point-to-point line between the first setup and the second setup surface point positions, to thereby determine a radiation beam field edge boundary. The contour determiner is also positioned to receive a plurality of surface point positions provided by the trackable body position determiner. In response to user positioning of the trackable body reference point of the optically trackable body along a contour of a contoured human body part, the contour determiner can determine the contour of the contoured human body part. Advantageously, such data allows the contour determiner to determine an optimum emitter angle and beam width of the radiation delivery apparatus to enhance delivery of radiation to the contoured body part.

Embodiments of the present invention also include a tracker viewable by the trackable body detector. According to an embodiment of the present invention, a tracker includes an optically trackable body having a proximal end portion, a distal end portion, and a medial body portion extending therebetween. The distal end portion includes an annular recess and a trackable body reference point associated therewith and assigned thereto. A plurality of separate and spaced-apart preferably optical indicators are connected at a separate preselected position of the medial body portion of the optically trackable body and are positioned such that they have a preselected segment length between each pair combination so that a trackable body detector/determiner can identify the specific tracker currently being viewed. The optical indicators are also adapted to be tracked by the trackable body detector/determiner combination to indicate a position of the trackable body reference point. A spherical body is rotatably positioned within the annular recess adjacent the trackable body reference point, and is adapted to contact a surface of the patient and to roll when manipulated along the surface of the patient to enhance movement of the optically trackable body when in contact with the surface of the patient. Advantageously, this helps prevent inadvertent deformation of a contoured patient body structure when in contact with the tracker.

According to another embodiment of the present invention, a tracker includes an optically trackable body having a proximal end portion, a distal end portion, and a medial body portion extending therebetween with the distal end portion having a trackable body reference point associated therewith. The tracker also includes a plurality of separate and spaced-apart preferably optical indicators connected at a separate preselected position of the medial body portion of the optically trackable body and positioned such that they have a preselected segment length between each pair combination so that a trackable body detector/determiner can identify the specific tracker currently being viewed. The indicators are also adapted to be tracked by the trackable body detector/determiner combination to indicate a position of the trackable body reference point. The tracker also includes a switch adapted to be manipulated by the user to mask at least one of the plurality of optical indicators to thereby disable provision of position data for the trackable body reference point, and adapted to be manipulated by the user to unmask the at least one of the plurality of indicators to thereby enable provision of position data for the trackable body reference point. Advantageously, such type of switch, along with other functional equivalents, can be used to provide a trackable body determiner and/or target alignment analyzing computer indicia that the user has positioned the trackable body reference point at a desired location.

According to another embodiment of the present invention, a tracker includes an optically trackable body having a proximal end portion, a distal end portion having a trackable body reference point associated therewith, and a medial body portion extending therebetween. Similar to the above described trackers, this tracker also includes a plurality of separate and spaced-apart preferably optical indicators connected at a separate preselected position of the medial body portion of the optically trackable body and positioned such that they have a preselected segment length between each pair combination so that a trackable body detector/determiner can identify the specific tracker currently being viewed. According to an embodiment of the tracker, the medial body portion, however, has a width substantially greater than depth and has an obtuse shape (spatula or spread V-type shape). Advantageously, this body shape enhances positioning the optically trackable body, particularly, the trackable reference point, between a lower surface of a patient and a substantially flat upper surface of a treatment table with little or no disruption to the positioning of the patient.

Embodiments of the present invention also include methods to facilitate and verify proper target alignment for radiation delivery so that a treatment plan can be more accurately applied to a patient. For example, according to an embodiment of the present invention, a method can include steps necessary to determine a source-to-surface distance between theoretical point source of the radiation emitter for the apparatus and a surface point position of a patient along a central axis of the radiation emitter using a trackable body to identify such surface point position. The method can include receiving a predetermined three-dimensional coordinate position of isocenter of an apparatus carrying a radiation emitter having a central axis and receiving a predetermined distance from the isocenter to the theoretical point source of the radiation emitter for the apparatus defining a source-to-axis distance. The method can also include providing an optically trackable body having a preselected trackable body reference point and having a plurality of separate and spaced-apart optical indicators each connected thereto at a separate preselected position; positioning the trackable body reference point adjacent a selected surface of a patient defining a patient surface; tracking a subset of the plurality of separate and spaced-apart optical indicators to determine a three-dimensional coordinate position of the trackable body reference point; and determining, responsive to the tracking, the three-dimensional coordinate position of the trackable body reference point when adjacent the patient surface defining a surface point position. The method can also include determining, responsive to determining the surface point position and receiving the source-to-axis distance, a component of a distance between the theoretical point source and the surface point position defining a source-to-surface distance; and displaying the source-to-surface distance of to the user preferably on a computer display.

According to an embodiment of the present invention, a method can include steps necessary to determine a thickness of a patient between two opposite surface points of the patient along the central axis of the radiation emitter when delivering the radiation at a predetermined angle, defining a central axis thickness. The method can also include providing an optically trackable body having a preselected trackable body reference point and having a plurality of separate and spaced-apart optical indicators each connected thereto at a separate preselected position. The method can include selecting and determining a first surface point position and the source-to-surface distance to such point according to the method, such as, for example, that described above; and determining, responsive to determining the first surface point position, an angle of rotation of the emitter carrier rotating assembly that positions the central axis of the emitter simultaneously through the first surface point position and the isocenter, which defines a first emitter rotating assembly angle of rotation. The method also includes providing to a user, responsive to tracking the position of the trackable body reference point, visual feedback to aid the user in positioning the trackable reference body reference point adjacent a second surface point position on a second opposite patient surface of the patient located along the emitter rotating assembly angle of rotation; and determining, responsive to the visual feedback and the user positioning of the trackable reference body reference point adjacent the second patient surface of the patient, a three-dimensional coordinate position of the second surface point position. The method can further include determining, responsive to determining the second surface point position and receiving the source-to-axis distance, a component of a distance between the theoretical point source and the second surface point position to define a second source-to-surface distance; determining, either responsive to receiving the source-to-axis distance and determining the first and the second source-to-surface distances, or alternatively responsive to determining the first and the second surface point positions, a patient thickness of the patient along the emitter central axis between the first and the second surface point positions to define a central axis thickness; and displaying the central axis thickness to the user, to thereby facilitate and verify proper target alignment According to an embodiment of the present invention, a method can include steps necessary to determine a thickness of a patient of between two opposite surface points of the patient along a preselected, preferably vertical angle. The method can also include providing an optically trackable body having a preselected trackable body reference point and having a plurality of separate and spaced-apart optical indicators each connected thereto at a separate preselected position. The method can also include selecting and determining a first surface point position and the source-to-surface distance to such point according to the method, such as, for example, that described above; and providing a preselected emitter rotating assembly angle of rotation. The method can also include providing to a user, responsive to tracking the position of a trackable body reference point, visual feedback to aid the user in positioning the trackable reference body reference point adjacent a second surface point position on a second patient surface located opposite the first patient surface along the preselected emitter rotating assembly angle of rotation; and determining, responsive to the visual feedback and the user positioning of the trackable reference body reference point adjacent the second patient surface of the patient, a three-dimensional coordinate position of the second surface point position. The method can also include determining, responsive to determining the second surface point position and the source-to-axis distance, a component of a distance between the theoretical point source of the radiation emitter and the second surface point position to define a second source-to-surface distance. The method can further include determining, either responsive to receiving the source-to-axis distance and determining the first and the second source-to-surface distances, or responsive to determining the first and the second surface point positions, a patient thickness of the patient along an axis between the first and the second surface point positions; and displaying the patient thickness to the user, to thereby facilitate and verify proper target alignment.

According to an embodiment of the present invention, a method can include steps necessary to determine a table of three-dimensional coordinate point locations for each of the plurality of surface point positions of a patient. The method includes providing a preferably optically trackable body having a plurality of separate and spaced-apart optical indicators each connected thereto at a separate preselected position and having a preselected trackable body reference point. The method also includes positioning the trackable body reference point adjacent a plurality of selected surface of a patient each defining a patient surface; tracking the position of a subset of the plurality of separate and spaced-apart optical indicators when visible to the optically trackable body detector, to determine a plurality of positions of the preselected trackable body reference point; and determining, responsive to the tracking, the plurality of positions of the preselected trackable body reference point when adjacent a corresponding plurality of separate and spaced apart patient surfaces located at pre-selected points to define a respective plurality of surface point positions. The method further includes forming, responsive to the plurality of surface point positions, a point collection table including a three-dimensional coordinate point location for each of the plurality of surface point positions; and displaying the point collection table to a user, to thereby ensure proper patient positioning.

According to an embodiment of the present invention, a method can include steps necessary to determine a point-to-point distance between first surface point position and a current position of a preselected trackable body reference point associated with a trackable body. The method includes providing a trackable body having a plurality of separate and spaced-apart optical indicators each connected thereto at a separate preselected position and having a preselected trackable body reference point. The method also includes tracking the position of a subset of the plurality of separate and spaced-apart optical indicators, to determine a plurality of positions of the preselected trackable body reference point; positioning the trackable body reference point adjacent a selected surface of a patient defining a first patient surface; and determining, responsive to the tracking and the positioning, a three-dimensional coordinate position of the trackable body reference point when adjacent the patient surface defining a first surface point position. The method also includes determining, responsive to the tracking and the determining of the first surface point position, a point-to-point distance between first surface point position and a current position of the preselected trackable body reference point; and displaying the point-to-point distance, to thereby facilitate and verify proper target alignment.

According to an embodiment of the present invention, a method can include steps necessary to analyze a contour of the contoured surface of the patient. The method includes providing a preferably optically trackable body having a plurality of separate and spaced-apart optical indicators each connected thereto at a separate preselected position and having a preselected trackable body reference point. The method also includes positioning the trackable body reference point adjacent a selected contoured surface of a contoured body part of a patient; tracking the position of a subset of the plurality of separate and spaced-apart optical indicators to determine a plurality of three-dimensional coordinate positions of the preselected trackable body reference point; and determining, responsive to the tracking, the plurality of three-dimensional coordinate positions of the preselected trackable body reference point when translated adjacent the contoured surface of the patient to define a respective plurality of surface point positions. The method also includes forming, responsive to determining the plurality of surface point positions, a representation of the contour of the contoured surface of the patient. The method can also include determining, responsive to the tracking, two three-dimensional coordinate positions of the preselected trackable body reference point when adjacent a corresponding two selected separate and spaced apart patient surface point positions defining a first setup surface point position and a second setup surface point position, respectively; and forming, responsive to determining the first setup and the second setup surface point positions, a point-to-point line between the first setup and the second setup surface point positions, to thereby determine a radiation beam field edge boundary. Advantageously, such measurements are useful in determining an optimum emitter angle and beam width of a radiation delivery apparatus to deliver radiation to the contoured body part.

Embodiments of the present invention also include a computer readable medium to facilitate and verify proper target alignment for radiation delivery so that a treatment plan can be more accurately applied to a patient. For example, according to an embodiment of the present invention, a computer readable medium includes a set of instructions that, when executed by a computer, cause the computer to determine a source-to-surface distance between the theoretical point source of a radiation emitter for the apparatus and a surface point position of a patient along a central axis of the radiation emitter using a trackable body to identify such surface point position. The instructions can include those to perform the operations of: tracking a position of a subset of a plurality of separate and spaced-apart optical indicators positioned on an optically trackable body to determine a three-dimensional coordinate position of a trackable body reference point on the optically trackable body; determining, responsive to the tracking, the three-dimensional coordinate position of the trackable body reference point when adjacent the patient surface defining a surface point position; and determining, responsive to determining the surface point position, a component of a distance between the theoretical point source of the radiation emitter for the apparatus and the surface point position defining the source-to-surface distance.

According to an embodiment of the present invention, a computer readable medium includes a set of instructions that, when executed by the computer, cause the computer to determine a thickness of a patient between two opposite surface points of the patient along the central axis of a radiation emitter of a radiation delivery apparatus when delivering radiation at a predetermined angle, the thickness defining a central axis thickness. The instructions can include those to perform the operations of: determining a first surface point position as, for example, described above; determining, responsive to determining the first surface point position, an emitter rotating assembly angle of rotation of an emitter carrier rotating assembly of the radiation delivery apparatus that positions the central axis of the emitter simultaneously through the first surface point position and target when at an isocenter of a radiation delivery apparatus. The instructions can also include those to perform the operations of: forming, responsive to tracking the position of the trackable body reference point, a representation of a location of the trackable body reference point relative to a second surface point position on a second opposite patient surface of the patient located along the emitter rotating assembly angle of rotation, to thereby aid the user in positioning the trackable reference body reference point adjacent the second surface point position; and determining, responsive to the user positioning of the trackable reference body reference point adjacent the second patient surface of the patient, a three-dimensional coordinate position of the second surface point position. The instructions can also include those to perform the operations of: determining, responsive to determining the second surface point position, a component of a distance between the theoretical point source and the second surface point position to define a second source-to-surface distance; and determining, responsive to the determining of the first and the second source-to-surface distances, or responsive to determining the first and the second surface point positions, a patient central axis thickness of the patient along the emitter central axis between the first and the second surface point positions, to thereby facilitate and verify proper target alignment.

According to an embodiment of the present invention, a computer readable medium includes a set of instructions that, when executed by the computer, cause the computer to determine a thickness of a patient of between two opposite surface points of the patient along a preselected, preferably vertical angle. The instructions can include those to perform the operations of: determining a first surface point position and the source-to-surface distance to such point as, for example, described above; and providing or selecting a preferably vertical emitter rotating assembly angle of rotation. The instructions can also include those to perform the operations of: providing to a user, responsive to tracking the position of the trackable body reference point, visual feedback to aid the user in positioning the trackable reference body reference point adjacent a second surface point position on a second patient surface located opposite the first patient surface along the preselected emitter rotating assembly angle of rotation; and determining, responsive to the user positioning of the trackable reference body reference point adjacent the second patient surface of the patient, a three-dimensional coordinate position of the second surface point position. The instructions can also include those to perform the operations of: determining, responsive to the determining of the second surface point position, a component of a distance within a plane of rotation of the emitter carrier rotating assembly between the theoretical point source of the radiation emitter and the second surface point position to define a second source-to-surface distance; and determining, either responsive to the determining of the first and the second source-to-surface distances, or responsive to the determining of the first and the second surface point positions, a patient thickness of the patient along an axis between the first and the second surface point positions, to thereby facilitate and verify proper target alignment.

According to an embodiment of the present invention, a computer readable medium includes a set of instructions that, when executed by the computer, cause the computer to form a table of three-dimensional coordinate point location for each of the plurality of surface point positions of a patient. The instructions can include those to perform the operations of: tracking a position of a subset of a plurality of separate and spaced-apart optical indicators positioned on an optically trackable body, to determine a plurality of positions of a preselected trackable body reference point associated with the optically trackable body; and determining, responsive to the tracking, the plurality of positions of the preselected trackable body reference point when adjacent a corresponding plurality of separate and spaced apart patient surfaces located at pre-selected points to define a respective plurality of surface point positions. The instructions can also include those to perform the operations of: forming, responsive to determining the plurality of surface point positions, a point collection table including a three-dimensional coordinate point location for each of the plurality of surface point positions; and providing data to a video display to display the point collection table to a user, to thereby ensure proper patient positioning.

According to an embodiment of the present invention, a computer readable medium includes a set of instructions that, when executed by the computer, cause the computer to determine a point-to-point distance between a first surface point position of a patient and a current position of the preselected trackable body reference point of a trackable body. The instructions can include those to perform the operations of: tracking a position of a subset of a plurality of separate and spaced-apart optical indicators positioned on an optically trackable body, to determine a plurality of positions of a preselected trackable body reference point associated with the optically trackable body; and determining, responsive to the tracking and user positioning of the optically trackable body, a three-dimensional coordinate position of the trackable body reference point when adjacent the patient surface defining a first surface point position. The instructions can also include those to perform the operations of: determining, responsive to the tracking and the determining of the first surface point position, a point-to-point distance between the first surface point position and a current position of the preselected trackable body reference point; and providing data to a video display to display the point-to-point distance to the user, to thereby facilitate and verify proper target alignment.

According to an embodiment of the present invention, a computer readable medium includes a set of instructions that, when executed by the computer, cause the computer to analyze a contour of the contoured surface of the patient using a trackable body. The instructions can include those to perform the operations of: tracking a position of a subset of a plurality of separate and spaced-apart optical indicators positioned on an optically trackable body, to determine a plurality of three-dimensional coordinate positions of a preselected trackable body reference point associated with the optically trackable body; and determining, responsive to the tracking, the plurality of three-dimensional coordinate positions of the preselected trackable body reference point when translated adjacent a contoured surface of the patient to define a respective plurality of surface point positions. Instructions can also include those to perform the operations of: forming, responsive to determining the plurality of surface point positions, a representation of the contour of the contoured surface of the patient. The instructions can also include those to perform the operations of: determining, responsive to the tracking, two three-dimensional coordinate positions of the preselected trackable body reference point when adjacent a corresponding two selected separate and spaced apart patient surface point positions defining a first setup surface point position and a second setup surface point position, respectively; and forming, responsive to determining the first setup and the second setup surface point positions, a point-to-point line between the first setup and the second setup surface point positions, to thereby determine a radiation beam field edge boundary. The instructions can also include those to perform the operation of: determining, responsive to determining the contour and radiation beam field edge boundary, an optimum emitter angle and beam width of a radiation delivery apparatus to deliver radiation to the contoured body part.

Advantageously, embodiments of the present invention utilize a pre-existing camera tracking or other form of preferably optical trackable body tracking system or apparatus prepositioned in a radiation delivery or simulation room and calibrated to a reference coordinate system, e.g., the isocenter coordinate system, such as those typically used in the optically tracking ultrasound equipment. Advantageously, embodiments of the optically trackable body and target alignment analyzing program product can utilize such optical tracking systems with little modification. The presence of such trackable body tracking system or apparatus adjacent the emitter carrying rotating assembly, e.g. rotating gantry assembly in the linear accelerator, allows the various measurements to be performed without having to manipulate such assembly. Advantageously, software/program product guidance can help ensure that the appropriate measurements are taken and that the end result is recorded without error. In addition, software/program product modeling can significantly streamline the process, greatly increasing throughput, thus significantly improving efficiency and potential revenue. That is, tasks which historically have taken 15 minutes or more can be shortened to less than 1 minute.

Advantageously, embodiments of the present invention utilize one or more tracking devices (trackable bodies) which can be used to collect point measurements. Advantageously, these trackable bodies can have a useful pointer shape or extension to provide a well-defined trackable body reference point used to identify a finite point on the patient's skin surface. One example of such tracker includes a tracker with a pointed end. Advantageously, some of the embodiments of the system include a tracker structurally adapted so that the measurement point can be easily slid underneath a patient in order to identify and contact a downwardly oriented skin surface point. Such various tracker designs, among others, advantageously enhance specific user processes, and thus, can differ accordingly. For example, advantageously embodiments of the present invention can include a tracker structurally configured to capture a contour of a contoured anatomical feature. Such tracker can include a roller tip, laser, or other low or no friction contact portion to allow positioning the tracker along the contour without excessively deforming such contour.

Advantageously, embodiments of the tracker can include a mechanical or electronic switch mechanism designed into them to allow the therapist to indicate to the software/program product when an action is to be taken. Advantageously, for passive indicators, switching can be accomplished by masking or unmasking a preselected one or more of the passive indicators. Advantageously, software/program product inherent with the optical trackable body tracking system or apparatus can be used to report the state of the preselected indicator or indicators as the switch state.

Advantageously, embodiments of the present invention can be implemented in a number of ways depending upon the desired complexity (or non-complexity) of the user interface. For example, each of the target analyzing program product functions can be implemented to have a single purpose and specifically limited so that such function can be controlled using a single simple switch as input. Advantageously, such implementation easily allows a display screen mounted on the wall or otherwise out of the way of the clinician, with only the tracker in close proximity to the patient. Other more sophisticated applications utilizing multiple functions are enhanced through use of a more sophisticated user interface such as, for example, use of a small cart that can be wheeled to and away from the patient to provide ready access to multiple trackers/tools and/or a more sophisticated user interface, e.g., an adjacent multi-function display or computer input device. Further, advantageously, embodiments of the present invention can allow for real-time individual tailoring such that more sophisticated applications to use the cart, but simple quick applications to be displayed on a wall mounted screen.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 1 is a perspective view of a system to facilitate and verify proper target alignment for radiation delivery according to an embodiment of the present invention;

FIG. 4 is a perspective view of a trackable body used to facilitate and verify proper target alignment for radiation delivery according to an embodiment of the present invention;

FIG. 5 is a perspective view of a trackable body used to facilitate and verify proper target alignment for radiation delivery according to an embodiment of the present invention;

FIGS. 6A-B is a perspective view of the trackable body of FIG. 4 illustrating a manual switch in the open and closed positions according to an embodiment of the present invention;

FIGS. 7A-B is a perspective view of the trackable body of FIG. 5 illustrating a manual switch in the open and closed positions according to an embodiment of the present invention;

FIG. 8 is a perspective view of a trackable body used to facilitate and verify proper target alignment for radiation delivery according to an embodiment of the present invention;

FIG. 9A is a perspective view of a trackable body used to facilitate and verify proper target alignment for radiation delivery according to an embodiment of the present invention;

FIG. 9B is a sectional view of a trackable body used to facilitate and verify proper target alignment for radiation delivery according to an embodiment of the present invention;

FIG. 15 is a perspective view of a portion of a system to facilitate and verify proper target alignment for radiation delivery according to an embodiment of the present invention;

FIG. 16 is a schematic diagram of a graphical user interface for a system to facilitate and verify proper target alignment for radiation delivery according to an embodiment of the present invention;

FIG. 17 is a perspective view of a patient to illustrating beam field divergence according to an embodiment of the present invention;

DETAILED DESCRIPTION

Figure 3:
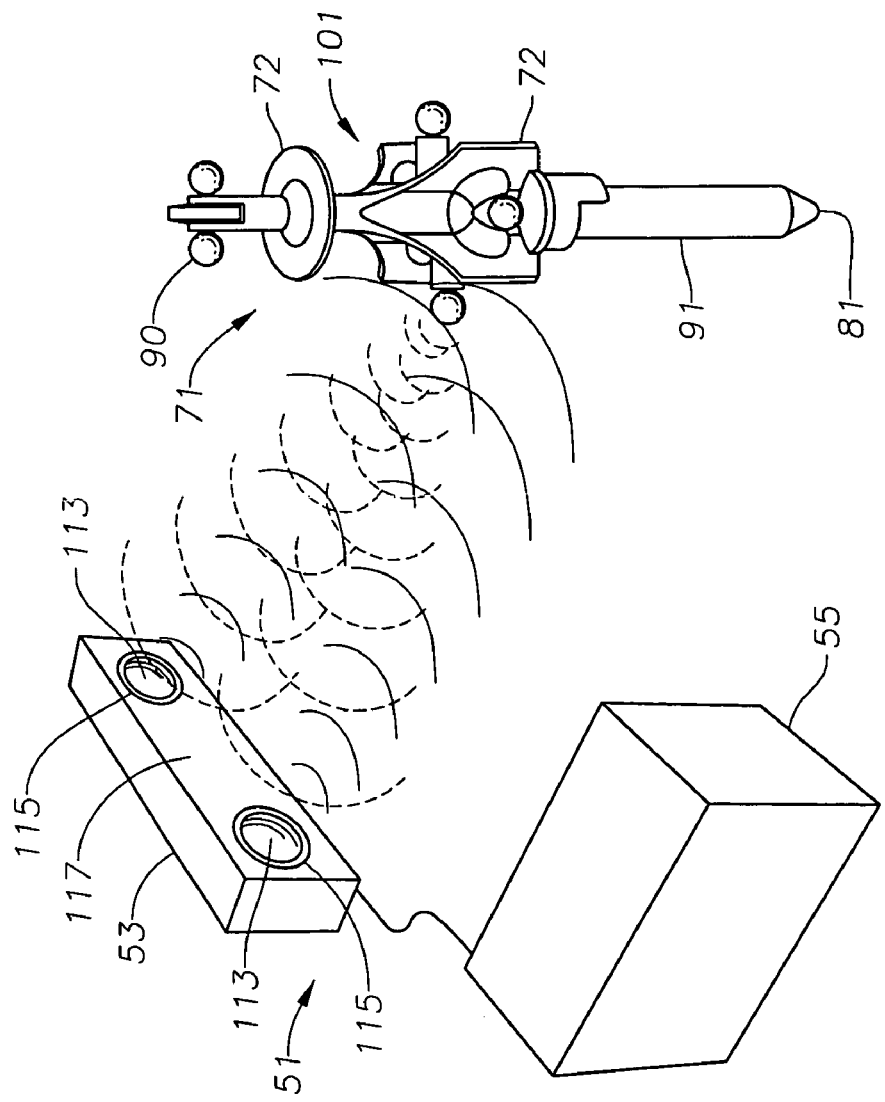
FIG. 3 is a perspective view of a trackable body and apparatus to track the trackable body used to facilitate and verify proper target alignment for radiation delivery according to an embodiment of the present invention.
Figure 2:
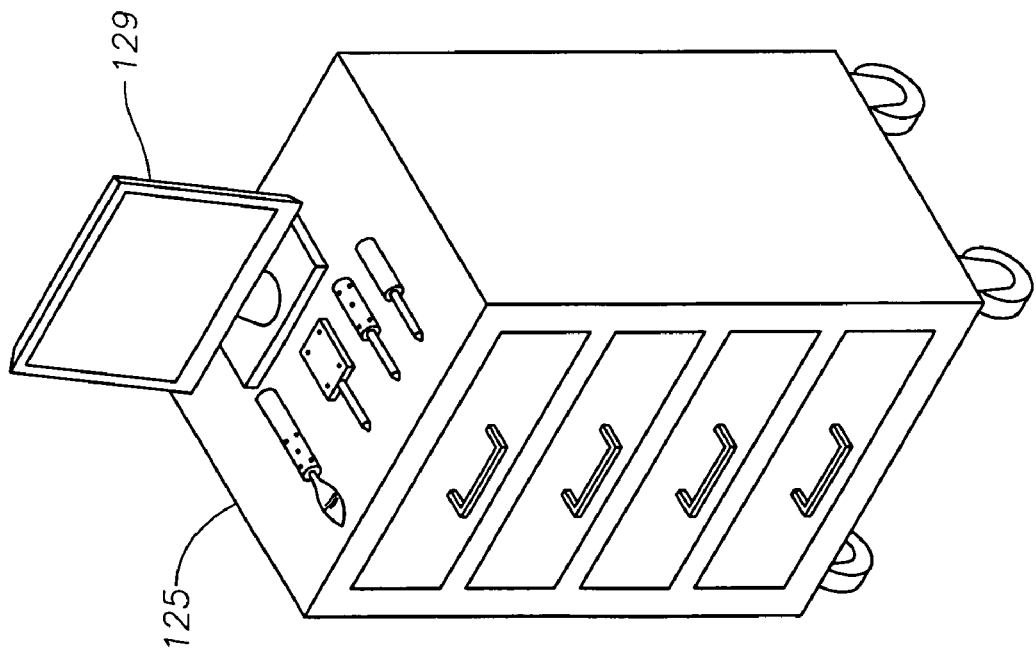
FIG. 2 is a perspective view of a portion of a system to facilitate and verify proper target alignment for radiation delivery according to an embodiment of the present invention.

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Successful therapy treatments, such as, for example, radiation therapy, rely on the ability to accurately locate and define a radiation beam. The spatial position of the radiation beam is defined by the physical geometry of the treatment apparatus. The geometry of rotating assemblies of the treatment apparatus define a coordinate system of the treatment apparatus, which is used by a therapist to determine the position of the radiation beam and the positioning of the patient. The origin of this coordinate system is referred to as "isocenter" and this coordinate system is referred to as the "isocenter coordinate system." Many treatment systems rely on the accuracy of a calibrated tracking system to reliably indicate the isocenter coordinate system during radiation delivery. Further, preexisting camera tracking or other form of optical and magnetic trackable body tracking systems or apparatus, such as those typically used in the tracking ultrasound equipment, are or can be easily prepositioned in a radiation delivery or simulation room and calibrated to a reference coordinate system, e.g., the isocenter coordinate system.

In conformal radiation therapy treatments, static radiation therapy treatments, or other therapy using a radiation emitter, for the position of the target with respect to the radiation delivery apparatus is also very important. Successful radiation therapy depends on accurately placing the radiation beam in the proper position upon the target. Thus, it is necessary to relate the position of the target at the time of the diagnostic study/treatment plan development to how the target will be positioned at the time of delivery of the radiation therapy treatment. If the position of the target is not the same as it was at the time the treatment plan was determined, the dose of radiation may not be delivered to the correct location within the patient's body, possibly undertreating the target and damaging surrounding tissue. Because patients are not always positioned properly on the treatment table of the radiation delivery device, which may be a linear accelerator, cobalt, or other unit, and because organs of a patient may move within the patient from day to day, the target may not be positioned at the exact location where the radiation treatment plan has assumed it would be located.

Clinical procedures for performing such position related verification traditionally take a significant amount of time, make use of inconvenient tools, and are error prone. Such clinical procedures can be made faster, simpler, and less error prone by using an optically or magnetically based tracking system installed in, e.g., the radiation delivery or simulation room. These procedures include source-to-surface (skin) distance (SSD)/target-to-surface (skin) distance (TSD) measurements, thickness (separation) measurements, breast setup measurements, and other common measurements. Traditional methods for performing these tasks require manipulation of the radiation emitting rotating assembly (rotating gantry assembly in a linear accelerator), projecting a combination of analog scales and crosshairs using an optical distance indicator (ODI) connected to or adjacent the radiation emitter, subjective determination of the analog scales, manual transcription of contour lines, use of measurement tools, and additional radiation delivery to the patient.

Thus, advantageously, as illustrated in FIGS. 1-29, embodiments of the present invention provide a system including tracker, program product, and methods to facilitate and verify proper target alignment for radiation delivery so that a treatment plan can be more accurately applied to a patient. As perhaps best shown in FIG. 1, generally, various embodiments of a system 30 can include a radiation delivery apparatus having one or more rotating assemblies, such as, for example, a linear accelerator 31, which delivers radiation to a target T in a patient P. The following discussion will refer to linear accelerator 31 shown in FIG. 1 for illustrative purposes, only. Other radiation delivery apparatus known to those skilled in the art, including but not limited to a magnetic resonance imaging ("MRI") or computerized tomography ("CT") scan device, are also within the scope of the present invention.

The linear accelerator 31 preferably includes a rotating collimator assembly 33 having a theoretical point source and central beam axis and which functions as a radiation emitter that can shape the profile of the radiation beam; a rotating gantry assembly 35 which functions as an emitter carrying rotating assembly; and a rotating treatment table assembly 37. Each rotating assembly has a rotational path in a distinct plane and an axis of rotation. Each rotating assembly is also preferably controlled by a controller 39. The axis of rotation of the rotating gantry assembly 35 intersects with the beam axis of the rotating collimator assembly 33 at a three-dimensional coordinate position which defines the isocenter 40 or origin of the isocenter coordinate system of the linear accelerator 31.

The system 30 also includes an application computer 41 having memory 43 and a treatment plan stored in the memory 43, which provides treatment delivery instructions to the controller 39. The system 30 further includes an apparatus 51 to track a trackable body which includes a trackable body detector 53 provided to detect a position of indicators associated with a trackable body, and a trackable body position determiner 55, in communication with the trackable body detector 53, to determine the position a trackable body and/or reference point thereon. The system can also include a target alignment analyzing computer 61 including target alignment analyzing program product 63 which can provide for the various measurements, described above.

More specifically, according to embodiments of the present invention, the system 30 includes a radiation apparatus, such as a linear accelerator 31, in communication with an application computer 41, to provide radiation delivery to a target T in a patient P. The linear accelerator 31 has a plurality of rotating assemblies including a rotating gantry assembly 35 having a gantry axis of rotation G, a gantry rotational outer circumference (not shown), and a gantry head 60 positioned adjacent the gantry rotational outer circumference to direct a radiation beam toward the gantry axis of rotation G. A rotating patient treatment table assembly 37 having a treatment table axis of rotation TT is positioned adjacent the gantry assembly 35 to move the position of the target T of the patient P with respect to the isocenter 40 before and/or during radiation delivery. A rotating collimator assembly 33 is connected to the gantry head 60 and has a collimator axis of rotation positioned coaxially with the central beam axis C of the radiation beam directed by the gantry head 60 to shape the profile of the radiation beam. The rotating collimator assembly 33 also has a theoretical point source (TPS) for the radiation beam typically existing at a predetermined distance from the isocenter 40 of the linear accelerator 31 or axis G of the rotating gantry assembly 35 to define a source-to-axis distance (SAD). In the linear accelerator example, this distance is typically 80 cm or 100 cm.

Embodiments of the system 30 also include a subsystem or apparatus to track the trackable body, hereinafter referred to as a "trackable body tracking apparatus" 51, described in detail later. The position of a trackable object or tool is typically defined by three translation parameters (x, y, z) and three rotation parameters (pitch, roll, yaw) corresponding to six degrees of freedom. The translation parameters (x, y, z—not shown) indicate three-dimensional position, e.g. forward and back (y-axis), left and right (x-axis), up and down (z-axis), and three rotation parameters (pitch, roll, yaw) indicate orientation of the tool or object, e.g. rotation about the x-axis (pitch), rotation about the y-axis (roll), and rotation about to the z-axis (yaw). Various trackable body tracking apparatus, such as those used in optically tracking ultrasound equipment, are available for determining the spatial position and orientation of an object in free space. One such apparatus known as the Polaris®, by Northern Digital Inc., Ontario Canada, includes a computer system that tracks a tool or probe having optical emitters or indicators, while an operator repositions the tool or probe. The tool or probe can have a fixed length. Thus, contacting an object or pointer with the end of the tool can provide a reference point for indicating a position of an object of points of interest.

The indicators or emitters can be either active or passive. Active emitters, however, are often subject to wiring interference caused by the necessity to provide power to each of the respective emitters. Wiring generally supplies encoded signals to each of the emitters which function as markers and which are either activated in sequence or provide sonic, optical, or radio frequency signals on different frequencies. Unlike active emitters, passive emitters are generally in the form of a reflector and do not necessarily suffer the same wiring limitations. Passive emitters are becoming the preferred type of emitter as they can be installed on virtually any type of object or tool to provide a relative location of the object or tool or a portion, thereof. Passive emitters supply their signal via active radiating external emitters positioned within view of the passive emitters. The signal from the active emitters is reflected by the passive emitters. The circuitry involved with passive emitters is generally less complicated as they tend to function simultaneously, each emitting or reflecting the same type of signal. Both active and passive emission techniques typically operate by projecting a geometric representation or extension of the object or tool formed by the emitters onto the field of view of a pair of spaced sensors. Various implementations of sensors have been used, the most popular being the use of two cameras elements positioned spaced apart a known distance and angled in the general direction of the object or tool such that the three-dimensional position of the object or tool can be obtained by triangulation from the positions of the emitters.

Correspondingly, embodiments of the system 30 can include one or more optically trackable bodies 71, 73, 75, 77, 79, such as, for example, those illustrated in FIGS. 3-9B, that can be positioned to be viewed/detected by a trackable body detector 53. Each trackable body 71, 73, 75, 77, 79, has a trackable body origin (not shown) positioned within a preselected coordinate system assigned thereto. Each optically trackable body also has assigned a respective trackable body reference point 81, 83, 85, 87, 89, positioned with respect to the preselected coordinate system, and a plurality of separate and spaced-apart preferably optical indicators 90 each connected at a separate preselected position thereon to indicate to a trackable body detector 53 the separate three-dimensional coordinate positions of each indicator to thereby indicate a position of the respective trackable body reference points 81, 83, 85, 87, 89, generally located at a distal most portion of the optically trackable bodies 71, 73, 75, 77, 79, or the distal most portion of an extension member 91, 93, 95, 97, 99, connected to or otherwise interfaced with a main body portion 101, 103, 105, 107, 109, of the optically trackable bodies 71, 73, 75, 77, 79. Trackable body reference points 81, 83, 85, 87, 89, can be positioned to contact a surface point position $S_1$-$S_n$ (see, e.g., FIGS. 11, 13A-B, 15, 17, 18, 20, and 22) of a patient P to identify the three-dimensional coordinate position of that surface point positions $S_1$-$S_n$.

According to an embodiment of the one or more of the illustrated optically trackable bodies, the indicators 90 generally have a preselected segment length between each pair combination of the indicators such that a plurality of combinations of at least three of the plurality of indicators form a plurality of geometric figures. Each of the plurality of indicators 90 are adapted to be optically tracked over a subset of possible orientations to provide three-dimensional positional data and angular orientation data of the optically trackable body and any extensions thereof. The indicators 90 are preferably in the form of passive indicators such as, for example, retro-reflective spheres (see FIG. 3) or retro-reflective tape (see FIGS. 4-9B), which advantageously can provide upwards of a 180 degree reflective field of view and decrease inherent wiring requirements associated with active versions of such indicators. Note, variations in body shape, selection of type of indicator, and extension design for the example trackable bodies shown in FIGS. 3-9B are within the scope of the present invention. These particular trackable bodies, however, were selected for illustration due to some unique features.

For example, as shown in FIG. 3, trackable body 71 includes optical separators 72 that enhance the position and orientation detection of the trackable bodies 71. As shown in FIG. 4, trackable body 73 includes flat-body design of the main body 103. As shown in FIGS. 6A-B, the trackable body 73 can also include a manual switch 94 pivotally connected to either the main body 103 or extension 93 to allow masking and unmasking one or more of the indicators 90 to functionally enable or disable either tracking of the trackable body 73 or transmission/use of position data for the trackable body reference point 83. Note, such switch 94 and variations thereof are known to those skilled in the art and are within the scope of the present invention.

As shown in FIG. 5, the trackable body 75 includes an easily gripped elongate body shape for the main body 105 and a main extension 95 to allow easy user manipulation of the trackable body reference point 85, to provide precise contact with a surface point position of a patient P. As shown in FIGS. 7A-B, the trackable body 75 can also include a manual or electronic switch 104 connected to or extending within the main body 105 to allow masking and unmasking one or more of the indicators 90 for passive indicators 90 or interruption of power for active indicators 90, to functionally enable or disable either tracking of the trackable body 75 or transmission/use of position data for the trackable body reference point 85. Note, such switch 104 and variations thereof are known to those skilled in the art and are within the scope of the present invention.

As shown in FIG. 8, the trackable body 77 includes an easily gripped elongate main body 107 connected to a substantially flat-shaped extension 97 having an obtuse angular bend to allow easy pivoting of the trackable body 77 when positioned on a flat surface to thereby allow the user to manipulate the trackable body reference point 87 into contact with a lower patient surface of the patient positioned facing the upper flat surface of the rotating treatment table assembly 37. Such structural configuration further allows the extension 97 to be positioned between a portion of the patient contacting the upper surface of the rotating treatment table assembly 37 and the upper surface of the rotating treatment table assembly 37 with minimal required movement of the patient P. Advantageously, using the trackable body 77, a surface point beneath the patient P and otherwise completely invisible to the user can be located using program product tools, described later.

As shown in FIG. 9A-B, the trackable body 79 preferably includes an easily gripped body shape for the main body 109 and a main extension 99 to allow easy user manipulation of the trackable body reference point 89, to provide precise contact with a surface point position of a patient P. Main extension 99 includes an annular recess 86 extending within a distal end of the main extension 99. A spherical body 86 is positioned adjacent the trackable body reference point 89 within the annular 99 between proximal and distal end shoulders 88 or other means known to those skilled in the art for rotatably holding a spherical body. The spherical body 86 is adapted to contact a surface of the patient and adapted to roll when manipulated along the surface of the patient to enhance movement of the trackable body 79 when in contact with the surface of the patient P, to thereby aid in determining multiple surface point positions without a necessity for extracting the trackable body 79 from the surface of the patient P. Note, although trackable body 79 is illustrated in a form similar to that of trackable body 75, trackable body 79 can have a main body shape similar to that shown in FIGS. 3-7B or others known to those skilled in the art, with or without a switch 94, 104, but preferably includes a main body shape similar to that shown in FIGS. 7A-B including switch assembly 104 and having a main extension 99 such as that shown in FIG. 9B. Other main extension designs, known to those skilled in the art, including, for example, those incorporating laser-distance measuring sources or other low-friction sources that allow manipulation over a contoured patient surface with minimal deformation, are within the scope of the present invention.

According to embodiments of the present invention, trackable body tracking apparatus 51 (see FIG. 1) includes a preferably optically trackable body detector or camera subsystem 53 and a trackable body position determiner 55. The trackable body detector 53 preferably includes a detector body 111 typically positioned spaced apart from the linear accelerator 31 and optically trackable body or bodies, e.g., bodies 71, 73, 75, 77, 79, at a three-dimensional trackable body detector reference location 112. The trackable body detector 53 typically includes a pair of separate and spaced apart optical receivers 113 connected to the detector body 111, each having a field of view and being adapted to receive optical energy provided by each of a plurality of preferably optical retro-reflective indicators 90 when positioned in the field of view to thereby detect a three-dimensional position of each indicator 90 when positioned simultaneously within the field of view of both of the optical receivers 113. According to the preferred configuration, in response to the energy emitted reflected by the indicators 90, the trackable body detector 53 produces a plurality of position signals representing such three-dimensional indicator positions. The trackable body detector 53, depending upon the type of indicators 90, also can include a pair of infrared illuminators 115 each separately positioned adjacent one of the pair of the optical receivers 113 to selectively illuminate each of the plurality of optical retro-reflective indicators 90 when positioned in the field of view of the respective adjacent optical receiver 113. This emission energizes the optical retro-reflective indicators 90 within the field of view of the respective adjacent optical receiver 113.

According to embodiments of the present invention, the trackable body tracking apparatus 51 also includes a trackable body position determiner 55, in communication with the trackable body detector 53, which, in response to the position signals produced by the trackable body detector 55, can determine or otherwise be provided the three-dimensional coordinate position of the isocenter 40 and/or orientation of the isocenter coordinate system of the radiation delivery apparatus 31 (in trackable body detector/camera space), and can determine a three-dimensional coordinate position of the trackable body reference point 81, 83, 85, 87, 89, of a respective one or more of the optically trackable bodies 71, 73, 75, 79, to thereby provide data in order to determine or verify proper target T alignment for the linear accelerator 31.

According to an embodiment of the present invention, the trackable body position determiner 55 includes memory 117 and position determiner software or program product 119 stored in the memory 117. Typically the memory 117 is provided data to identify the various trackable bodies 71, 73, 75, 79, such as, for example, a table of definitions containing the segment lengths between each of the indicators 90 for each respective trackable body used to determine the various reference positions of the optically trackable bodies. Correspondingly, the position determiner software or program product 119, using the segment lengths and the position signals from the trackable body detector 53, determine the three-dimensional coordinate position of the trackable body reference point or points 81, 83, 85, 87, 89, particularly when positioned adjacent a surface of the patient P defining a surface point position, e.g. $S_1$, (FIG. 11), when a preselected number of the plurality of retro-reflective indicators 90 are simultaneously positioned within the field of view of both of the optical receivers 113 of the trackable body detector 53.

Functionally, according to an embodiment of the present invention, using a set of transform matrices, the trackable body position determiner 55 can transform (magnitude, direction, and rotation) the isocenter coordinate system, the trackable body detector coordinate system, each predetermined or preselected optically trackable body reference coordinate system, and/or a separate reference fixture coordinate system for a reference fixture (not shown). Having a chain of transformation matrices, the trackable body position determiner 55 can thus transform to trackable body detector space, and/or vice versa, the three-dimensional coordinate system definition of the isocenter 40 and the three-dimensional coordinate system of the optically trackable body or bodies 71, 73, 75, 79, and of particular interest, the three-dimensional coordinate position of the trackable body reference points 81, 83, 85, 89, usable to identify various surface locations of the patient P.

Embodiments of the present invention also include a target alignment analyzing computer 61 positioned in communication with the trackable body position determiner 55 to determine proper target alignment for the linear accelerator 31. The target alignment analyzing computer 61 has a processor 121 and memory 123 coupled to the processor 121 to store operating instructions, the three-dimensional coordinate position of the isocenter 40, and the source-to-axis distance SAD of the linear accelerator 31, therein. The target alignment analyzing computer 61 can be either fixedly positioned within, for example, the simulation room or radiation delivery room, as illustrated in FIG. 1, or positioned on a mobile unit such as, for example, the cart 125 illustrated in FIG. 2. A display is coupled to the processor 123 to display target alignment data, described below. A preferably large-screen display 127 (FIG. 1) can be mounted or otherwise connected to a wall or other fixture. A preferably touch-screen display 129 (FIG. 2) can be positioned on the mobile unit 125 to provide ready access to allow user input to select various program product components, modules, or functions. Various embodiments of the present invention can incorporate either of the displays 127, 129, or both, providing the user a selection depending upon the desired measurement, or complication level of such method. Other forms of input device can be used alternatively. Advantageously, the mobile unit 125 can also carry one or more of the various trackable bodies 71, 73, 75, 77, 79, along with other computer peripherals or trackable body attachments.

Embodiments of the present invention include a target alignment analyzing program product 63 stored in the memory 123 of the target alignment analyzing computer 61 to facilitate and verify proper target alignment for radiation delivery. The target alignment analyzing program product 63 can be in the form of microcode, programs, routines, and symbolic languages that provide a specific set for sets of ordered operations that control the functioning of the hardware and direct its operation, as known and understood by those skilled in the art. As perhaps best shown in FIG. 10, the target alignment analyzing program product 63 can include the various combinations of one or more of the program product functions, described below.

Figure 11:
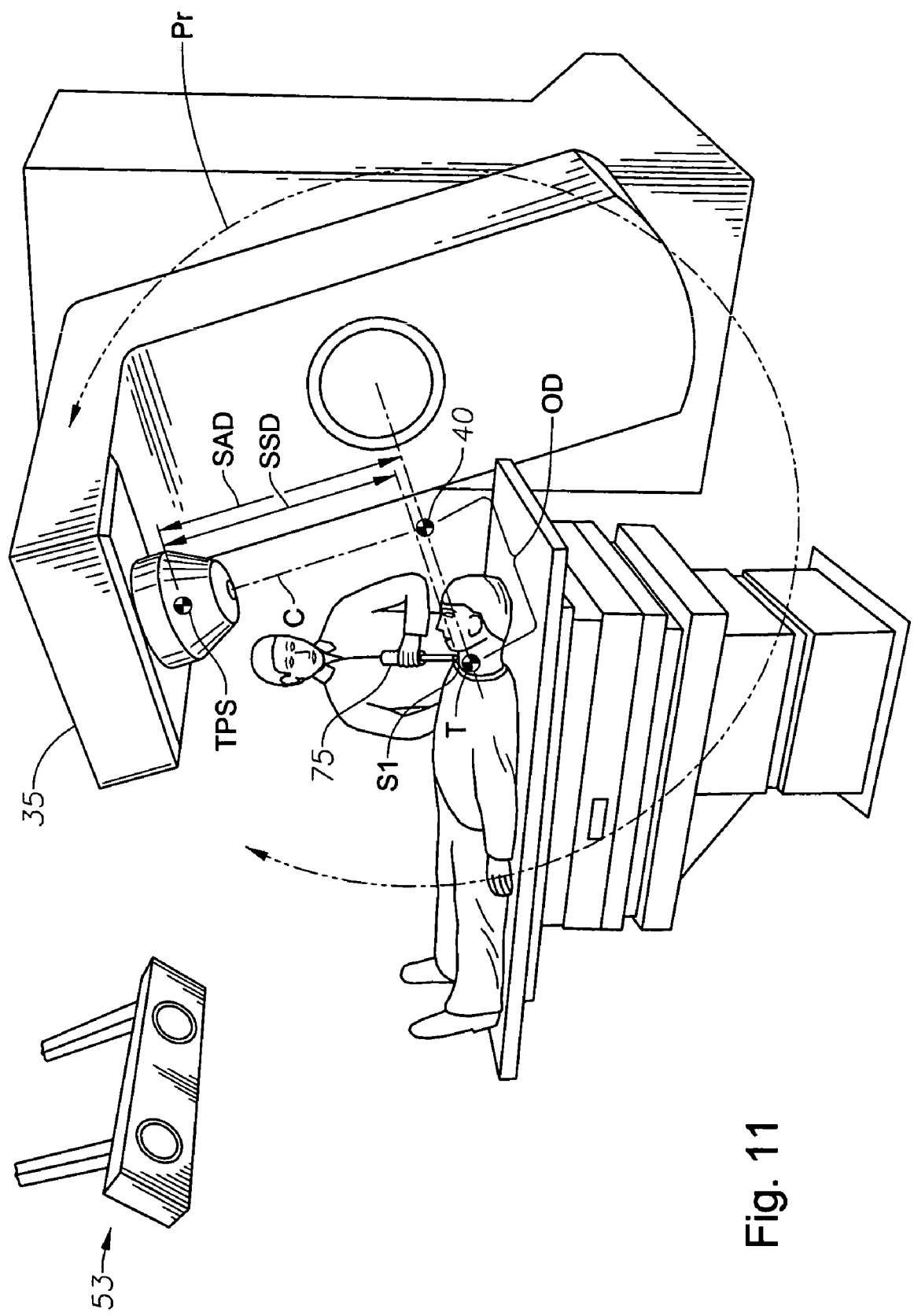
FIG. 11 is a perspective view of a system to facilitate and verify proper target alignment for radiation delivery according to an embodiment of the present invention.
Figure 12:
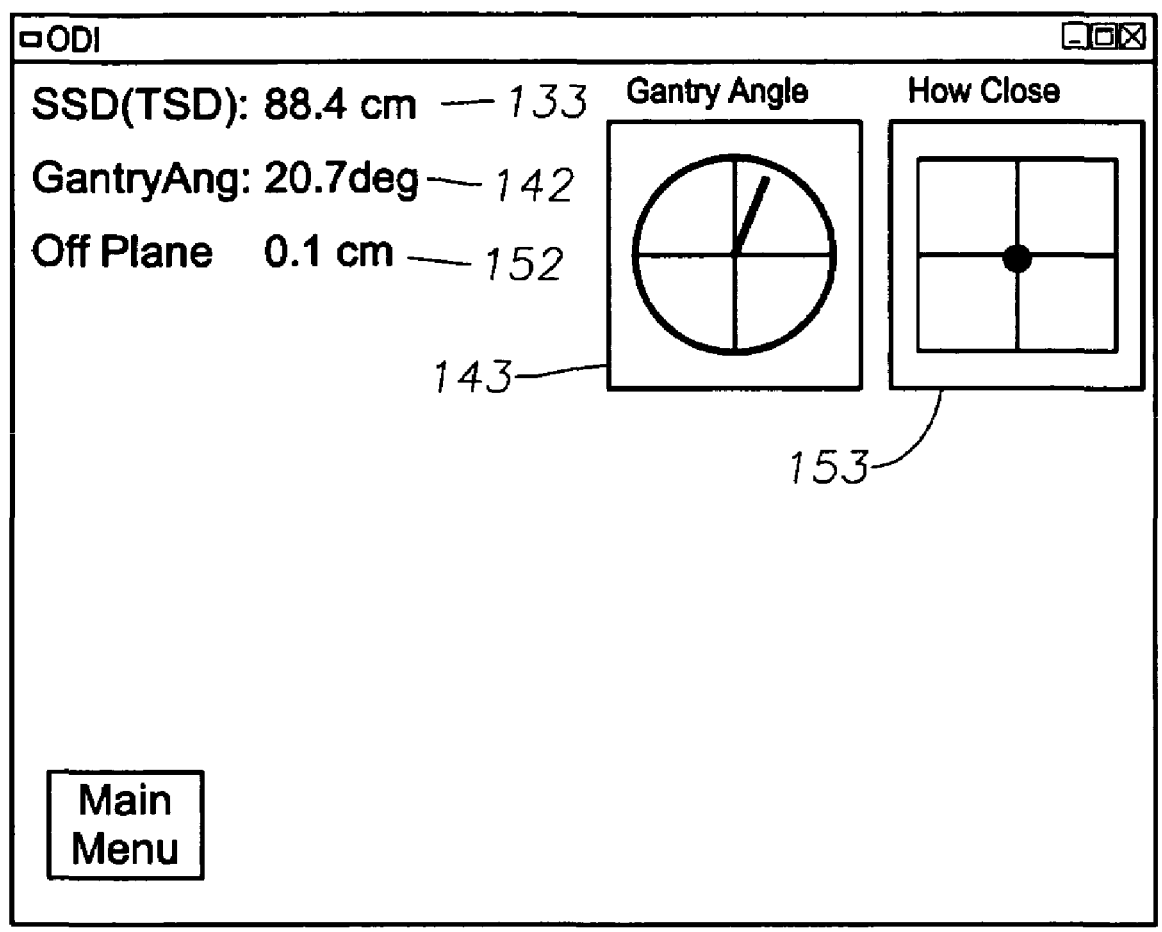
FIG. 12 is a schematic diagram of a graphical user interface for a system to facilitate and verify proper target alignment for radiation delivery according to an embodiment of the present invention.

An optical distance indicator simulator 131 is positioned to provide source-to-surface (SSD) distance determinations, a corresponding gantry angle of rotation, and off-plane distance of a selected surface point from the plane of gantry rotation Pr (FIG. 11), without the need for repositioning the patient P to place the target T within the plane of gantry rotation Pr and without the need to actually rotate the rotating gantry assembly 35. Thus, the optical distance indicator simulator 131 includes or otherwise interfaces with a source-to-surface distance determiner 132 positioned to receive the three-dimensional coordinate position of isocenter 40 and/or the source-to-axis distance SAD, and a surface point position $S_1$ on a surface of the patient P (see FIG. 11), to determine a component of a distance within the plane of rotation Pr of the rotating gantry assembly 35 between the theoretical point source TPS (FIG. 12) and the surface of the patient P to define a source-to-surface distance SSD (FIG. 11). This source-to-surface distance SSD can be computationally determined, for example, by first determining the on-axis distance between the surface point position $S_1$ and the isocenter 40 and subtracting the distance from the source-to-axis distance SAD. The three-dimensional coordinate position of the surface point position $S_1$ is determined through use of the trackable body position determiner 55 when the trackable body reference point 91, 93, 95, 97, 99 of one of the trackable bodies 71, 73, 75, 77, 79 or other not shown, is positioned coincident with the surface point position $S_1$. Such measurement is preferably substantially instantaneous and can be continuous. The surface-to-axis distance SAD can be presented numerically, e.g., as shown in output field 133 (FIG. 12), having a number of decimal places configurable by a user.

The optical distance indicator simulator 131 preferably also includes or otherwise interfaces with an emitter carrier (gantry) angle determiner 141 positioned to receive the three-dimensional coordinate position of isocenter 40 and the surface point position $S_1$ on a surface of the patient P (see FIG. 11) to determine a gantry angle of rotation (see FIG. 12) of the rotating gantry assembly 35 that would position a path of the emitter central axis C simultaneously through the surface point position $S_1$ and the isocenter 40. The required mathematical computations for determining such gantry angle of rotation are known to those skilled in the art. This angle can be presented numerically as in output field 142 and/or graphically as in graphical display 143. Such angular data used in the graphical display 143 can be configured to either use or match such data to the used by the controller 39 of the linear accelerator 31.

Because the traditional ODI measurement would, by definition, be made in the plane of gantry rotation Pr, it is preferable to provide the user clues to help the user appropriately select a proper measurement point, to thereby remain intuitive to the user. Thus, advantageously, the optical distance indicator simulator 131 preferably includes or otherwise interfaces with an off-plane distance determiner 151 (FIG. 10) positioned to receive the determined surface point position $S_1$, to determine an off-plane (offset) distance OD between the surface point position $S_1$ and the plane of rotation Pr for the rotating gantry assembly 35 (see FIG. 11). The off-plane distance OD (see FIG. 12) provides a user a distance required to move the target T normal to the plane of rotation Pr for the rotating gantry assembly 35 to position the target within the plane of rotation Pr of the rotating gantry assembly 35. That is, for radiation delivery, the off-plane distance OD provides indications that aid the user to adjust the rotating treatment table assembly 37 to position the target T of the patient P to place the desired measurement point in the plane of gantry rotation Pr. With respect to pre-radiation delivery analysis, such as that performed in the simulation room, such data is important because the selected measurement point, surface point position $S_1$, is typically physically marked on the patient P for later verification in the radiation delivery room.

Correspondingly, once the patient P is moved to the radiation delivery room, such data is a desirable feature as it aids the user to verify that the associated surface of the patient is correctly positioned relative to the radiation emitter 33. The off-plane distance OD can be both numerically illustrated as shown in output field 152 and/or graphically illustrated as shown in the "How Close" display 153 of FIG. 12. The "How Close" display aids the user by visually orienting the user with a relative amount of correction required to place the surface of the patient P, as indicated by surface point position $S_1$, in the correct location relative to the radiation emitter 33. Such measurements can be taken at any surface point position $S_1$-$S_n$ visible to the trackable body detector 53, which advantageously include positions that a traditional ODI could not project upon. Further, according to an embodiment of the present invention, the data displayed in FIG. 12 can be continuously enabled during other functional applications, described below. Still further, advantageously, such data, as with data associated with the other functional applications, described below, can be exported for comparison with the treatment plan, other application program data, and/or to a printer (not shown) preferably interfaced with the user's local network. The printing function can include input fields to allow user to enter patient demographics data, patient treatment data, or other pertinent data, and/or can interface with other applications to allow automatic retrieval of such data.

As shown in FIGS. 10, and 13A-14, a central axis thickness determiner 161 is provided to display to a user a thickness between two opposing surface position points $S_1$, $S_2$ located on either side of the target T along a path of the emitter central axis C (FIG. 13A), preferably along with source-to-surface distance determinations, a corresponding gantry angle of rotation, and an off-plane distance of a selected surface point. According to an embodiment of the target alignment analyzing program product 63, the central axis thickness determiner 161 includes a source-to-surface distance determiner, such as determiner 132, an emitter carrier angle determiner, such as determiner 141, and/or an off-plane distance determiner, such as determiner 151. According to another embodiment of the target alignment analyzing program product 63, the central axis thickness determiner 161 instead directly interfaces with source-to-surface distance determiner 132, emitter carrier angle determiner 141, and/or off-plane distance determiner 151.

Regardless of the configuration, in response to the surface point position $S_1$ or other surface point position selected by the user, and associated gantry angle of rotation (see FIG. 14), and in response to a preferably substantially continuous flow of three-dimensional coordinate position data provided by the trackable body position determiner 55 for a trackable body reference point of one or more trackable bodies such as, for example, the trackable bodies 71, 73, 75, 77, 79, the central axis thickness determiner 161 provides visual feedback (see FIG. 14) to the user such as, for example, through the determined gantry angle of rotation displayed in output field 162 and graphical display 163 and the off-plane distance OD numerical value displayed in output field 164. The lower half of the displayed indication in the graphical display 163 of the gantry angle of rotation can also be presented to aid the user to locate or determine the opposing gantry angle of rotation, once the first surface point position $S_1$ is selected. In an alternative embodiment of the present invention, the gantry angle of rotation for the opposing point can also be predicted and immediately displayed numerically in an output field (not shown). A "How Close" output display 165 can be provided to aid the user by visually orienting the user with a relative amount of correction required to place the surface of the patient P, as indicated by surface point position $S_1$, in the correct location relative to the radiation emitter 33. This correction should be the same for $S_2$. Advantageously, such types of visual feedback aid the user in positioning the trackable reference body reference point of the selected trackable body 71, 73, 75, 77, 79, or other trackable body adjacent an opposite surface of the patient P along the emitter central axis C defining the determined gantry angle of rotation, to determine a second surface point position $S_2$ (FIG. 13A) located on a second opposite surface.

Further, according to an alternative embodiment of the present invention, the "How Close" display 165 can instead display two directions of deviation, the second indicating a deviation parallel to the plane of gantry rotation, to further aid the user to locate the second surface point position $S_2$ located opposite the first surface point position $S_1$. Also, as shown for illustrative purposes in FIG. 13B, according to an alternative embodiment of the present invention, the off-plane distance determiner included in or interfaced with central axis thickness determiner 161 can determine an off-plane distance OD' between the trackable reference body reference point 87 of the trackable body 77 and a first surface point plane SP. The off-plane distance OD' provides the user a distance required to move the trackable reference body reference point 87 normal to the first surface point plane SP to aid the user in positioning the trackable reference body reference point 87 adjacent the second surface of the patient at the second surface point $S_2$ opposite the first surface point position $S_1$. The "How Close" display 165 can instead display such distance.

An input field such as button 166 (FIG. 14) allows the user to select between indicating to the central axis determiner 161 that the data provided by the trackable body position determiner 55 is for either the first or for the second surface point positions $S_1$, $S_2$. Once the surface point position $S_2$ is located, preferably using relatively simple calculations, such as those described above with respect to the source-to-surface distance determiner 132 or others known to those skilled in the art, the central axis thickness determiner 161 can determine a patient thickness along the emitter central axis C between the first and the second surface point positions $S_1$, $S_2$, shown in output field 167.

Figure 10:
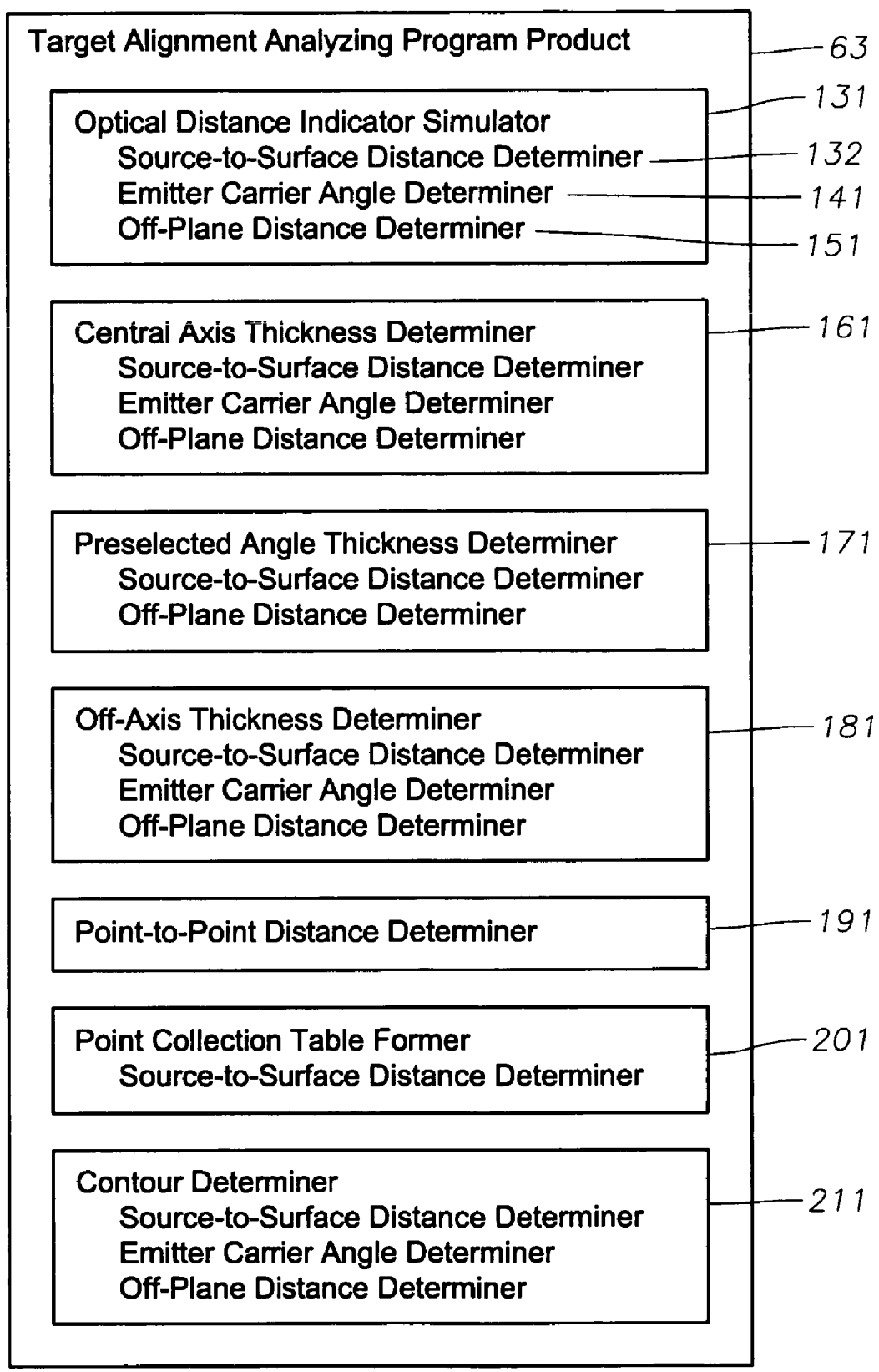
FIG. 10 is a schematic diagram of a program product to facilitate and verify proper target alignment for radiation delivery according to an embodiment of the present invention.

As shown in FIGS. 10, 15, and 16, a preselected angle thickness determiner 171 is provided to display to a user a thickness between two opposing surface position points $S_1$, $S_3$ located on either side a patient P along a path associated with a preselected gantry angle of rotation angle, e.g., vertical, preferably along with source-to-surface distance determinations, and an off-plane distance of a selected surface point. According to an embodiment of the target alignment analyzing program product 63, the preselected angle thickness determiner 161 includes a source-to-surface distance determiner, such as determiner 132, and/or off-plane distance determiner such as determiner 151. According to another embodiment of the target alignment analyzing program product 63, the preselected angle thickness determiner 171 instead directly interfaces with source-to-surface distance determiner 132 and/or off-plane distance determiner 151.

Regardless of the configuration, once a surface point position $S_1$ is selected, in response to determining the selected surface point position $S_1$ or other surface point position selected by the user (see FIG. 15) and receiving or preselecting the associated preselected gantry angle of rotation, e.g. vertically, and in response to a preferably continuous flow of three-dimensional coordinate position data provided by the trackable body position determiner 55 for a trackable body reference point of one or more trackable bodies such as, for example, the trackable body 77, the preselected angle thickness determiner 171 provides visual feedback to the user. Such visual feedback can include, for example, the off-plane distance numerical value displayed in output field 172 and "How Close" display 173 (see, e.g., FIG. 16). Such visual feedback is provided to aid the user in positioning the trackable reference body reference point, e.g., point 87, adjacent a third surface of the patient P opposite the first surface along the preselected angle, and to determine a third surface point position $S_3$ located on the third surface, to thereby determine a patient thickness between the first and the third surface point positions $S_1$, $S_3$.

Specifically, the off-plane distance numerical value displayed in output field 172 and the "How Close" display 173 can aid the user by visually orienting the user with a relative amount of correction required to place the surface of the patient P, as indicated by surface point position $S_1$, in the correct location relative to the first surface point position $S_1$. Alternatively, the values displayed in output field 172 and display 173 can be an off-plane distance OD" between the trackable reference body reference point 87 of the trackable body 77 and a first surface point plane SP' parallel with an axis representing the preselected angle. Regardless, advantageously, such types of visual feedback aid the user in positioning the trackable reference body reference point of the selected trackable body 77 or other trackable body, adjacent an opposite surface of the patient P along an axis having the preselected preferably vertical angle, to determine a surface point position $S_3$ located on the opposite surface of the patient P.

An input field such as button 174 (FIG. 16) allows the user to select between indicating to the preselected angle thickness determiner 171 that the data provided by the trackable body position determiner 55 is for the first or for the third surface point positions $S_1$, $S_3$. Having selected the surface point position $S_1$, shown in output field 175, having determined the surface point position $S_3$, shown in output field 176, and preferably having determined the surface-to-source distances SSDs for the first and the third surface point positions $S_1$, $S_3$ shown in output fields 177 and 178, respectively, the preselected angle thickness determiner 171 determines a patient thickness between the first and the third surface point positions $S_1$, $S_3$ shown in output field 179.

Note, such determination can be made using relatively simple calculations, such as those described above with respect to the source-to-surface distance determiner 132, or others known to those skilled in the art. Note also, according to a preferred embodiment of the present invention, the first or for the third surface point positions $S_1$, $S_3$ are continuously provided substantially real-time corresponding to movement of the trackable body and are displayed in isocenter coordinates. Note further, a special case of such preselected angle thickness determiner 171 is shown in FIG. 16, whereby the preselected angle is presumed to be vertical, and thus, all calculations made by the preselected angle of thickness determiner 171 are made under such assumption, i.e., no angular data need be provided for use in the calculations. Correspondingly, surface point position $S_3$ is located on in a vertically opposite surface of the patient P. Advantageously, such vertical thickness measurements can be useful to allow the user perform relatively simple dose calculations with or without aid of a computer.

As shown in FIG. 17, the radiation beam provided by the collimator or other radiation emitter 33 can be divergent from the emitter central axis upon entry into the patient P. Correspondingly, the radiation beam positioned to provide radiation to the first surface point position $S_1$ may not exit the patient on the opposite surface of the patient P such as, for example: at a location coincident with a second surface point position $S_2$ aligned with a path of the emitter central axis C positioned to pass through the first and second point positions $S_1$, $S_2$ and the target T (FIG. 13A); or at a location coincident with a third surface point position $S_3$ aligned with a preselected path between the first and the third surface point positions $S_1$, $S_3$ based on a preselected or a predetermined gantry angle of rotation (FIG. 15). Instead, due to the divergent nature of the radiation beam, the radiation beam may tend to emerge at a fourth off-axis surface point position $S_4$. Thus, in order to advantageously provide a more accurate dose calculation for such off-axis radiation delivery, embodiments of the target alignment analyzing program product 63 can include an off-axis thickness determiner 181 (FIG. 10).

In response to the surface point position $S_1$ or other surface point position selected by the user and/or associated determined or predetermined/assumed gantry angle of rotation, and in response to a preferably continuous flow of three-dimensional coordinate position data provided by the trackable body position determiner 55 for a trackable body reference point of one or more trackable bodies such as, for example, one of the trackable bodies 71, 73, 75, 77, 79, the off-axis thickness determiner 181 provides visual feedback to the user to aid the user in positioning the trackable reference body reference point of the selected trackable body adjacent an opposite surface of the patient P located along an arc approximating beam field divergence of the radiation beam and to determine the fourth surface point position $S_4$, to thereby determine a patient thickness along the arc between the first and the fourth surface point positions $S_1$, $S_4$. Such thickness calculation (not shown) can be used to substitute that displayed in FIGS. 14 and 16 and/or used to verify proper dose calculations. The source-to-surface distance SSD for the off-axis surface point position $S_4$ can also be displayed. This feature is particularly useful where radiation delivery is from a single beam. As such, each function of the target alignment analyzing program product 63 including display of source-to-surface distances SSD, including those described below, can include measurement computations utilizing such radiation beam divergence.

Figure 18:
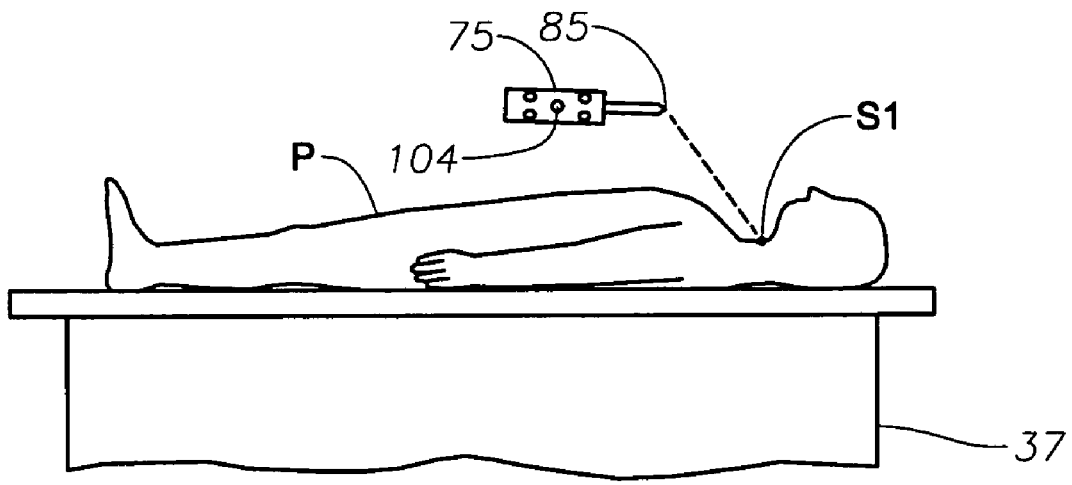
FIG. 18 is a perspective view of a portion of a system to facilitate and verify proper target alignment for radiation delivery according to an embodiment of the present invention.
Figure 19:
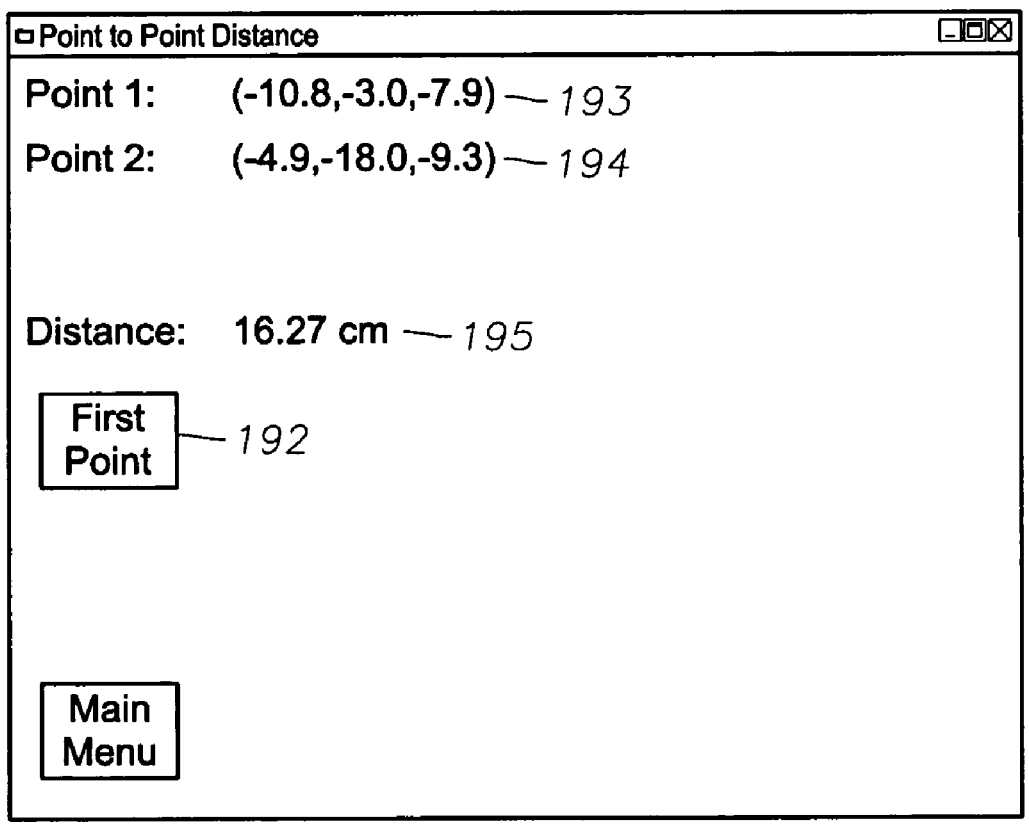
FIG. 19 is a schematic diagram of a graphical user interface for a system to facilitate and verify proper target alignment for radiation delivery according to an embodiment of the present invention.

As shown in FIGS. 10, 18, and 19, a point-to-point distance determiner 191 is provided to display to a user a preferably straight line distance from a first selected surface point position $S_1$ to the current position of the trackable body reference point, e.g., trackable body reference point 85 of trackable body 75. That is, in response to the user positioning the trackable body reference point 85 adjacent a first surface of the patient P and defining the first surface point position $S_1$, either through use of a switch on the trackable body 75 (described later) or through use of an input field such as the "First Point" input field button 192 (FIG. 19) and/or in combination with manipulation of switch 104, the user identifies the first surface point position $S_1$ to display in output field 193. In response to such identification or determination, the point-to-point distance determiner 191, through trackable body reference point positional data provided by the trackable body position determiner 55, continuously determines and displays the three-dimensional coordinate position of the trackable body reference point 85 in output field 194 and substantially continuously determines and displays in output field 195 the distance between the first surface point position $S_1$ and the three-dimensional coordinate position the trackable body reference point 85. According to an embodiment of the point-to-point distance determiner 191, switch 104 can instead be utilized to interrupt or freeze such display. Advantageously, by placing the trackable body reference point 85 adjacent a surface of the patient P, the user is provided substantially instantaneously a coordinate of a surface point position and the distance to that surface point position to or from the first surface point positions $S_1$. Note, such determination can be made using relatively simple calculations known to those skilled in the art. Note also, the positions of the points in output fields 193, 194 are preferably but need not be displayed in isocenter coordinates.

Figure 20:
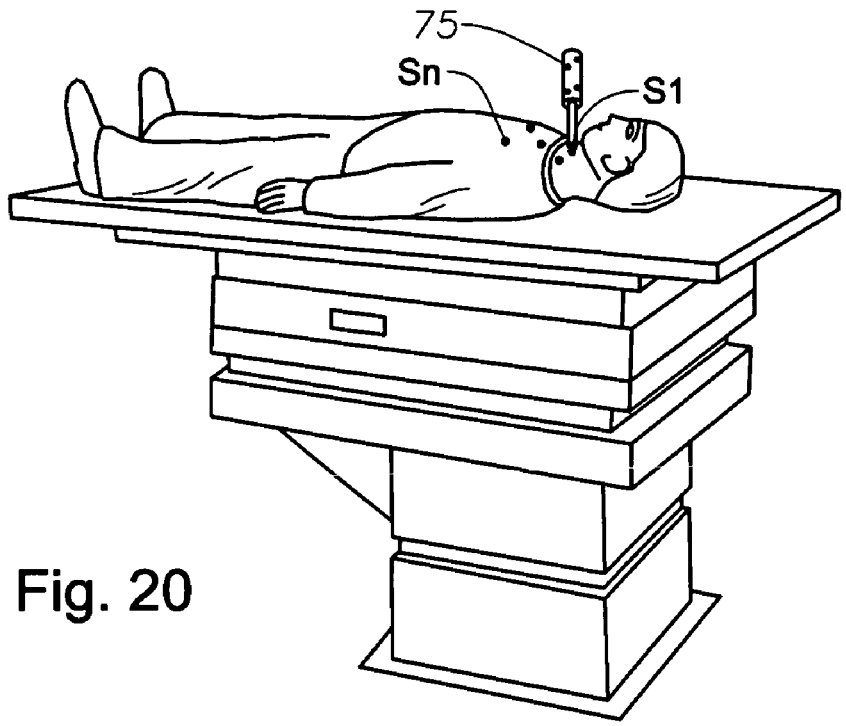
FIG. 20 is a perspective view of a portion of a system to facilitate and verify proper target alignment for radiation delivery according to an embodiment of the present invention.
Figure 21:
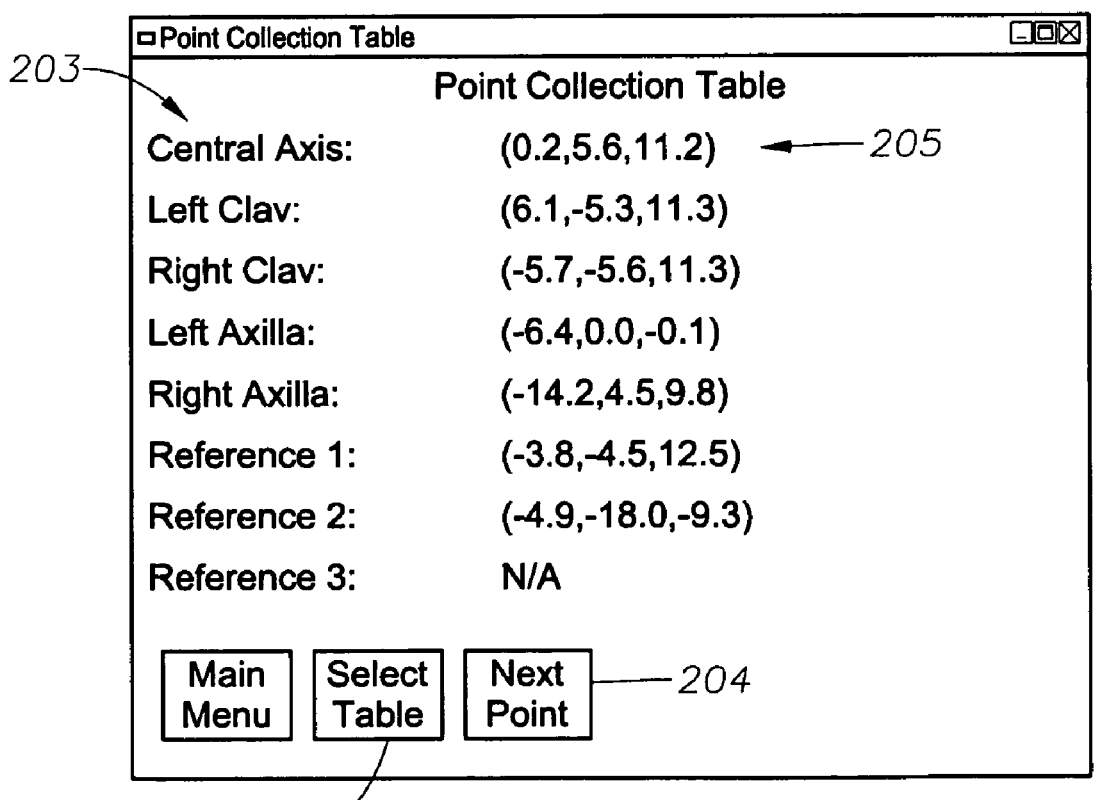
FIG. 21 is a schematic diagram of a graphical user interface for a system to facilitate and verify proper target alignment for radiation delivery according to an embodiment of the present invention.

As shown in FIGS. 10, 20, and 21, a point collection table former 201 is provided to display to a user a table of surface point positions for multiple preferably pre-defined surface locations which provide the user and ability to verify patient position over multiple sample locations. As shown in FIG. 21, according to an embodiment of the target alignment analyzing program product 63, through use of an input field such as the "Select Table" input field button 202, the user can select from one or more suitable pre-defined point collection tables of points preferably having both pre-defined comparison points and/or user defined reference points 203. Such tables can be user-defined or defined by some other application. Once the table is selected, through use of an input field such as the "Next Point" input field button 204, the user can sequentially scroll through each respective displayed point 203 to apply to the point collection table former 201 the trackable body reference point positional data provided by the trackable body position determiner 55. Correspondingly, the point collection table former 201 displays the three-dimensional coordinate position of the trackable body reference point 85 in output fields 205.

The user need only contact the trackable body reference point 85 to a patient surface location coinciding with one of the comparison/reference points 203 and either select the "next point" input field button 204 or engage a switch 104 on the trackable body 75 if provided for, to command the point collection table former 201 to associate the three-dimensional coordinate system position of the trackable body reference point 85 with the contacted patient surface location and/or sequence to the next comparison/reference point 203. Further, according to an embodiment of the target alignment analyzing program product 63, the point collection table former 201 can determine and display for each of the comparison/reference points 203 a source-to-surface distance (not shown) alone or in combination with the comparison/reference points 203, to thereby further ensure proper patient positioning. According to the preferred embodiment of the point collection table former 201, the points displayed in output fields 205 are in isocenter coordinates, but can instead be referenced to some other central reference point, if desired.

Figure 22:
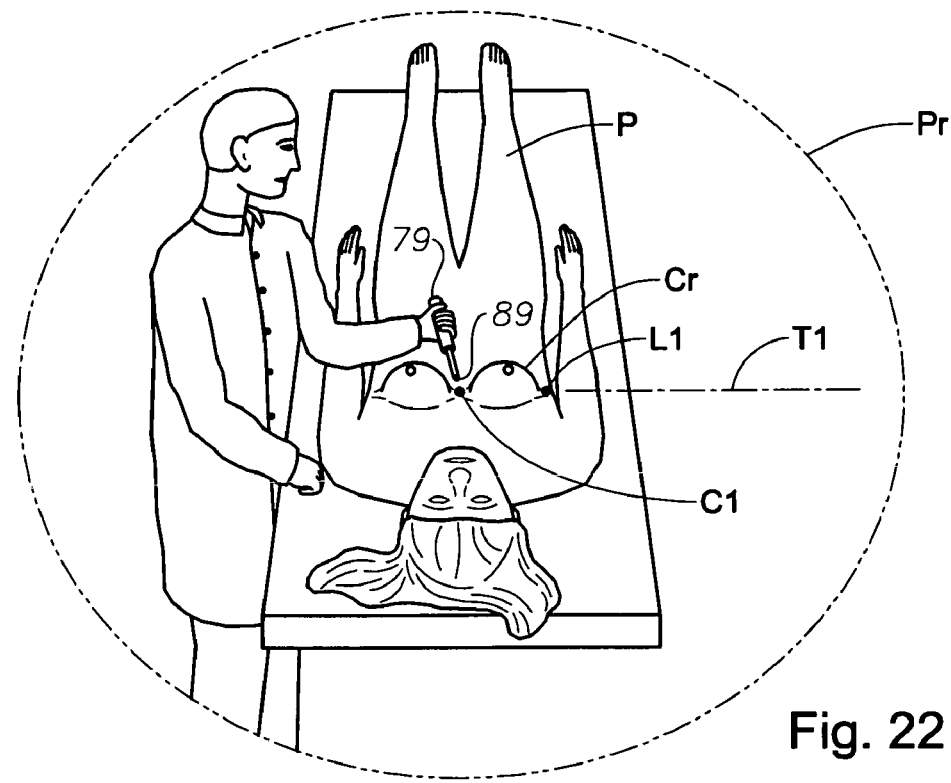
FIG. 22 is a perspective view of a portion of a system to facilitate and verify proper target alignment for radiation delivery according to an embodiment of the present invention.
Figure 23:
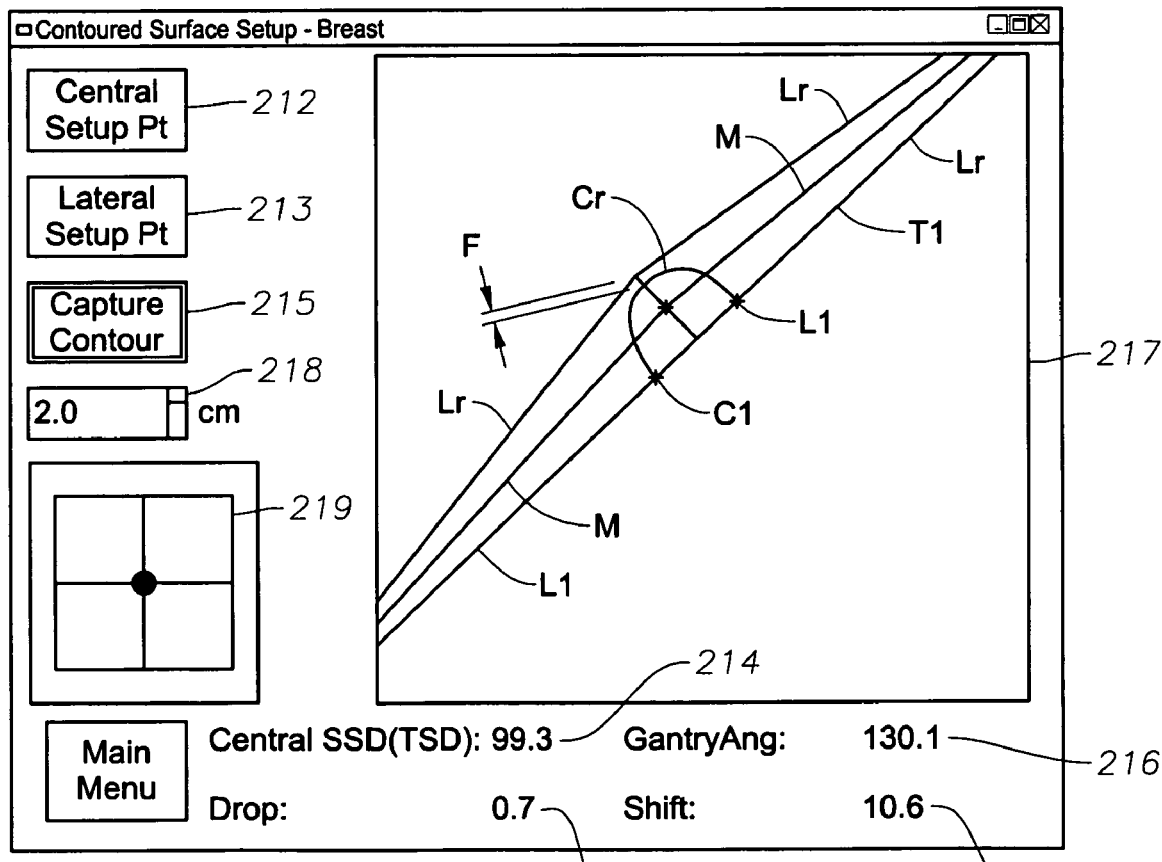
FIG. 23 is a schematic diagram of a graphical user interface for a system to facilitate and verify proper target alignment for radiation delivery according to an embodiment of the present invention.
Figure 24:
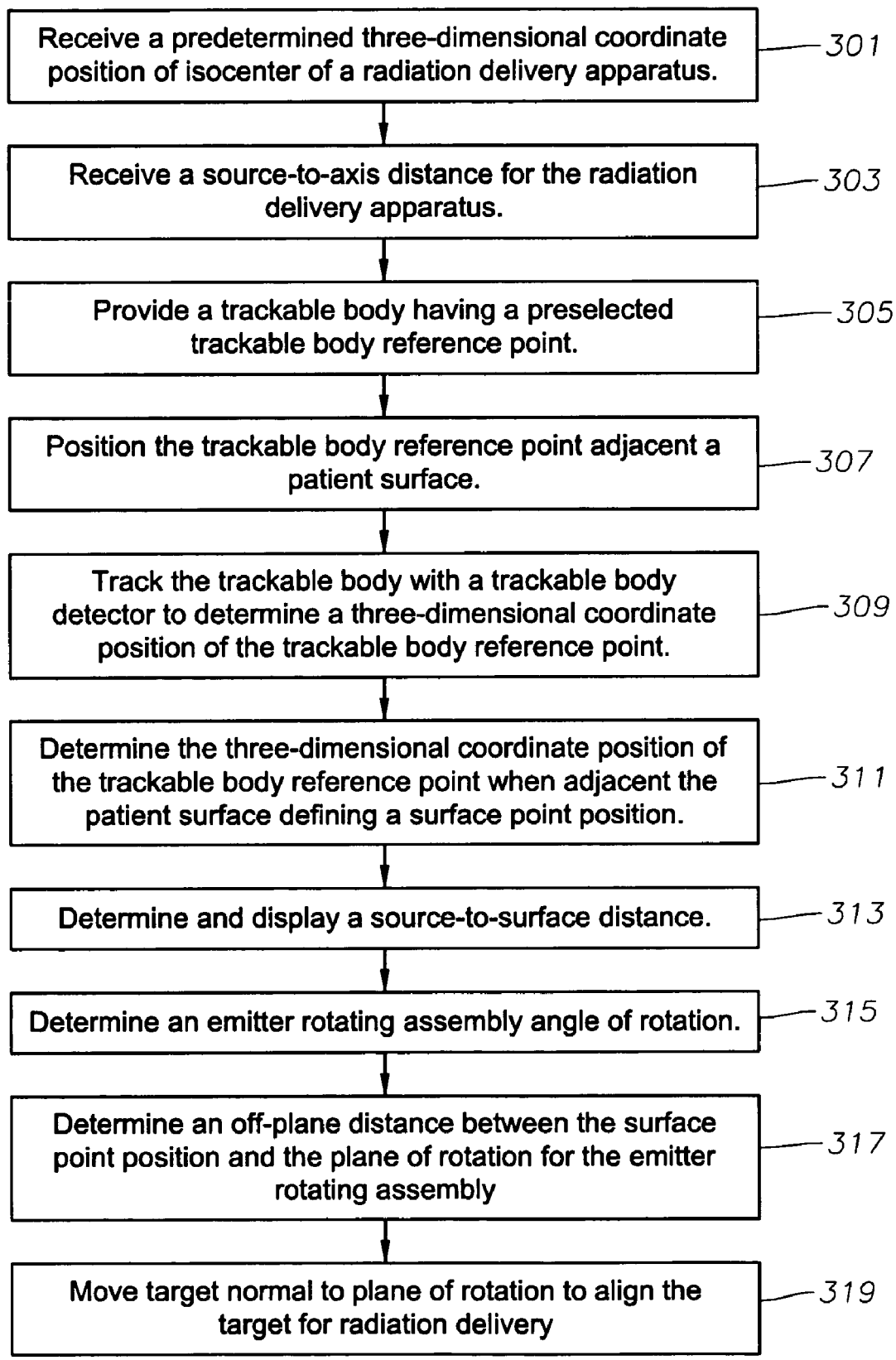
FIG. 24 is a flow chart of a method to facilitate and verify proper target alignment for radiation delivery according to an embodiment of the present invention.
Figure 25:
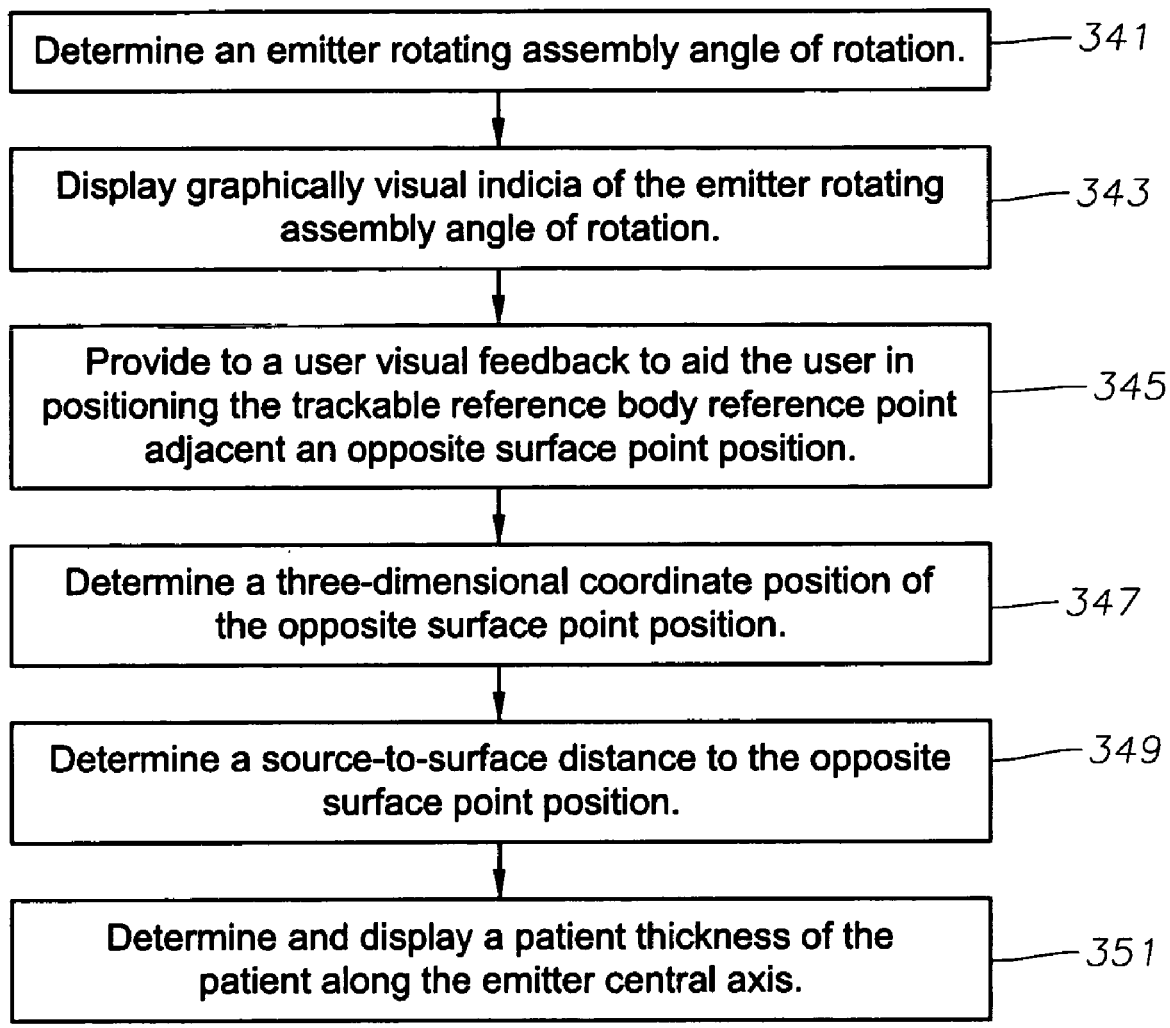
FIG. 25 is a flow chart of a method to facilitate and verify proper target alignment for radiation delivery according to an embodiment of the present invention.
Figure 26:
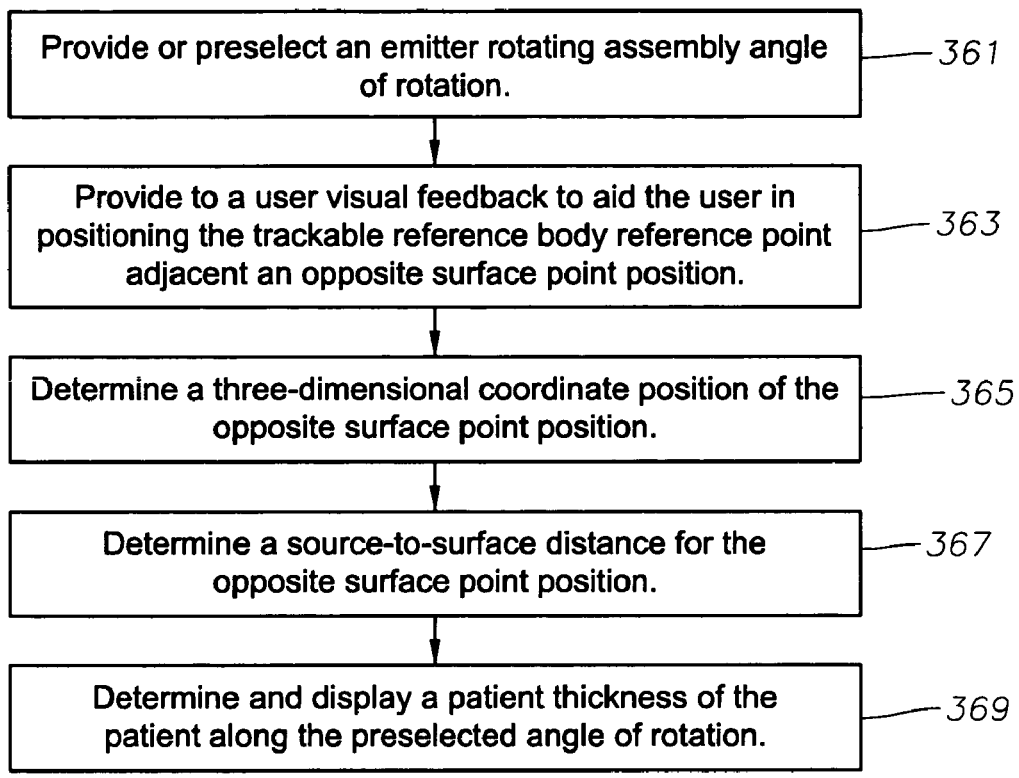
FIG. 26 is a flow chart of a method to facilitate and verify proper target alignment for radiation delivery according to an embodiment of the present invention.
Figure 27:
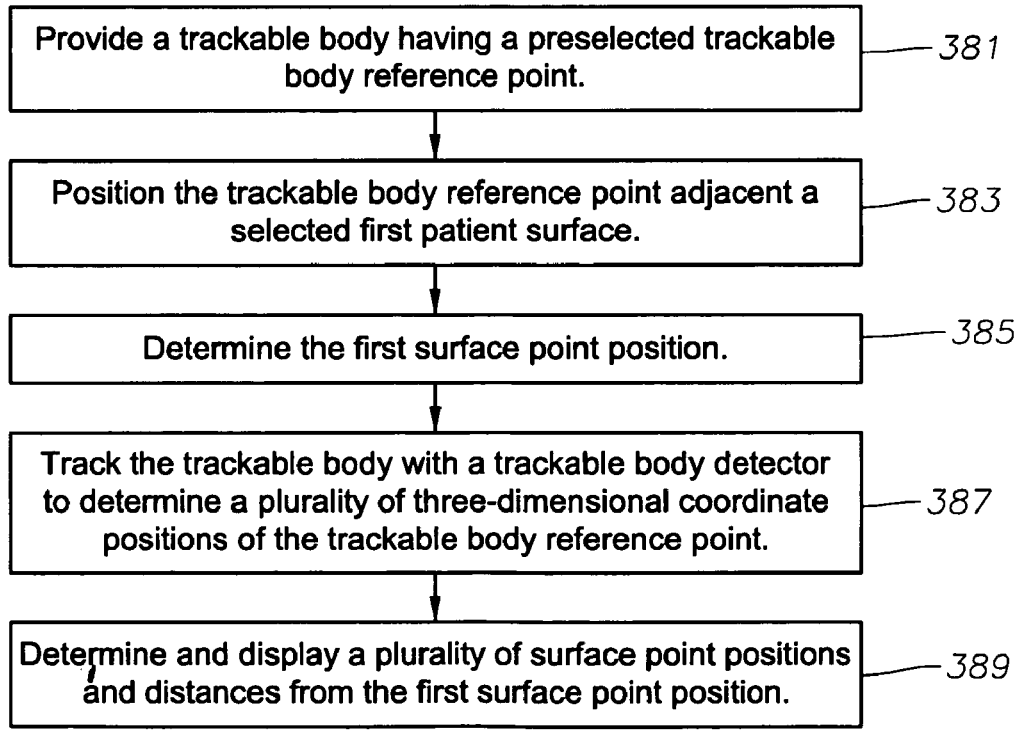
FIG. 27 is a flow chart of a method to facilitate and verify proper target alignment for radiation delivery according to an embodiment of the present invention.
Figure 28:
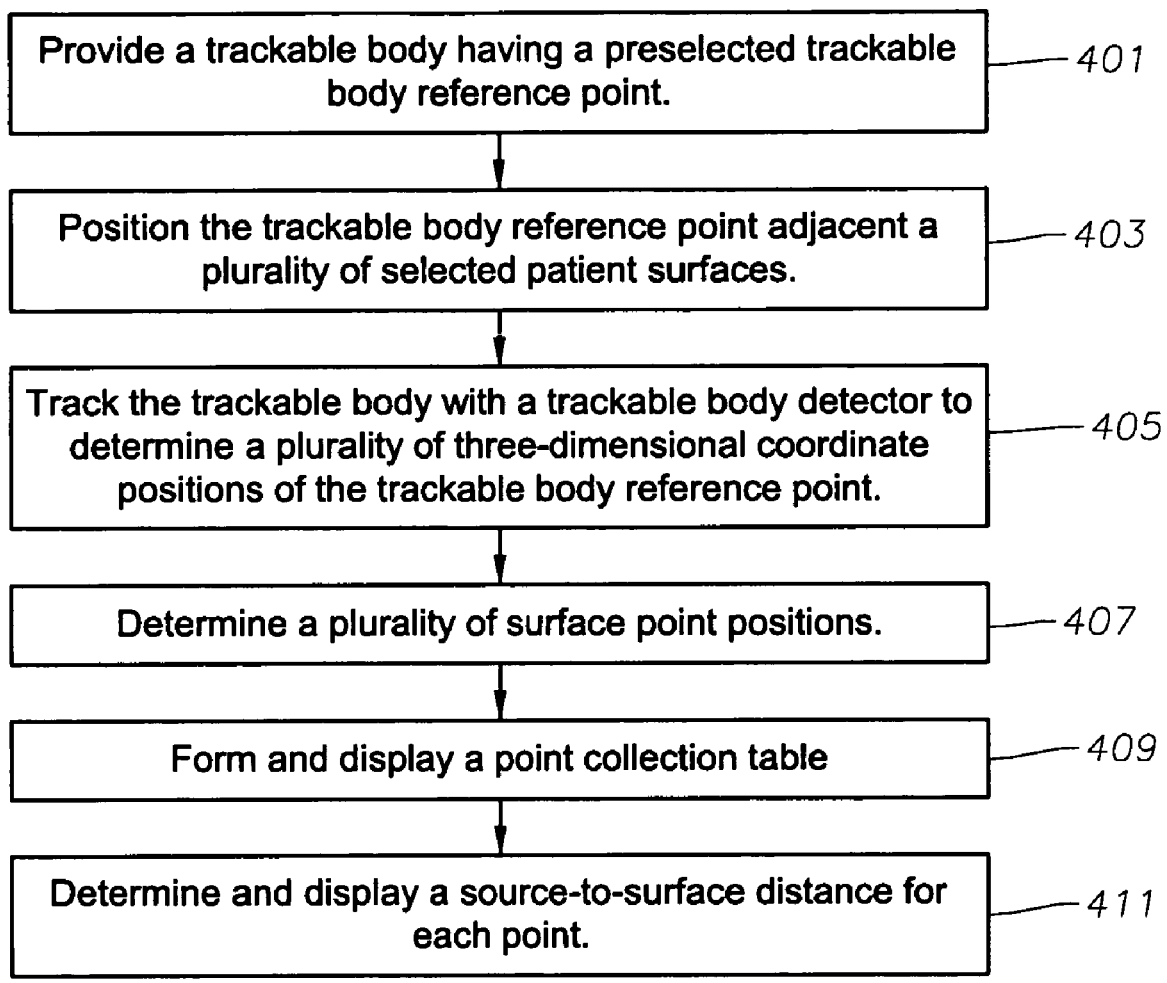
FIG. 28 is a flow chart of a method to facilitate and verify proper target alignment for radiation delivery according to an embodiment of the present invention.
Figure 29:
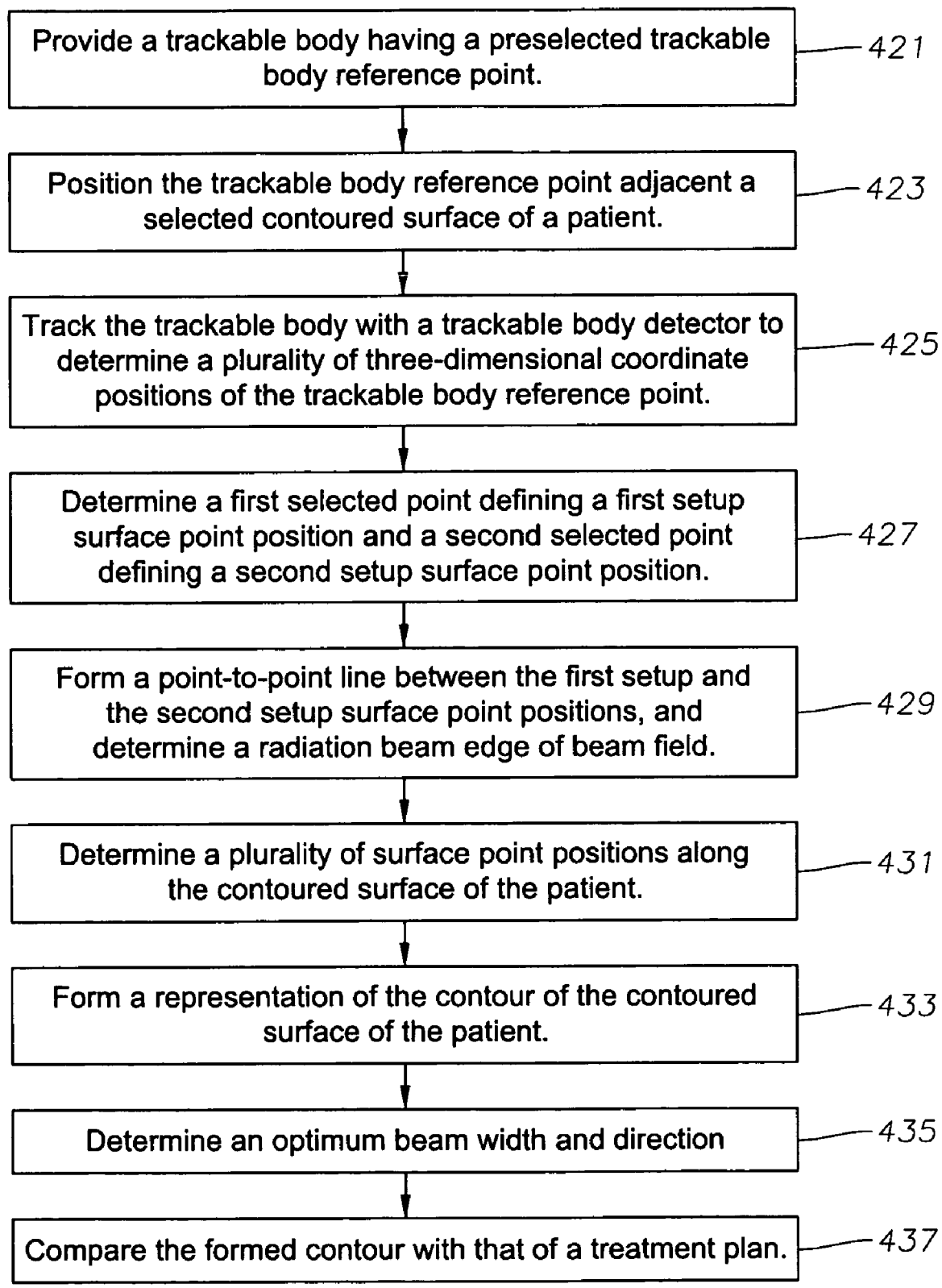
FIG. 29 is a flow chart of a method to facilitate and verify proper target alignment for radiation delivery according to an embodiment of the present invention.

As shown in FIGS. 10, 22, and 23, a contour determiner 211 is provided to display to a user an optimum emitter angle and beam width of the linear accelerator 31 to enhance delivery of radiation to the contoured body part, e.g., chin or breast. For example, a very common, time-consuming, and potentially error prone procedure involves radiation treatment of the breast of a patient P. Such treatment does not normally include use of a CT scan, nor sophisticated treatment planning. Radiation beam delivery locations are typically determined geometrically by measuring the contour of the patient P along a plane of gantry rotation which is recorded for later set-up in the radiation delivery room. As shown in FIGS. 22-23, according to an embodiment of the contoured determiner 211 of the target alignment analyzing program product 63, the user places the trackable body reference point of a suitable trackable body, e.g., trackable body 79, in contact with a normally pre-selected central setup point, e.g., surface point positions $C_1$ and, through use of an input field such as the "Central Setup Pt" input field button 212, commands the contour determiner 211 to associate three-dimensional coordinate system position of the trackable body reference point 89 provided by the trackable body position determiner 55 with the contacted patient surface position $C_1$. A similar procedure can be used to establish the lateral setup point $L_1$ using the "Lateral Setup Pt" input field button 213. The central surface-to-source distance SSD is determined and can be displayed in output field 214. A line $T_1$ between the setup points $C_1$, $L_1$ defines a location used to position proximal field edges of the radiation beam. This line is generally tangential to a main body portion of the patient P not receiving radiation treatment. Note, a switch, such as, for example, switch 94 or 104, can instead be utilized to command association of the three-dimensional coordinate position of the trackable body reference point 89 to the appropriate setup point $C_1$, $L_1$.

Through use of an input field such as the "Capture Contour" input field button 215, alone or in combination with switch 94 or 104, the user can manipulate the trackable body 79 along the contour Cr of the breast between the central setup point $C_1$ and the lateral setup point $L_1$ along the plane of gantry rotation, to allow the contour determiner 211, through substantially continuous (sampled) determination of the three-dimensional coordinate position of the trackable body reference point 89 by the trackable body position determiner 55. This contour Cr, preferably located/displayed to the user through use of a laser (not shown), is used to then determine the desired location of the isocenter 40 of the linear accelerator 31 and, along with preferably a pre-defined or user-defined value of "flash" F (FIG. 23), and the desired beam-field width at isocenter. The "flash" F is added to the width of the radiation beam to ensure a contoured body part is appropriately encompassed by the radiation beam. From such measurements, the contour determiner 211 determines an optimum initial gantry angle of rotation displayed in output field 216 to optimize delivery of radiation to the breast. That is, defined/determined is the desired gantry angle for the medial M and lateral radiation beams Lr having field edges positioned along the tangential line $T_1$, which are displayed in the output display field 217 (FIG. 23) along with the determined contour Cr. Further, according to an embodiment of the contour determiner 211, determined and displayed automatically are the off-plane distance shown numerically in output field 218 and graphically in output field 219, along with "drop" and "shift" parameters shown in output fields 220, 221, respectively which indicate required movement of the rotating treatment table assembly 37 necessary to position the target T at the isocenter for the linear accelerator 31.

According to alternative embodiments of the contour determiner 211, additional contours or other data and other axial planes can be collected and recorded; and input fields or external application interfaces can be included to allow entry of additional setup data tailored to a specific contoured body part of a patient P. Additionally, gantry angle optimization can be incorporated to allow for the selection by the contour determiner 211 of gantry angles and other setup data that results in even numbers of monitor units and/or reduction of the number of segments, to provide ease of physical achievement by the therapist in the radiation delivery room. Further, a companion application can be used to enhance verification that the setup parameters, preferably also including the contour Cr, to match those collected in the simulation room.

A shown in FIGS. 1-29, embodiments of the present invention also including methods to facilitate and verify proper target alignment for radiation delivery so that a treatment plan can be more accurately applied to a patient. Note, for illustrative purposes, the following methods will be described with respect to the linear accelerator 31 shown in FIG. 1. Other radiation delivery apparatus are, however, within the scope of the present invention.

As perhaps best shown in FIGS. 1, 11-12, and 24, according to an embodiment of the present invention, provided is a method of determining and displaying a source-to-surface distance SSD between a theoretical point source TPS of a radiation delivery apparatus, e.g., linear accelerator 31, and a selected surface point position $S_1$ on a patient P. The method includes receiving a predetermined three-dimensional coordinate position of isocenter 40 for the linear accelerator 31 (block 301). The linear accelerator 31 includes a rotating gantry assembly 35 having a plane of rotation Pr and axis of rotation G and carrying a collimator 33 having a theoretical point source TPS. The distance between the theoretical point source TPS and the isocenter defines a source-to-axis distance SAD (see FIG. 11). Such source-to-axis distance SAD is preferably received and stored in the memory 123 of a target alignment analyzing computer 61 (block 303). A user, provided with a trackable body (block 305) such as, for example, trackable body 75 (FIG. 7A-B), described previously, positions the trackable body 75 such that an associated trackable body reference point 85 is positioned adjacent a selected patient surface (block 307). A trackable body detector 53 detects indicators 90 positioned on the trackable body 75 and, in conjunction with a trackable body position determiner 55, can determine a three-dimensional coordinate position of the trackable body reference point 85. Note, trackable body position determiner and the target alignment analyzing computer 61 can be functionally combined into a single unit or distributed over multiple units.

Figure 13A:
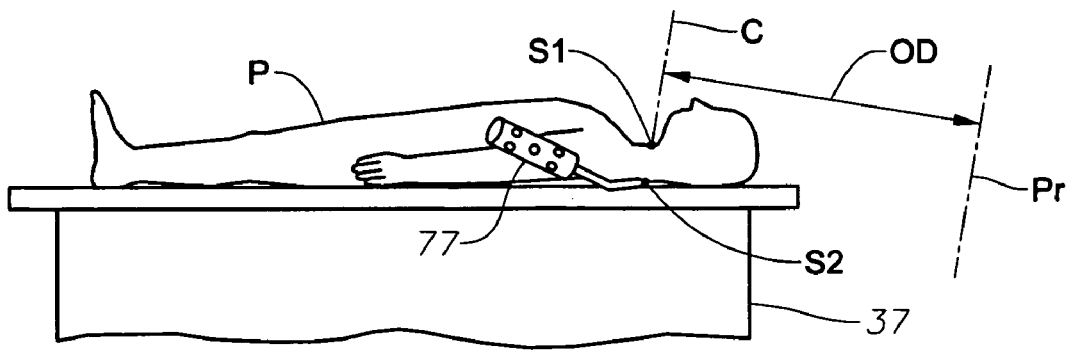
FIG. 13A is a perspective view of a portion of a system to facilitate and verify proper target alignment for radiation delivery according to an embodiment of the present invention.
Figure 13B:
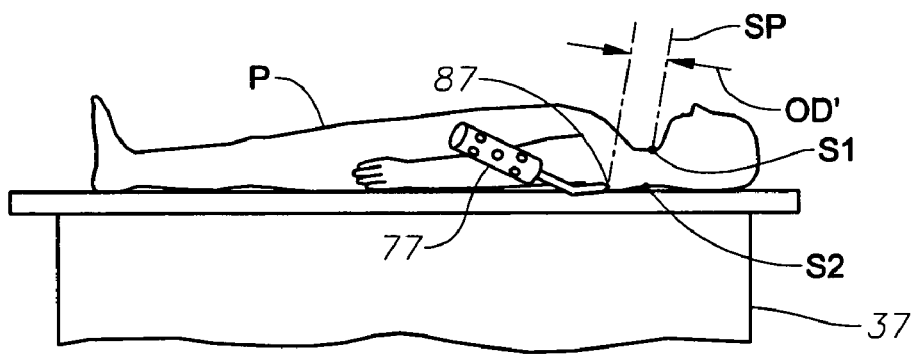
FIG. 13B is a perspective view of a portion of a system to facilitate and verify proper target alignment for radiation delivery according to an embodiment of the present invention.
Figure 14:
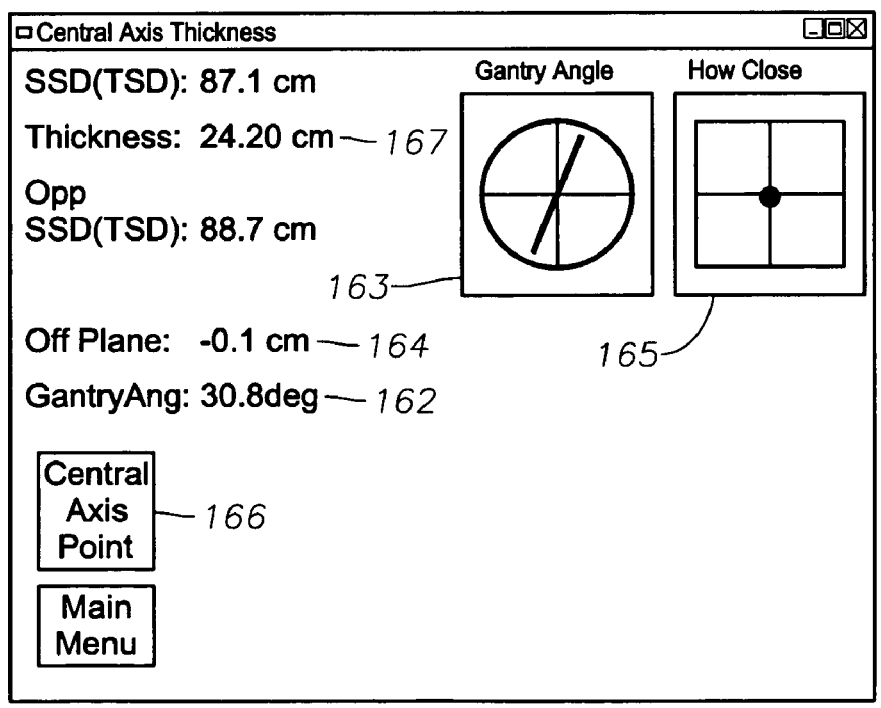
FIG. 14 is a schematic diagram of a graphical user interface for a system to facilitate and verify proper target alignment for radiation delivery according to an embodiment of the present invention.

The method also includes tracking the trackable body 75 with an optically trackable body detector 53 to determine a three-dimensional coordinate position of the trackable body reference point 85 (block 309), and determining, using a trackable body position determiner 55 and responsive to the tracking, the three-dimensional coordinate position of the trackable body reference point 85 (block 311) preferably with respect to the isocenter when adjacent the patient surface defining a surface point position $S_1$ (see, e.g., FIGS. 13A-B). The method also includes determining, responsive to determining the surface point position $S_1$ and receiving the source-to-axis distance SAD, a component of a distance within the plane of rotation Pr of the rotating gantry assembly 35 between the theoretical point source TPS of the collimator 33 and the surface point position $S_1$ defining a source-to-surface distance SSD; and displaying to a user the source-to-surface distance SSD on a computer display, such as, for example, display 127 or 129 (block 313).

The method can further include preventing one of the indicators 90 from being visible to the trackable body detector 53 to thereby interrupt either tracking of the optically trackable body 79 and/or displaying the source-to-surface distance SSD. The position determiner software or program product 119 stored in the memory 117 of the trackable body position determiner 55 can be set by the operator to respond to a selected number of indicators 90 such that interruption of an indicator provides such switching functionality. Further, as described previously, the trackable body 79 can include a manual switch 104 to allow masking and unmasking of one or more of the indicators 90. This inclusion of switching functionality can also be included with other methods, described later.

The method can additionally include determining, in response to determining the surface point position $S_1$, a gantry angle of rotation of the rotating gantry assembly 35 (block 315) that positions a central axis C of the collimator 33 simultaneously through the surface point position $S_1$ and the isocenter of the linear accelerator 31; and graphically displaying a representation of the determined gantry angle of rotation A. The method can further include determining, in response to the determined surface point position $S_1$, an off-plane (offset) distance OD between the surface point position $S_1$ and the plane of rotation Pr for the rotating gantry assembly (block 317), and graphically displaying the off-plane distance OD. The method preferably also includes moving a target T normal to the plane of rotation Pr for the rotating gantry assembly 35 (block 319) in response to determining the off-plane distance OD, to position the target T within the plane of rotation Pr of the rotating gantry assembly 35, to thereby align the target T for radiation delivery.

As perhaps best shown in FIGS. 1, 13A-14, and 25, according to an embodiment of the present invention, provided is a method of determining and displaying a patient thickness of a patient along an axis extending between a pair of opposite surface point positions and through the target T of a patient P. The method include selecting a first surface point position $S_1$, as described above (see blocks 301-311) but preferably using the trackable body such as, for example, trackable body 77. The method also includes determining a rotating gantry assembly angle of rotation A that positions or would position the central axis C of the collimator 33 simultaneously through the first surface point position $S_1$ and the isocenter, assuming the target T to be located at isocenter (block 341). The method also can include displaying graphically visual indicia of the rotating gantry assembly angle of rotation A (block 343), to thereby aid a user in locating a second surface point position $S_2$ on a second patient surface located opposite the first patient surface. The method can also include determining and preferably displaying the source-to-surface distance SSD to the first surface point position $S_1$, as described above (see block 313).

The method also includes providing to a user, responsive to tracking the position of the trackable body reference point 87, visual feedback to aid the user in positioning the trackable reference body reference point 87 adjacent the second surface point position $S_2$ on the second opposite patient surface of the patient P located along the rotating gantry assembly angle of rotation A (block 345). Methods of providing such visual feedback can include, for example, determining, responsive to the tracking, a plurality of positions of the trackable body reference point 87 preferably with respect to the isocenter; determining, responsive to determining the plurality of positions of the trackable body reference point 87, a corresponding plurality of off-plane distances OD between each of the plurality of positions of the trackable body reference point 87 and the rotating gantry assembly plane of rotation Pr; and displaying sequentially each of the plurality of off-plane distances OD to aid the user in positioning the trackable body reference point 87. Methods of providing such visual feedback can also include, for example, determining and displaying, responsive to determining the plurality of positions of the trackable body reference point 87, a corresponding plurality of off-plane distances OD' between each of the plurality of positions of the trackable body reference point 87 and a plane SP including the three-dimensional coordinate position of the first and second surface point positions $S_1$, $S_2$.

The method further includes determining, in response to the user positioning the trackable reference body reference point 87 adjacent the second patient surface, a three-dimensional coordinate position of the second surface point position $S_2$ (block 347). The method can also include determining the source-to-surface distance SSD for the second surface point position $S_2$ (block 349), as described with respect to the first surface point position $S_1$. The method further includes determining and displaying a patient thickness of the patient along the central axis C as would be when positioned between the first and the second surface point positions $S_1$, $S_2$, and simultaneously through the target T of the patient P when positioned at isocenter (block 351), to thereby facilitate and verify proper target alignment. This is preferably accomplished using the pair of source-to-surface distances SSD for the respective first and second surface point positions $S_1$, $S_2$ and the predetermined source-to-axis distance SAD, or alternatively using the first and the second surface point positions $S_1$, $S_2$, themselves.

As perhaps best shown in FIGS. 1, 15-16, and 26, according to an embodiment of the present invention, provided is a method of determining and displaying a patient thickness of a patient along a preselected (preferably vertical) emitter rotating assembly angle of rotation for an emitter rotating assembly, e.g. linear accelerator 31, extending from a first surface point position of a patient P. The method includes selecting a first surface point position $S_1$, as described above (see blocks 301-311), but preferably using the trackable body such as, for example, trackable body 77, and either providing or preselecting a rotating gantry assembly angle of rotation A at compile time or run-time, that positions or would position the central axis C of the collimator 33 through the first surface point position $S_1$ at the preselected angle of rotation A (block 361). The method can also include determining and preferably displaying the source-to-surface distance SSD for the first surface point position $S_1$, as described above (see block 313). According to one embodiment of the method, the method also can include displaying graphically, visual indicia of the preselected rotating gantry assembly angle of rotation A, to thereby aid the user in locating a third surface point position $S_3$ on a second patient surface located opposite the first patient surface.

The method also includes providing to the user, responsive to tracking the position of the trackable body reference point 87, visual feedback to aid the user in positioning the trackable reference body reference point 87 adjacent the third surface point position $S_3$ on the second opposite patient surface of the patient P located along the preselected rotating gantry assembly angle of rotation A (block 363). Methods of providing such visual feedback can include, for example, determining and displaying, responsive to the determined plurality of positions of the trackable body reference point 87, a corresponding plurality of off-plane distances OD" between each of the plurality of positions of the trackable body reference point 87 and a plane SP' characterized by including the three-dimensional coordinate position of the first and third surface point positions $S_1$, $S_3$.

The method further includes determining, in response to the user positioning the trackable reference body reference point 87 adjacent the second patient surface, a three-dimensional coordinate position of the third surface point position $S_3$ (block 365). The method can also include determining the source-to-surface distance SSD for the second surface point position $S_3$ (block 367), as described with respect to the first surface point position $S_1$. The method still further includes, preferably using the pair of source-to-surface distances SSD for the respective first and third surface point positions $S_1$, $S_3$ and the predetermined source-to-axis distance SAD or alternatively using the first and the third surface point positions $S_1$, $S_3$, themselves, determining and displaying a patient thickness of the patient between the first and the third surface point positions $S_1$, $S_3$, along the preselected rotating gantry angle of rotation A (block 369), to thereby facilitate and verify proper target alignment.

As stated previously, and as perhaps best shown in FIG. 17, the radiation beam provided by the collimator or other radiation emitter 33 can be divergent from the emitter central axis C upon entry into the patient P. Correspondingly, the radiation beam, positioned to provide radiation to the first surface point position $S_1$, may not exit the patient on the opposite surface of the patient P such as, for example, at a location coincident with a second surface point position $S_2$ aligned with a path of the emitter central axis C positioned to pass through the first and second point positions $S_1$, $S_2$ and the target T (FIG. 13A), or at a location coincident with a third surface point position $S_3$ aligned with a preselected path between the first and the third surface point positions $S_1$, $S_3$ based on a preselected or a predetermined gantry angle of rotation A (FIG. 15). Instead, due to the divergent nature of the radiation beam, the radiation beam will tend to emerge at a fourth off-axis surface point position $S_4$. Thus, in order to advantageously provide a more accurate dose calculation for such off-axis radiation delivery, blocks 345 and 347 and block 363 and 365 can be modified.

In response selecting/determining to the surface point position $S_1$ or other surface point position selected by the user and/or associated determined or predetermined/assumed gantry angle of rotation A, and in response to a preferably continuous flow of three-dimensional coordinate position data provided by the trackable body position determiner 55 for a trackable body reference point of one or more trackable bodies such as, for example, the trackable body 77, the method steps can alternatively include providing visual feedback to the user to aid the user in positioning the trackable reference body reference point 87 of the selected trackable body 77 adjacent an opposite surface of the patient P located along an arc approximating beam field divergence of the radiation beam, to determine the fourth surface point position $S_4$. The patient thickness is then determined along the arc between the first and the fourth surface point positions $S_1$, $S_4$, rather than utilizing a straight-line distance between points. Such thickness calculations (not shown), known to those skilled and art, can be used to substitute those described with respect to FIGS. 14 and 16. The source-to-surface distance SSD for the off-axis surface point position $S_4$ can also be determined and displayed, accordingly. This feature is particularly useful where radiation delivery is from a single beam.

As perhaps best shown in FIGS. 1, 18-19, and 27, according to embodiments of the present invention, provided is a method of determining and displaying a distance from a first selected surface point position $S_1$ to the current position of the trackable body reference point, e.g., trackable body reference point 85 of a trackable body 75. That is, the method includes providing trackable body 75 (block 381) and positioning the trackable body reference point 85 adjacent a first surface of the patient P (block 383), and, preferably, either through use a switch on the trackable body 75 or through use of a software/program product controlled switch, selecting the contacted point on the first surface of the patient to be the first surface point position $S_1$, to determine such first surface point position $S_1$ (block 385). As described previously, such tracking and determination is made through use of a trackable body detector 53 and trackable body position determiner 55. The method also includes tracking (block 387) the position of the trackable body reference point 85 using the trackable body detector 53 and trackable body position determiner 55 (see FIG. 1), in response to such identification or determination of the first surface point position $S_1$. Also, in response to the trackable body reference point positional data, the trackable body position determiner 55 substantially continuously determines and can display the three-dimensional coordinate position of the trackable body reference point 85. Correspondingly, the method can include substantially continuously determining and displaying the distance between the first surface point position $S_1$ and the three-dimensional coordinate position the trackable body reference point 85 (block 389). Thus, by placing the trackable body reference point 85 adjacent a surface of the patient P, the user is provided substantially instantaneously a coordinate of a surface point position and the distance to that surface point position to or from the first surface point positions $S_1$.

As shown in FIGS. 1, 20-21, and 28, according to an embodiment of the present invention, provided is a method of determining and displaying a table of surface point positions for multiple preferably pre-defined surface locations, which provide the user an ability to verify patient position over multiple sample locations. The method includes providing a trackable body, e.g., trackable body 75 (block 401) having a plurality of separate and spaced-apart optical indicators 90 each connected thereto at a separate preselected position and having a preselected trackable body reference point 85. The method also includes positioning the trackable body reference point 85 adjacent a plurality of selected patient surfaces of a patient P (block 403), and tracking, with an trackable body detector 53, the position of a subset of the plurality of separate and spaced-apart optical indicators 90 when visible to the optically trackable body detector 53, to determine a plurality of positions of the preselected trackable body reference point 85 (block 405).

The method can also include determining (block 407), responsive to tracking the plurality of positions of the preselected trackable body reference point 85, a respective plurality of surface point positions $S_1$-$S_n$. The method further includes, in response to determining the plurality of surface point positions $S_1$-$S_n$, forming and displaying (block 409) a point collection table (FIG. 21) including a three-dimensional coordinate point location for each of the plurality of surface point positions $S_1$-$S_n$, to thereby ensure proper patient positioning. Still further, the method can include determining and displaying source-to-surface distances SSDs in the point collection table. Example methods of determining such source-to-surface distances SSDs were described previously (see, e.g., block 313). Such methods can also alternatively include determining and displaying off-axis source-to-surface distance, as described previously.

As shown in FIGS. 1, 22-23, and 29, according to an embodiment of the present invention, provided is a method of determining and displaying an optimum emitter angle and beam width of a radiation delivery apparatus to enhance delivery of radiation to the contoured body part, e.g., chin or breast (shown in FIGS. 22-23). The method includes providing a trackable body, e.g., trackable body 79 (block 421) having a plurality of separate and spaced-apart optical indicators 90 each connected thereto at a separate preselected position and having a preselected trackable body reference point 89. The method also includes positioning the trackable body reference point 85 adjacent a selected contoured surface Cr of a contoured body part of a patient P (block 423). The method further includes tracking the trackable body 79 with an optically trackable body detector 53 preferably by tracking the position of a subset of the plurality of separate and spaced-apart optical indicators 90 when visible to the optically trackable body detector 53 (block 425), to determine a plurality of three-dimensional coordinate positions of the preselected trackable body reference point 89.

The method can also include determining (block 427), responsive to the tracking, two three-dimensional coordinate positions of the preselected trackable body reference point 89 when adjacent a corresponding two selected separate and spaced apart patient surface (setup) point positions, e.g., positions $C_1$, $L_1$ (see FIGS. 22-23); and forming (block 429), responsive to determining the pair of setup points $C_1$, $L_1$, a point-to-point line $T_1$ between the pair of setup points $C_1$, $L_1$, to thereby determine a radiation beam field edge boundary or edge of beam field. For a breast setup, illustrated in FIGS. 22-23, the setup points $C_1$, $L_1$ are preferably selected and marked with a tattoo (not shown). The point-to-point line $T_1$ forms a tangent to the patient's chest and defines the desired proximal edge of the beam field for the radiation beam.

The method also includes determining, responsive to the tracking, the plurality of three-dimensional coordinate positions of the preselected trackable body reference point 89 when translated adjacent or along the contoured surface Cr of the patient P to define a respective plurality of surface point positions representing the contour (block 431). The contoured surface Cr is preferably characterized by lying in the plane of rotation Pr of the rotating gantry assembly 35 and can, for example, be identified either through use of a tattoo or through use of lasers (not shown). The method also includes forming (block 433) a representation of the contour of the contoured surface Cr of the patient P (see FIG. 23), in response to determining the plurality of surface point positions representing the contoured surface Cr. The method also includes determining, in response to the above described measurements, an optimum beam width and direction that provides sufficient radiation to a target T positioned or to be positioned at isocenter, that has field edge boundaries that extend along the tangential line $T_1$, and that is wide enough to provide sufficient "flash" F to ensure desired radiation beam coverage of the contoured body part of the patient P. The method can further include providing to the user "drop" and "shift" parameters indicating required movement of the rotating treatment table assembly 37 to properly position the target T at isocenter.

Still further, depending on the level of treatment planning previously performed, the formed contour can be compared to that of such treatment plan (block 437). Further, such comparison can include comparing the determined beam width and direction (see FIG. 23). Such comparison can also or alternatively include first determining a patient thickness of the patient P at the plurality of surface point positions along a length of the contoured surface Cr, preferably using method steps such as, for example, those described with respect to blocks 301-313 and/or blocks 341-351, and comparing such determined patient thicknesses to respective thicknesses at corresponding surface point positions along the contoured surface Cr as defined and stored in the treatment plan, to thereby determine if patient translation is required.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include: nonvolatile, hard-coded type media such as read only memories (ROMs) or erasable, electrically programmable read only memories (EEPROMs), recordable type media such as floppy disks, hard disk drives and CD-ROMs, and transmission type media such as digital and analog communication links.

As shown in FIGS. 1-29, embodiments of the present invention also include a computer readable medium that is readable by a computer to facilitate and verify proper target alignment for radiation delivery so that a treatment plan can be more accurately applied to a patient P. For example, according to an embodiment of the present invention, provided is a computer readable medium that is readable by a computer to determine and display to a user a source-to-surface distance SSD between a theoretical point source TPS of a radiation delivery apparatus (e.g., linear accelerator 31) and a selected surface point position $S_1$ on a patient P. The linear accelerator 31 preferably includes a rotating gantry assembly 35 having a plane of rotation Pr and axis of rotation G and carrying a collimator 33 having a theoretical point source TPS and a central axis directed at an isocenter 40 for the linear accelerator 31. The computer readable medium includes a set of instructions that, when executed by the computer, such as, for example, target alignment analyzing computer 61 and/or trackable body position determiner 55, cause the computer to perform the operations of: tracking a trackable body, e.g., trackable body 75 having trackable by reference point 85; and determining, responsive to the tracking, the three-dimensional coordinate position of the trackable body reference point 85 when adjacent a patient surface defining a surface point position $S_1$. The instructions further include those to perform the operations of determining a component of a distance within the plane of rotation Pr of the rotating gantry assembly 35 between the theoretical point source TPS of the collimator 33 and the surface point position $S_1$ defining a source-to-surface distance SSD (see, e.g., FIG. 12), responsive to determining the surface point position $S_1$; and providing data to display to a user the source-to-surface distance SSD on a computer display, such as, for example, display 127 or 129.

Still further, the instructions can include those to perform the operations of determining a gantry angle of rotation A of the rotating gantry assembly 35 that positions a central axis C of the collimator 33 simultaneously through the surface point position $S_1$ and the isocenter (target) of the linear accelerator 31 in response to determining the surface point position $S_1$; providing data to graphically display a representation of the determined gantry angle of rotation A; determining an off-plane (offset) distance OD between the surface point position $S_1$ and the plane of rotation Pr for the rotating gantry assembly, in response to determining the surface point position $S_1$; and provide data to graphically display the off-plane distance OD.

According to an embodiment of the present invention, provided is a computer readable medium that is readable by a computer to determine and cause to display to a user a thickness between two opposing surface position points $S_1$, $S_2$ located on either side of the target T along a path of the emitter central axis C (FIG. 13A). The computer readable medium includes a set of instructions that, when executed by the computer, such as, for example, target alignment analyzing computer 61 and/or trackable body position determiner 55, cause the computer to perform the operations of: tracking a trackable body to determine a three-dimensional coordinate position of the trackable body reference point associated with trackable body; determining a first surface point position $S_1$, responsive to the tracking; and determining a source-to-surface distance SSD to the first surface point position $S_1$, according to methods described previously, but preferably using a trackable body such as, for example, trackable body 77, having a trackable body reference point 87.

The instructions also include those to perform the operations of: determining a rotating gantry assembly angle of rotation A that positions or would position the central axis C of the collimator 33 simultaneously through the first surface point position $S_1$ and the isocenter 40, assuming the target T to be located at isocenter; and on a computer display such as, for example, display 127 or 129, forming for display, responsive to tracking the position of the trackable body reference point 87, a representation of a location of the trackable body reference point 87 relative to a second surface point position $S_2$ on a second opposite patient surface of the patient along the emitter rotating assembly angle of rotation A, to thereby provide visual feedback to aid the user in positioning the trackable reference body reference point 87 adjacent the second surface point position $S_2$. Note, providing such visual feedback can include but is not limited to performing the operations of: providing data to a video display to display sequentially to the user off-plane distances OD between each of the positions of the trackable body reference point 87 and the rotating gantry assembly plane of rotation Pr (see FIG. 13A); providing data to a video display to display a plurality of off-plane distances OD' between each of the plurality of positions of the trackable body reference point 87 and a plane SP (see FIG. 13B) passing through the three-dimensional coordinate position of the first and second surface point positions $S_1$, $S_2$; and/or providing data to a video display to display numerically or graphically the rotating gantry assembly angle of rotation A. Data to display the source-to-surface distance SSD to the first surface point position $S_1$ can also be provided.

The instructions also include those to perform the operations of determining and preferably providing data to display a three-dimensional coordinate position of the second surface point position $S_2$, in response to the user positioning of the trackable reference body reference point 87 adjacent the second patient surface of the patient P; and determining and providing data to display a patient thickness of the patient along the central axis C as would be when positioned between the first and the second surface point positions $S_1$, $S_2$, and simultaneously through the target T of the patient P when positioned at isocenter. This is preferably accomplished by either determining a difference between the sum of the distances of the pair of source-to-surface distances SSD for the respective first and second surface point positions $S_1$, $S_2$ and twice the value of the predetermined source-to-axis distance SAD, or alternatively by determining a straight-line distance between the first and the second surface point positions $S_1$, $S_2$. The necessary mathematical algorithms to perform such determination are known to those skilled in the art.

According to an embodiment of the present invention, provided is a computer readable medium that is readable by a computer to determine and cause to display to a user a thickness of a patient along a preselected (preferably vertical) emitter rotating assembly angle of rotation for an emitter rotating assembly, e.g. linear accelerator 31, extending from a first surface point position $S_1$ of a patient P. The computer readable medium includes a set of instructions that, when executed by the computer, such as, for example, target alignment analyzing computer 61 and/or trackable body position determiner 55, cause the computer to perform the operations of: tracking a trackable body 77 to determine a three-dimensional coordinate position of the trackable body reference point associated with trackable body; determining a first surface point position $S_1$, responsive to such tracking; and determining a source-to-surface distance SSD for the first surface point position $S_1$, preferably according to methods described above.

The instructions also include those to perform the operations of: either providing or preselecting a rotating gantry assembly angle of rotation A, at compile time or run-time, that positions or would position the central axis C of the collimator 33 through the first surface point position $S_1$ at the preselected angle of rotation A; and forming, responsive to tracking the position of the trackable body reference point 87, a representation of a location of the trackable body reference point 87 relative to a third surface point position $S_3$ on a second opposite patient surface of the patient P along the preselected rotating assembly angle of rotation A, to thereby provide visual feedback to aid the user in positioning the trackable reference body reference point 87 adjacent the third surface point position $S_3$. Note, providing such visual feedback can include but is not limited to performing the operations of: determining and providing data to display a corresponding plurality of off-plane distances OD" between each of a plurality of positions of the trackable body reference point 87 and a plane SP' characterized by including the three-dimensional coordinate position of the first and third surface point positions $S_1$, $S_3$ (see FIG. 15), in response to determining the plurality of positions of the trackable body reference point 87.

The instructions can also include those to perform the operations of: determining a three-dimensional coordinate position of the third surface point position $S_3$, in response to the user positioning the trackable reference body reference point 87 adjacent the second patient surface; determining the source-to-surface distance SSD for the third surface point position $S_3$, as described with respect to the first surface point position $S_1$; and determining and providing data to display a patient thickness of the patient between the first and the third surface point positions $S_1$, $S_3$, along the preselected rotating gantry angle of rotation A, preferably using the pair of source-to-surface distances SSD for the respective first and third surface point positions $S_1$, $S_3$ and the predetermined source-to-axis distance SAD, or alternatively using, for example, the first and the third surface point positions $S_1$, $S_3$.

Note, according to an embodiment of the present invention, the instructions can include those to perform the above described operations with the inclusion of applying consideration of beam field divergence in the applicable algorithms used to determine the location of the opposite side surface point position, shown as $S_4$ in FIG. 17, and the patient thickness between the pair of surface points. That is, the opposite side surface point position and the patient thickness is determined along the arc between the first and the fourth surface point positions $S_1$, $S_4$, rather than along a straight-line distance between surface point positions $S_1$, $S_4$. The source-to-surface distance SSD for the off-axis surface point position $S_4$ can also instead be determined and displayed. These features are particularly useful where radiation delivery is from a single beam.

According to an embodiment of the present invention, also provided is a computer readable medium that is readable by a computer to determine and cause to display to a user a distance from a first selected surface point position $S_1$ to the current position of a trackable body reference point, e.g., trackable body reference point 85 of a trackable body 75. The computer readable medium includes a set of instructions that, when executed by the computer, such as, for example, target alignment analyzing computer 61 and/or trackable body position determiner 55, cause the computer to perform the operations of: tracking a position of a subset of a plurality of separate and spaced-apart optical indicators positioned on the trackable body 75, to determine a plurality of positions of a preselected trackable body reference point 85 associated with the trackable body 75; and determining the three-dimensional coordinate position of the trackable body reference point 85 when adjacent the patient surface defining a first surface point position $S_1$, in response to tracking and the user positioning of the trackable body 75, and in response to identification of the location of the surface point position $S_1$. The identification can be provided through use of either a manual switch on the trackable body 75 or through use of a software/program product controlled switch. Correspondingly, the instructions can include those to perform the operations of storing a current position of the trackable body reference point 85 in response to activation of such switch.

The instructions also include those to perform the operations of: substantially continuously determining a point-to-point distance 195 (see FIG. 19) between first surface point position $S_1$ and a current position of the preselected trackable body reference point 85, responsive to the tracking and the determining of the first surface point position $S_1$; and providing data to display the point-to-point distance to the user on a computer display such as, for example, display 127 or 129. Thus, by placing the trackable body reference point 85 adjacent a surface of the patient P, the user is provided, substantially instantaneously, a coordinate of a surface point position and the distance to that surface point position to or from the first surface point positions $S_1$.

According to an embodiment of the present invention, provided is a computer readable medium that is readable by a computer to cause the display to a user of a table of surface point positions for multiple preferably pre-defined surface locations (see FIG. 21). The computer readable medium includes a set of instructions that, when executed by the computer, such as, for example, target alignment analyzing computer 61 and/or trackable body position determiner 55, cause the computer to perform the operations of: tracking a position of a subset of a plurality of separate and spaced-apart optical indicators positioned on the trackable body 75, to determine a plurality of positions of a preselected trackable body reference point 85; and determining, responsive to the tracking, the plurality of positions of the preselected trackable body reference point 85 when adjacent a corresponding plurality of separate and spaced apart patient surfaces located at pre-selected points to define a respective plurality of surface point positions $S_1$-$S_n$. The identification of the plurality of surface point positions can be provided through use of either a manual switch on the trackable body 75 or through use of a software/program product controlled switch. Correspondingly, the instructions can include those to perform the operations of storing a current position of the trackable body reference point 85, in response to activation of such switch. The instructions can further include those to perform the operations of: forming a point collection table including a three-dimensional coordinate point location for each of the plurality of surface point positions $S_1$-$S_n$, responsive to determining the plurality of surface point positions $S_1$-$S_n$; and providing data to display the point collection table (FIG. 21) to the user on a computer display such as, for example, display 127 or 129.

According to an embodiment of the present invention, provided is a computer readable medium that is readable by a computer to determine and cause to display an optimum emitter angle and beam width of a radiation delivery apparatus to enhance delivery of radiation to a contoured body part. The computer readable medium can include a set of instructions that, when executed by the computer, such as, for example, target alignment analyzing computer 61 and/or trackable body position determiner 55, cause the computer to perform the operations of: tracking a trackable body, e.g. trackable body 79 preferably by tracking the position of a subset of the plurality of separate and spaced-apart optical indicators 90, to determine a plurality of three-dimensional coordinate positions of the preselected trackable body reference point 89; determining two three-dimensional coordinate positions of the preselected trackable body reference point 89 when adjacent a corresponding two selected separate and spaced apart patient surface (setup) point positions, e.g., positions $C_1$, $L_1$ (FIG. 22), responsive to the tracking (see FIGS. 22-23); and forming a point-to-point line $T_1$ between the pair of setup points $C_1$, $L_1$, responsive to determining the pair of setup points $C_1$, $L_1$, to thereby determine a radiation beam field edge boundary or edge of beam field.

The instructions can include those to perform the operations of: determining the plurality of three-dimensional coordinate positions of the preselected trackable body reference point 89, responsive to the tracking and responsive to the user translating the trackable body reference point 89 adjacent or along the contoured surface Cr of the patient P to define a respective plurality of surface point positions representing the contour of the contoured surface Cr; and forming a representation of the contour of the contoured surface Cr of the patient P (see FIG. 23), in response to determining the plurality of surface point positions representing the contoured surface Cr. The instructions also include those to perform the operations of determining an optimum beam width and direction, in response to the above described measurements, that provides sufficient radiation to a target T positioned or to be positioned at isocenter, that has field edge boundaries that preferably extend along the line $T_1$, and that is wide enough to provide sufficient "flash" F to ensure desired radiation beam coverage of the contoured body part of the patient P. The amount of desired "flash" F is preferably defined by the user.

The instructions can further include those to perform the operation of providing data to display to the user "drop" and "shift" parameters 220, 221, indicating required movement of a rotating treatment table assembly 37 to properly position the target T at the isocenter 40 when used in conjunction with a linear accelerator 31 or other such apparatus. Still further, the instructions can include those to perform the operations of: comparing the formed contour to that associated with a predetermined treatment plan. Such comparison can include: comparing the determined beam width and direction (see FIG. 23); and determining and comparing a patient thickness of the patient P at the plurality of surface point positions along a length of the contoured surface Cr to respective thicknesses at corresponding surface point positions along the contoured surface Cr as defined or stored in the treatment plan.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the attached claims. For example, the delivery apparatus was described and illustrated in the form of a linear accelerator. The invention, however, is not limited to such apparatus and can be used with any apparatus having at least one assembly carrying an emitter directed to an isocenter of the delivery apparatus. Also for example, the trackable body position determiner was illustrated as a single piece of computer hardware having memory and position determiner program product, however, the determiner and/or functions of the determiner and the position determiner program product can be installed in the trackable body detector, in the illustrated trackable body position determiner, in both, or in the target alignment analyzing computer or in combination thereof. Further, the target alignment analyzing program product can be independently stored in a mobile storage media, such as, a compact disc, portable hard drive, etc., or be located on separate pieces of storage media for loading on separate components.

That claimed is:

1. A system to facilitate and verify proper target alignment for radiation delivery so that a treatment plan can be more accurately applied to a patient, the system comprising:

an application computer having memory associated therewith;

a treatment plan stored in the memory of the application computer to provide planned radiation treatment delivery instructions to deliver radiation treatment to a patient;

a radiation delivery apparatus in communication with the application computer to provide radiation treatment to the patient, the radiation delivery apparatus including a radiation emitter adapted to emit a radiation beam having a theoretical point source and central beam axis, a controller responsive to the treatment delivery instructions to control delivery of the radiation beam to the patient, and a plurality of rotating assemblies each being adapted to direct the radiation beam through a target of the patient and each having a rotational path in a distinct plane and an axis of rotation, the axis of rotation of each of the plurality of rotating assemblies intersecting the axis of rotation of each other rotating assembly of the plurality of rotating assemblies at a three-dimensional coordinate to define an isocenter of an isocenter coordinate system of the radiation delivery apparatus, the theoretical point source being a predetermined distance from the isocenter to define a source-to-axis distance, the radiation emitter connected to one of the plurality of rotating assemblies so that the one of the plurality of rotating assemblies defines an emitter carrier rotating assembly;

an optically trackable body having a trackable body origin positioned within a preselected coordinate system assigned thereto, a trackable body reference point positioned with respect to the preselected coordinate system, and a plurality of separate and spaced-apart optical retro-reflective indicators each connected at a separate preselected position thereon to thereby indicate a position of the trackable body reference point;

a trackable body detector having a detector body adapted to be positioned separate and spaced apart from the optically trackable body at a three-dimensional trackable body detector reference location, and including a pair of separate and spaced apart optical receivers connected to the detector body, each of the optical receivers having a field of view and being adapted to receive optical energy reflected by each of a plurality of optical retro-reflective indicators when positioned in the field of view to thereby detect a three-dimensional position of each of the plurality of optical retro-reflective indicators when positioned simultaneously within the field of view of both of the optical receivers to produce a plurality of position signals representing such three-dimensional indicator positions, and a first illuminator positioned adjacent one of the pair of separate and spaced apart optical receivers and a second illuminator positioned adjacent the other of the pair of separate and spaced apart optical receivers to selectively illuminate each of the plurality of optical retro-reflective indicators when positioned in the field of view of the respective adjacent optical receiver to thereby energize the optical retro-reflective indicators within the field of view of the respective adjacent optical receiver;

a trackable body position determiner in communication with the trackable body detector and responsive to the plurality of position signals produced by the trackable body detector to determine a three-dimensional coordinate position of the trackable body reference point, the trackable body position determiner having memory associated therewith and position determiner program product stored therein, the position determiner program product being responsive to the plurality of position signals from the trackable body detector, to determine the three-dimensional coordinate position of the trackable body reference point when a preselected number of the plurality of retro-reflective indicators are simultaneously positioned within the field of view of both of the optical receivers of the trackable body detector and when positioned adjacent a surface of the patient to define a surface point position;

a target alignment analyzing computer in communication with the trackable body position determiner to determine proper target alignment for the radiation delivery apparatus and having a processor and memory coupled to the processor to store operating instructions, the three-dimensional coordinate position of the isocenter, and the source-to-axis distance of the radiation delivery apparatus, therein, and a display coupled to the processor to display target alignment data; and target alignment analyzing program product stored in the memory of the target alignment analyzing computer to facilitate and verify proper target alignment for radiation delivery, the target alignment analyzing program product including:

a source-to-surface distance determiner configured to receive the three-dimensional coordinate position of isocenter, the source-to-axis distance, and a first surface point position on a first surface of the patient to determine a component of a distance within the plane of rotation of the emitter carrier rotating assembly between the theoretical point source and the first surface of the patient to define a first source-to-surface distance, to thereby display the source-to-surface distance to a user of the system, an emitter carrier angle determiner configured to receive the three-dimensional coordinate position of isocenter and the first surface point position, to determine an angle of rotation of the emitter carrier rotating assembly that positions a path of the emitter central axis simultaneously through the first surface point position and the isocenter to define a first emitter carrier rotating assembly angle of rotation, an off-plane distance determiner configured to receive the determined first surface point position, to determine an off-plane distance between the first surface point position and the plane of rotation for the emitter carrier rotating assembly, the off-plane distance providing the user of the system a distance required to move a target normal to the plane of rotation for the emitter carrier rotating assembly to position the target within the plane of rotation of the emitter carrier rotating assembly, a central axis thickness determiner configured to receive the first surface point position and the first emitter carrier rotating assembly angle of rotation, and responsive to a three-dimensional coordinate position of the trackable body reference point of the optically trackable body determined by the trackable body position determiner, to provide visual feedback to the user of the system to aid the user in positioning the trackable body reference point adjacent a second surface of the patient opposite the first surface along the emitter central axis path defining the first emitter carrier rotating assembly angle of rotation and to determine a second surface point position located on the second surface to thereby determine a patient thickness along the emitter central axis between the first and the second surface point positions, a point-to-point distance determiner configured to receive the determined first surface point position and responsive to a three-dimensional coordinate position of the trackable body reference point of the trackable body determined by the trackable body position determiner, to determine a distance between the first surface point position and the three-dimensional coordinate position of the trackable body reference point to thereby provide patient surface relative positioning data, a point collection table former configured to receive a list of a plurality of pre-defined surface points, and responsive to a user sequentially positioning the trackable body reference point of the optically trackable body adjacent each of a plurality of surface point locations corresponding to the plurality of pre-defined surface points, to form a surface locations table including for each of the plurality of pre-defined surface points at least one of the following: a surface point position and a source-to-surface distance, to thereby ensure proper patient positioning, and a contour determiner configured to receive a plurality of surface point positions provided by the trackable body position determiner and responsive to user positioning of the trackable body reference point of the optically trackable body along a contour of a contoured human body part, to determine the contour of the contoured human body part and thereby determine an optimum emitter angle and beam width of the radiation delivery apparatus to enhance delivery of radiation to the contoured body part.

2. A system as defined in claim 1, wherein the determined first surface point position lies in a first surface point plane, and wherein the off-plane distance determiner is a first off-plane distance determiner, the target alignment analyzing program product further comprising:

a second off-plane distance determiner configured to receive the determined first surface point position, to determine an off-plane distance between the trackable body reference point and the first surface point plane, the off-plane distance providing the user a distance required to move the trackable body reference point normal to the first surface point plane to position the trackable body reference point adjacent the second surface of the patient at the second surface point position.

3. A system as defined in claim 1, wherein the first emitter carrier rotating assembly angle of rotation is a preselected angle, the target alignment analyzing program product further comprising:

a preselected angle thickness determiner configured to receive the determined first surface point position and responsive to tracking a three-dimensional coordinate position of trackable body reference point, to provide visual feedback to the user to aid the user in positioning the trackable body reference point adjacent a third surface of the patient opposite the first surface along the preselected angle and to determine a third surface point position located on the third surface, to thereby determine a patient thickness between the first and the third surface point positions.

4. A system as defined in claim 1, wherein the radiation beam is divergent from the emitter central axis between the first surface point position and a third surface point position, the target alignment analyzing program product further comprising:

an off-axis thickness determiner configured to receive the determined first surface point position and the first emitter carrier rotating assembly angle of rotation and responsive to tracking a three-dimensional coordinate position of trackable body reference point, to provide visual feedback to the user to aid the user in positioning the trackable body reference point adjacent a third opposite surface of the patient located along an arc approximating beam field divergence of the radiation beam and to determine a third surface point position located on the third surface, to thereby determine a patient thickness along the arc between the first and the third surface point positions.

5. A system as defined in claim 1, wherein the optically trackable body further comprises an optically trackable body extension including:

an elongated body having a proximal end portion, a distal end portion, and a medial body portion extending therebetween, the distal end portion including an annular recess; and a spherical body positioned within the annular recess adjacent the trackable body reference point, and adapted to contact a surface of the patient and to roll when manipulated along the surface of the patient to enhance movement of the optically trackable body when in contact with the surface of the patient, to thereby determine a plurality of successive surface point positions, the trackable body reference point located at a distal-most portion of the spherical body to continually reference a current surface position of the surface of the patient when the spherical body is being rotated in contact with the surface of the patient.

6. A system as defined in claim 1, wherein the plurality of rotating assemblies include a rotating patient treatment table assembly positioned adjacent the emitter carrier rotating assembly and having a substantially flat treatment table upper surface and adapted to allow positioning of the target of the patient with respect to the isocenter for radiation delivery; and wherein the optically trackable body includes a main body having a proximal body end portion, a distal body end portion, and a medial body portion extending therebetween having a longitudinal axis, and a flat-shaped extension member having a proximal end portion connected to the distal body end portion of the main body, a distal end portion, and a medial portion extending therebetween, the trackable body reference point located adjacent the distal end portion of the extension member, and the medial portion of the extension member having an obtuse angular bend with respect to the longitudinal axis of the main body portion to allow pivoting of the trackable body when positioned on a flat surface to thereby allow a user to manipulate the trackable body reference point into contact with a lower surface of the patient facing the upper surface of the rotating patient treatment table assembly, between the lower patient surface of the patient and the substantially flat upper surface of the treatment table assembly.

7. A system as defined in claim 5, wherein the optically trackable body further comprises:
a switch adapted to be manipulated by the user to mask at least one of the plurality of retro-reflective indicators to thereby disable provision of position data for the trackable body reference point, and adapted to be manipulated by the user to unmask the at least one of the plurality of retro-reflective indicators to thereby enable provision of position data for the trackable body reference point.

8. A system to facilitate and verify proper target alignment for radiation delivery so that a treatment plan can be more accurately applied to a patient, the system comprising:
a radiation delivery apparatus to provide radiation delivery to the patient, the radiation delivery apparatus including a radiation emitter adapted to emit a radiation beam having a theoretical point source and central beam axis and a rotating assembly carrying the radiation emitter to define an emitter carrier rotating assembly, the emitter carrier rotating assembly adapted to direct the radiation beam through a target of the patient and having a rotational path in a distinct plane and an axis of rotation to direct the radiation beam at a three-dimensional coordinate position defining an isocenter of an isocenter coordinate system of the radiation delivery apparatus, the theoretical point source being a predetermined distance from the isocenter to define a source-to-axis distance;
a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;
a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;
a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view of the trackable body detector, the trackable body position determiner having memory associated therewith and position determiner program product stored therein;
a target alignment analyzing computer in communication with the trackable body position determiner to determine proper target alignment for the radiation delivery apparatus, the target alignment analyzing computer having a processor and memory coupled to the processor to store operating instructions, the three-dimensional coordinate position of the isocenter, and the source-to-axis distance of the radiation delivery apparatus, therein, and a display coupled to the processor to display target alignment data; and
target alignment analyzing program product stored in the memory of the target alignment analyzing computer to facilitate and verify proper target alignment for radiation delivery, the target alignment analyzing program product comprising an optical distance indicator simulator, the optical distance indicator simulator including a source-to-surface distance determiner configured to receive the three-dimensional coordinate position of isocenter, the source-to-axis distance, and a three-dimensional coordinate position of a first surface point position on a first surface of the patient located outside a plane of rotation of the emitter carrier rotating assembly to determine an on-axis distance between the surface point position and the isocenter within the plane of rotation of the emitter carrier rotating assembly, and to determine a component of a distance within the plane of rotation of the emitter carrier rotating assembly between the theoretical point source and the first surface of the patient to define a source-to-surface distance responsive to the source to axis distance and the determined on-axis distance between the surface point position and the isocenter, to thereby provide the source-to-surface distance to a user of the system.

9. A system as defined in claim 8, wherein the target alignment analyzing program product further comprises:
an emitter carrier angle determiner configured to receive the three-dimensional coordinate position of isocenter and the surface point position and to determine and display on a graphical user interface an angle of rotation of the emitter carrier rotating assembly that positions a path of the emitter central axis simultaneously through the first surface point position and the isocenter to define an emitter carrier rotating assembly angle of rotation.

10. A system as defined in claim 8, wherein the target alignment analyzing program product further comprises:
an off-plane distance determiner configured to receive the determined first surface point position and to determine and display on a graphical user interface an off-plane distance between the first surface point position and the plane of rotation for the emitter carrier rotating assembly, the determined and displayed off-plane distance providing a user of the system a visual indication of a distance required to move a target normal to the plane of rotation for the emitter carrier rotating assembly to position the target within the plane of rotation of the emitter carrier rotating assembly.

11. A system to facilitate and verify proper target alignment for radiation delivery so that a treatment plan can be more accurately applied to a patient, the system comprising:
a radiation delivery apparatus to provide radiation delivery to the patient, the radiation delivery apparatus including a radiation emitter adapted to emit a radiation beam having a theoretical point source and central beam axis and a rotating assembly carrying the radiation emitter to define an emitter carrier rotating assembly, the emitter carrier rotating assembly adapted to direct the radiation beam through a target of the patient and having a rotational path in a distinct plane and an axis of rotation to direct the radiation beam at a three-dimensional coordinate position defining an isocenter of an isocenter coordinate system of the radiation delivery apparatus, the theoretical point source being a predetermined distance from the isocenter to define a source-to-axis distance;
a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;

a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;

a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view of the trackable body detector, the trackable body position determiner having memory associated therewith and position determiner program product stored therein;

a target alignment analyzing computer in communication with the trackable body position determiner to determine proper target alignment for the radiation delivery apparatus, the target alignment analyzing computer having a processor and memory coupled to the processor to store operating instructions, the three-dimensional coordinate position of the isocenter, and the source-to-axis distance of the radiation delivery apparatus, therein, and a display coupled to the processor to display target alignment data; and target alignment analyzing program product stored in the memory of the target alignment analyzing computer to facilitate and verify proper target alignment for radiation delivery, the target alignment analyzing program product comprising:

a source-to-surface distance determiner configured to receive a three-dimensional coordinate position of a first surface point position on a first surface of the patient, to determine a component of a distance within the plane of rotation of the emitter carrier rotating assembly between the theoretical point source and the first surface of the patient to define a source-to-surface distance, to thereby provide the source-to-surface distance to a user of the system, an emitter carrier angle determiner configured to receive the three-dimensional coordinate position of isocenter and the surface point position, to determine an angle of rotation of the emitter carrier rotating assembly that positions a path of the emitter central axis simultaneously through the first surface point position and the isocenter to define an emitter carrier rotating assembly angle of rotation, and a central axis thickness determiner configured to receive the first surface point position and the emitter carrier rotating assembly angle of rotation, and responsive to a three-dimensional coordinate position of the trackable body reference point of the trackable body determined by the trackable body position determiner, to provide visual feedback to a user of the system to aid the user in positioning the trackable body reference point adjacent a second surface of the patient opposite the first surface along the emitter central axis path defining the emitter carrier rotating assembly angle of rotation, and to determine a second surface point position located on the second surface, to thereby determine and display to the user of the system a patient thickness along the emitter central axis between the first and the second surface point positions.

12. A system to facilitate and verify proper target alignment for radiation delivery so that a treatment plan can be more accurately applied to a patient, the system comprising:

a radiation delivery apparatus to provide radiation delivery to the patient, the radiation delivery apparatus including a radiation emitter adapted to emit a radiation beam having a theoretical point source and central beam axis and a rotating assembly carrying the radiation emitter to define an emitter carrier rotating assembly, the emitter carrier rotating assembly adapted to direct the radiation beam through a target of the patient and having a rotational path in a distinct plane and an axis of rotation to direct the radiation beam at a three-dimensional coordinate position defining an isocenter of an isocenter coordinate system of the radiation delivery apparatus, the theoretical point source being a predetermined distance from the isocenter to define a source-to-axis distance;

a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;

a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;

a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view of the trackable body detector, the trackable body position determiner having memory associated therewith and position determiner program product stored therein;

a target alignment analyzing computer in communication with the trackable body position determiner to determine proper target alignment for the radiation delivery apparatus, the target alignment analyzing computer having a processor and memory coupled to the processor to store operating instructions, the three-dimensional coordinate position of the isocenter, and the source-to-axis distance of the radiation delivery apparatus, therein, and a display coupled to the processor to display target alignment data; and target alignment analyzing program product stored in the memory of the target alignment analyzing computer to facilitate and verify proper target alignment for radiation delivery, the target alignment analyzing program product comprising:

a source-to-surface distance determiner configured to receive a three-dimensional coordinate position of a first surface point position on a first surface of the patient, to determine a component of a distance within the plane of rotation of the emitter carrier rotating assembly between the theoretical point source and the first surface of the patient to define a source-to-surface distance, to thereby provide the source-to-surface distance to a user of the system, and a preselected angle thickness determiner configured to receive the determined first surface point position on the first surface and responsive to a plurality of three-dimensional coordinate positions of the trackable body reference point, to provide on a graphical user interface relative visual feedback to a user of the system to aid the user in manually positioning the trackable body reference point in contact with a second surface point position located on a second surface of the patient opposite the first surface point position along the preselected angle, to determine the location of the second surface point position on the second surface along the preselected angle, and to determine a patient thickness between the first and the second surface point positions along the preselected angle.

13. A system as defined in claim 12, wherein the determined first surface point position lies in a first surface point plane, the target alignment analyzing program product further comprising:
an off-plane distance determiner configured to receive the determined first surface point position and to determine and display on a graphical user interface an off-plane distance between the trackable body reference point and the first surface point plane, the determined and displayed off-plane distance providing the user of the system a visual indication of a distance required to move the trackable body reference point normal to the first surface point plane to position the trackable body reference point in contact with the second surface of the patient at the second surface point position.

14. A system to facilitate and verify proper target alignment for radiation delivery so that a treatment plan can be more accurately applied to a patient, the system comprising:
a radiation delivery apparatus to provide radiation delivery to the patient, the radiation delivery apparatus including a radiation emitter adapted to emit a radiation beam having a theoretical point source and central beam axis and a rotating assembly carrying the radiation emitter to define an emitter carrier rotating assembly, the emitter carrier rotating assembly adapted to direct the radiation beam along an emitter central axis path through a target of the patient between a first surface point position on a first surface of the patient and a second surface point position on a second opposite surface and having a rotational path in a distinct plane and an axis of rotation to direct the radiation beam at a three-dimensional coordinate position defining an isocenter of an isocenter coordinate system of the radiation delivery apparatus, the theoretical point source being a predetermined distance from the isocenter to define a source-to-axis distance the radiation beam being divergent from the emitter central axis path when directed between the first surface point position on the first surface and the second surface point position on the second opposite surface to result in the radiation beam exiting at a third surface point position on the second opposite surface;
a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;
a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;
a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view of the trackable body detector, the trackable body position determiner having memory associated therewith and position determiner program product stored therein;
a target alignment analyzing computer in communication with the trackable body position determiner to determine proper target alignment for the radiation delivery apparatus, the target alignment analyzing computer having a processor and memory coupled to the processor to store operating instructions, the three-dimensional coordinate position of the isocenter, and the source-to-axis distance of the radiation delivery apparatus, therein, and a display coupled to the processor to display target alignment data; and
target alignment analyzing program product stored in the memory of the target alignment analyzing computer to facilitate and verify proper target alignment for radiation delivery, the target alignment analyzing program product comprising:
a source-to-surface distance determiner configured to receive a three-dimensional coordinate position of a first surface point position on a first surface of the patient, to determine a component of a distance within the plane of rotation of the emitter carrier rotating assembly between the theoretical point source and the first surface of the patient to define a source-to-surface distance, to thereby provide the source-to-surface distance to a user of the system, and
an off-axis thickness determiner configured to receive the determined first surface point position on the first surface and responsive to a plurality of three-dimensional coordinate positions of the trackable body reference point, to provide on a graphical user interface relative visual feedback to the user to aid the user in manually positioning the trackable body reference point in contact with a second surface point position located on a second opposite surface of the patient located along an arc approximating beam field divergence of a projected radiation beam projected through the first surface point position at a certain angle, to determine the location of the second surface point position on the second surface located along the arc, and to determine a patient thickness along the arc between the first and the third surface point positions.

15. A system to facilitate and verify proper target alignment for radiation delivery so that a treatment plan can be more accurately applied to a patient, the system comprising:
a radiation delivery apparatus to provide radiation delivery to the patient, the radiation delivery apparatus including a radiation emitter adapted to emit a radiation beam having a theoretical point source and central beam axis and a rotating assembly carrying the radiation emitter to define an emitter carrier rotating assembly adapted to direct the radiation beam through a target of the patient and having a rotational path in a distinct plane and an axis of rotation to direct the radiation beam at a three-dimensional coordinate position defining an isocenter of an isocenter coordinate system of the radiation delivery apparatus, the theoretical point source being a predetermined distance from the isocenter to define a source-to-axis distance;

a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;

a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;

a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view of the trackable body detector, the trackable body position determiner having memory associated therewith and position determiner program product stored therein;

a target alignment analyzing computer in communication with the trackable body position determiner to determine proper target alignment for the radiation delivery apparatus, the target alignment analyzing computer having a processor and memory coupled to the processor to store operating instructions, the three-dimensional coordinate position of the isocenter, and the source-to-axis distance of the radiation delivery apparatus, therein, and a display coupled to the processor to display target alignment data; and target alignment analyzing program product stored in the memory of the target alignment analyzing computer to facilitate and verify proper target alignment for radiation delivery, the target alignment analyzing program product including a point-to-point distance determiner configured to determine and display a coordinate position of a first surface point position on graphical user interface responsive to a three-dimensional coordinate position of the trackable body reference point of the trackable body determined by the trackable body position determiner, to store the coordinate position of the first surface point responsive to a user engaging one of the following: an input field displayed on the graphical user interface and a switch operably coupled to the trackable body, to determine a coordinate position of a second surface point position responsive to a three-dimensional coordinate position of the trackable body reference point of the trackable body, to display the coordinate position of the second surface point position on the graphical user interface, and to determine and display a linear distance between the first surface point position and the second surface point position to thereby provide patient surface relative positioning data.

16. A system to facilitate and verify proper target alignment for radiation delivery so that a treatment plan can be more accurately applied to a patient, the system comprising:

a radiation delivery apparatus to provide radiation delivery to the patient, the radiation delivery apparatus including a radiation emitter adapted to emit a radiation beam having a theoretical point source and central beam axis and a rotating assembly carrying the radiation emitter to define an emitter carrier rotating assembly adapted to direct the radiation beam through a target of the patient and having a rotational path in a distinct plane and an axis of rotation to direct the radiation beam at a three-dimensional coordinate position defining an isocenter of an isocenter coordinate system of the radiation delivery apparatus, the theoretical point source being a predetermined distance from the isocenter to define a source-to-axis distance;

a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;

a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;

a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view of the trackable body detector, the trackable body position determiner having memory associated therewith and position determiner program product stored therein;

a target alignment analyzing computer in communication with the trackable body position determiner to determine proper target alignment for the radiation delivery apparatus, the target alignment analyzing computer having a processor and memory coupled to the processor to store operating instructions, the three-dimensional coordinate position of the isocenter, and the source-to-axis distance of the radiation delivery apparatus, therein, and a display coupled to the processor to display target alignment data; and a target alignment analyzing program product stored in the memory of the target alignment analyzing computer to facilitate and verify proper target alignment for radiation delivery, the target alignment analyzing program product including a point collection table former configured to receive a list of a plurality of pre-defined surface points, to display the list of the plurality of pre-defined surface points on a graphical user interface, and configured, responsive to a user sequentially positioning the trackable body reference point of the trackable body in contact with each separate one of a plurality of surface point locations corresponding to the respective separate one of the plurality of pre-defined surface points and engaging one of the following: an input field displayed on the graphical user interface and a switch operably coupled to the trackable body, to determine, store, and display for each of the plurality of pre-defined surface points one or both of a surface point three-dimensional coordinate position and a source-to-surface distance defining surface point data, the displayed list of the plurality of pre-defined surface points and corresponding displayed surface point data collectively forming a surface point locations table viewable by a user to ensure proper patient three-dimensional positioning across the plurality of surface points.

17. A system to facilitate and verify proper target alignment for radiation delivery so that a radiation treatment can be more accurately applied to a patient, the system comprising:
a radiation delivery apparatus to provide radiation delivery to the patient, the radiation delivery apparatus including a radiation emitter adapted to emit a radiation beam having a theoretical point source and central beam axis and a rotating assembly carrying the radiation emitter to an emitter carrier rotating assembly positionable to direct the radiation beam through a target of the patient and having a rotational path in a distinct plane and an axis of rotation to direct the radiation beam at a three-dimensional coordinate position defining an isocenter of an isocenter coordinate system of the radiation delivery apparatus, the theoretical point source having a predetermined distance from the isocenter to define a source-to-axis distance;
a trackable body having a preselected coordinate system assigned thereto, a trackable body reference point positioned with respect to the preselected coordinate system, and a plurality of separate and spaced-apart indicators each connected at a separate preselected position thereon to thereby indicate a position of the trackable body reference point;
a trackable body detector having a detector body adapted to be positioned separate and spaced apart from the trackable body at a three-dimensional trackable body detector reference location and positioned to detect a three-dimensional position of each of the plurality of indicators to thereby produce a plurality of position signals representing such three-dimensional indicator positions, the trackable body detector having a field of view;
a trackable body position determiner in communication with the trackable body detector and responsive to the plurality of position signals produced by the trackable body detector to determine a three-dimensional coordinate position of the trackable body reference point when a preselected number of the plurality of indicators are simultaneously positioned within the field of view and when positioned adjacent a surface of the patient to define a surface point position;
a target alignment analyzing computer in communication with the trackable body position determiner to determine proper target alignment for the radiation delivery apparatus and having a processor and memory coupled to the processor to store operating instructions, the three-dimensional coordinate position of the isocenter, and the source-to-axis distance of the radiation delivery apparatus, therein, and a display coupled to the processor to display target alignment data; and
a target alignment analyzing program product stored in the memory of the target alignment analyzing computer to facilitate and verify proper target alignment for radiation delivery, the target alignment analyzing program product including a contour determiner configured to receive a plurality of surface point positions provided by the trackable body position determiner and responsive to a user of the system positioning the trackable body reference point of the trackable body along a contour of a contoured human body part, to determine the contour of the contoured human body part, and responsive to the contour of the contoured body part, to determine an optimum initial emitter angle of rotation and beam width for the radiation delivery apparatus at isocenter to include an optimum emitter angle for medial and lateral radiation beams to deliver radiation to the contoured body part.

18. A system as defined in claim 17, wherein the contour determiner is further configured to determine two three-dimensional coordinate positions of the preselected trackable body reference point when adjacent a corresponding first and second selected separate and spaced apart patient surface point positions, the first selected point defining a first setup surface point position and the second selected point defining a second setup surface point position, and responsive to determining the first setup and the second setup surface point positions, to determine a point-to-point line between the first setup and the second setup surface point positions, to thereby determine a radiation beam field edge boundary defining a boundary between the contoured body part and an adjacent extent of the patient not receiving radiation.

19. A tracker comprising an optically trackable body having:
an elongate main body including a proximal body end portion, a distal body end portion, and a medial body portion extending therebetween;
an extension member including a proximal end portion connected to the distal body end portion of the main body, a distal end portion, and a medial portion extending therebetween, the distal end portion including an annular recess and having a trackable body reference point associated therewith;
a plurality of separate and spaced-apart optical indicators each connected at a separate preselected position of the medial body portion of the main body of the optically trackable body and having a preselected segment length between each pair combination of the plurality of indicators, and adapted to be optically tracked to thereby indicate a position of the trackable body reference point; and
a spherical body rotatably positioned within the annular recess to contact a surface of the patient and to roll when manipulated along the surface of the patient to enhance movement of the optically trackable body when in contact with the surface of the patient, the trackable body reference point located and maintained at a distal-most portion of the extension member to continually reference a current surface position of the surface of the patient when the spherical body is being rotated in contact with the surface of the patient.

20. A tracker comprising:
an optically trackable body having a proximal end portion, a distal end portion, and a medial body portion extending therebetween, the distal end portion having a trackable body reference point associated therewith;
a plurality of separate and spaced-apart optical indicators each connected at a separate preselected position of the medial body portion of the optically trackable body and having a preselected segment length between each pair combination of the plurality of indicators, and adapted to be optically tracked to thereby indicate a position of the trackable body reference point; and
a switch adapted to be manipulated by the user to mask at least one of the plurality of optical indicators to thereby disable provision of position data for the trackable body reference point, and adapted to be manipulated by the user to unmask the at least one of the plurality of indicators to thereby enable provision of position data for the trackable body reference point.

21. A tracker comprising an optically trackable body having:
- an elongate main body defining a handle including a proximal body end portion, a distal body end portion, and a medial body portion extending therebetween and having a longitudinal axis;
- a flat-shaped extension member including a proximal end portion connected to the distal body end portion of the main body, a distal end portion having a trackable body reference point located adjacent a distal-most portion of the extension member, and a medial portion extending therebetween, the medial portion of the extension member having a width substantially greater than depth and having an obtuse angular bend with respect to the longitudinal axis of the main body portion to allow pivoting of the trackable body when positioned on a flat surface to thereby allow a user to manipulate the trackable body reference point into contact with a lower patient surface of a patient positioned facing a substantially flat upper surface of a treatment table, between the lower patient surface of the patient and the substantially flat upper surface of the treatment table without substantial movement of the patient; and
- a plurality of separate and spaced-apart optical indicators each connected at a separate preselected position of the optically trackable body and having a preselected segment length between each pair combination of the plurality of indicators, and adapted to be optically tracked to thereby indicate a position of the trackable body reference point.

22. A computer readable medium that is readable by a computer to facilitate and verify proper target alignment for radiation delivery so that a treatment plan can be more accurately applied to a patient, the computer readable medium comprising a set of instructions stored thereon that, when executed by the computer, cause the computer to perform the following operations:
- tracking a position of a subset of a plurality of separate and spaced-apart optical indicators positioned on an optically trackable body, to determine a three-dimensional coordinate position of a trackable body reference point associated with the optically trackable body;
- determining, responsive to the tracking, the three-dimensional coordinate position of the trackable body reference point when in contact with an outer surface of the patient located outside a plane of rotation of a radiation emitter carrier rotating assembly of a radiation delivery apparatus defining a surface point position located on the outer surface of the patient; and
- determining, responsive to the surface point position, a component of a distance within the plane of rotation of the emitter carrier rotating assembly along a central axis of a radiation emitter carried by a radiation delivery apparatus and between a theoretical point source of the radiation emitter and the surface point position located on the outer surface of the patient defining a source-to-surface distance.

23. A computer readable medium as defined in claim 22, wherein the central axis is directed to an isocenter of the apparatus, and wherein the computer readable medium further comprises a set of instructions that, when executed by the computer, cause the computer to perform the following operation:
- determining, responsive to the determining of the surface point position, an angle of rotation of the emitter carrier rotating assembly that positions a path of the central axis of the emitter simultaneously through the surface point position and the isocenter defining an emitter carrier rotating assembly angle of rotation; and
- providing data to display the emitter carrier rotating assembly angle of rotation on a graphical user interface.

24. A computer readable medium as defined in claim 22, wherein the computer readable medium further comprises a set of instructions that, when executed by the computer, cause the computer to perform the following operation:
- determining, responsive to the determining of the surface point position, an off-plane distance between the surface point position and the plane of rotation for the emitter carrier rotating assembly; and
- providing data to display the off-plane distance on a graphical user interface to provide a user a visual indication of a distance required to move a target normal to the plane of rotation for the emitter carrier rotating assembly to position the target within the plane of rotation of the emitter carrier rotating assembly.

25. A computer readable medium that is readable by a computer to facilitate and verify proper target alignment for radiation delivery so that a treatment plan can be more accurately applied to a patient, the computer readable media comprising a set of instructions stored thereon that, when executed by the computer, cause the computer to perform the following operations:
- tracking a position of a subset of a plurality of separate and spaced-apart optical indicators positioned on an optically trackable body, to determine a three-dimensional coordinate position of a trackable body reference point associated with the optically trackable body;
- determining, responsive to the tracking, the three-dimensional coordinate position of the trackable body reference point when in contact with a first patient surface defining a first surface point position;
- determining, responsive to the first surface point position, a component of a distance along a central axis of a radiation emitter carried by an emitter carrying rotating assembly of a radiation delivery apparatus between a theoretical point source of the radiation emitter and the first surface point position located on the first patient surface of the patient defining a first source-to-surface distance for the first surface point position;
- determining, responsive to the determining of the first surface point position, an angle of rotation of the emitter carrier rotating assembly that positions the central axis of the emitter simultaneously through the first surface point position and an isocenter of the apparatus to define a first emitter rotating assembly angle of rotation;
- forming, responsive to tracking the position of the trackable body reference point, a representation of a location of the trackable body reference point relative to a second surface point position on a second opposite patient surface of the patient located along the emitter rotating assembly angle of rotation, to thereby aid the user in positioning the trackable reference body reference point in contact with the second surface point position;
- determining, responsive to the user positioning of the trackable reference body reference point in contact with the second patient surface of the patient, a three-dimensional coordinate position of the second surface point position;
- determining, responsive to the determining of the second surface point position, a component of a distance between the theoretical point source and the second surface point position to define a second source-to-surface distance; and determining, responsive to the determining of the first and the second source-to-surface distances, or responsive to the determining of the first and the second surface point positions, a patient thickness of the patient along the emitter central axis between the first and the second surface point positions to define a central axis thickness, to thereby facilitate and verify proper target alignment.

26. A computer readable medium as defined in claim 25, the computer readable medium further comprises a set of instructions that, when executed by the computer, cause the computer to perform the following operations:
providing to a display data to display the central axis thickness to the user; and
providing to a display, data to display the angle of rotation of the emitter carrier rotating assembly that positions the central axis of the emitter simultaneously through the second surface point position and the isocenter.

27. A computer readable medium as defined in claim 25, wherein the radiation emitter is carried by an emitter carrying rotating assembly having a plane of rotation, and wherein the computer readable medium further includes instructions that, when executed by the computer, cause the computer to provide visual feedback to the user further causes the computer to perform the following operations:
determining, responsive to the tracking, a plurality of positions of the trackable body reference point;
determining, responsive to the determining of the plurality of positions of the trackable body reference point, a corresponding plurality of off-plane distances between each of the plurality of positions of the trackable body reference point and the plane of rotation for the emitter carrier rotating assembly; and
providing to a display, data to display sequentially each of the plurality of off-plane distances to thereby aid the user in positioning the trackable body reference point in contact with the second surface point position.

28. A computer readable medium that is readable by a computer to facilitate and verify proper target alignment for radiation delivery so that a treatment plan can be more accurately applied to a patient, the computer readable medium further comprises a set of instructions stored thereon that, when executed by the computer, cause the computer to perform the following operations:
tracking a position of a subset of a plurality of separate and spaced-apart optical indicators positioned on an optically trackable body, to determine a three-dimensional coordinate position of a trackable body reference point associated with the optically trackable body;
determining, responsive to the tracking, the three-dimensional coordinate position of the trackable body reference point when in contact with a first patient surface defining a first surface point position;
determining, responsive to the first surface point position, a component of a distance along a central axis of a radiation emitter carried by an emitter carrying rotating assembly of a radiation delivery apparatus between a theoretical point source of the radiation emitter and the first surface point position located on the first patient surface of the patient defining a first source-to-surface distance for the first surface point position;
receiving a preselected emitter rotating assembly angle of rotation;
forming, responsive to tracking the position of the trackable body reference point, a representation of a location of the trackable body reference point relative to a second surface point position on a second opposite patient surface of the patient along the preselected emitter rotating assembly angle of rotation, to thereby aid the user in positioning the trackable reference body reference point adjacent the second surface point position;
determining, responsive to the user positioning of the trackable reference body reference point in contact with the second patient surface of the patient, a three-dimensional coordinate position of the second surface point position;
determining, responsive to the determining of the second surface point position, a component of a distance within a plane of rotation of the emitter carrier rotating assembly between the theoretical point source of the radiation emitter and the second surface point position along the preselected emitter rotating assembly angle of rotation to define a second source-to-surface distance; and
determining, responsive to one or more of the following: the determining of the first and the second source-to-surface distances and the determining of the first and the second surface point positions, a patient thickness of the patient along an axis between the first and the second surface point positions along the preselected emitter rotating assembly angle of rotation, to thereby facilitate and verify proper target alignment.

29. A computer readable medium as defined in claim 28, wherein the instructions that, when executed by the computer, cause the computer to provide visual feedback to the user, further causes the computer to perform the following operations:
determining, responsive to the tracking, a plurality of positions of the trackable body reference point;
determining, responsive to determining the plurality of positions of the trackable body reference point, a corresponding plurality of off-plane distances between each of the plurality of positions of the trackable body reference point and a plane including the three-dimensional coordinate position of the first surface point position and the second surface point position; and
providing to a display, data to display sequentially each of the plurality of off-plane distances to provide a user a visual indication of a distance required to move the trackable body reference point normal to a first surface point plane to position the trackable body reference point in contact with the second surface of the patient at the second surface point position.

30. A computer readable medium that is readable by a computer to facilitate and verify proper target alignment for radiation delivery so that a treatment plan can be more accurately applied to a patient, the computer readable medium comprising a set of instructions stored thereon that, when executed by the computer, cause the computer to perform the following operations:
receive a list of a plurality of pre-defined surface points;
tracking a position of a subset of a plurality of separate and spaced-apart optical indicators positioned on an optically trackable body when being moved, to determine a plurality of positions of a preselected trackable body reference point associated with the optically trackable body;
responsive to the tracking and responsive to sequential engagement of one of the following: an input field displayed on a graphical user interface in communication with the computer and a switch operably coupled to the trackable body, and for each of the plurality of the pre-defined surface points, determining the position of the preselected trackable body reference point when in contact with a corresponding separate and spaced apart patient surface point located at a respective pre-selected surface point position of a plurality of surface point positions defining a respective plurality of sample locations;

forming, responsive to the plurality of surface point positions, a point collection table including a three-dimensional coordinate point location for each of the plurality of surface point positions; and providing to a display, data to display the point collection table to provide to a user a graphical reference to isocenter for each of the plurality of sample locations to thereby allow the user to simultaneously verify proper patient three-dimensional positioning across at-each-of the plurality of sample locations, the displayed point collection table including each member of the list of the plurality of pre-defined surface points and corresponding three-dimensional coordinate point location.

31. A computer readable medium that is readable by a computer to facilitate and verify proper target alignment for radiation delivery so that a treatment plan can be more accurately applied to a patient, the computer readable medium comprising a set of instructions stored thereon that, when executed by the computer, cause the computer to perform the following operations:

tracking a position of a subset of a plurality of separate and spaced-apart optical indicators positioned on an optically trackable body, to determine a plurality of positions of a preselected trackable body reference point associated with the optically trackable body when being moved;

determining, responsive to the tracking and user positioning of the optically trackable body and responsive to a user engaging one of the following:

an input field displayed on a graphical user interface operably coupled to the computer and a switch operably coupled to the trackable body, a user-selected three-dimensional coordinate position of the trackable body reference point on a patient surface when in contact with the patient surface defining a user-selected surface point position;

determining, responsive to the tracking and the determining of the user-selected surface point position, a relative point-to-point distance between the user-selected surface point position and a current position of the preselected trackable body reference point defining a floating user-preselected point position; and providing to a display, data to display the relative point-to-point distance to the user to provide the user a graphical point-to-point linear distance reference to the surface point position thereby facilitate and verify proper target alignment.

32. A computer readable medium that is readable by a computer to facilitate and verify proper target alignment for radiation delivery so that a treatment can be more accurately applied to a patient, the computer readable medium comprising a set of instructions stored thereon that, when executed by the computer, cause the computer to perform the following operations:

tracking a position of a subset of a plurality of separate and spaced-apart optical indicators positioned on an optically trackable body, to determine a plurality of three-dimensional coordinate positions of a preselected trackable body reference point associated with the optically trackable body when the optically trackable body is translated along a contoured surface of a contoured body part of the patient;

determining, responsive to the tracking, the plurality of three-dimensional coordinate positions of the preselected trackable body reference point when translated in contact with the contoured surface of the contoured body part of the patient to define a respective plurality of surface point positions;

forming, responsive to determining the plurality of surface point positions, a representation of a surface contour of the contoured surface of the contoured body part of the patient;

responsive to the surface contour of the contoured body part, determining an optimum emitter angle and beam width of a radiation delivery apparatus to deliver radiation to the contoured body part to include an optimum emitter angle for medial and lateral radiation beams to enhance delivery of deliver radiation to the contoured body part.

33. A computer readable medium as defined in claim 32, the computer readable medium further comprising a set of instructions that, when executed by the computer, cause the computer to perform the following operation:

comparing the contour formed using the optically trackable body to a respective contour stored in a treatment plan, to thereby determine if patient translation is required.

34. A computer readable medium as defined in claim 32, the computer readable medium further comprising a set of instructions that, when executed by the computer, cause the computer to perform the following operations:

determining, responsive to the tracking, two three-dimensional coordinate positions of the preselected trackable body reference point when in contact with a corresponding two selected separate and spaced apart patient surface point positions, a first selected point defining a first setup surface point position and a second selected point defining a second setup surface point position; and forming, responsive to the first setup and the second setup surface point positions, a point-to-point line between the first setup and the second setup surface point positions, to thereby determine a radiation beam field edge boundary defining a boundary between the contoured body part and an adjacent extent of the patient not receiving radiation.

35. A computer readable medium as defined in claim 34, the computer readable medium further comprising a set of instructions that, when executed by the computer, cause the computer to perform the following operation:

receiving a predetermined three-dimensional coordinate position of isocenter of a radiation treatment apparatus; and wherein the determining the optimum beam width is performed responsive to the determining of the radiation beam field edge boundary and the receiving of the predetermined three-dimensional coordinate position of isocenter, to provide an amount of flash to ensure desired radiation beam coverage of the contoured body part of the patient.

* * * * *